US009889145B2

(12) United States Patent
Morici et al.

(10) Patent No.: US 9,889,145 B2
(45) Date of Patent: Feb. 13, 2018

(54) METHODS TO TREAT INFECTIONS

(71) Applicant: The Administrators of the Tulane Educational Fund, New Orleans, LA (US)

(72) Inventors: Lisa Ann Morici, Mandeville, LA (US); Saja Asakrah, Saint Clair Shores, MI (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 0 days.

(21) Appl. No.: 14/258,045

(22) Filed: Apr. 22, 2014

(65) Prior Publication Data

US 2014/0329777 A1 Nov. 6, 2014

Related U.S. Application Data

(60) Provisional application No. 61/814,983, filed on Apr. 23, 2013.

(51) Int. Cl.

*A61K 31/415* (2006.01)
*A61K 31/40* (2006.01)
*A61K 31/255* (2006.01)
*A61K 31/19* (2006.01)
*A61K 31/63* (2006.01)
*A61K 45/06* (2006.01)
*A61K 31/196* (2006.01)
*A61K 31/18* (2006.01)
*A61K 31/343* (2006.01)

(52) U.S. Cl.

CPC ............ *A61K 31/63* (2013.01); *A61K 31/415* (2013.01); *A61K 45/06* (2013.01); *A61K 31/18* (2013.01); *A61K 31/19* (2013.01); *A61K 31/196* (2013.01); *A61K 31/343* (2013.01)

(58) Field of Classification Search

CPC ...... A61K 31/18; A61K 31/19; A61K 31/196; A61K 31/343; A61K 31/4135

USPC ......................... 514/420, 403, 406, 518, 557

See application file for complete search history.

(56) References Cited

U.S. PATENT DOCUMENTS

| | | | | |
|---|---|---|---|---|
| 6,551,584 | B2 | 4/2003 | Bandyopadhyay et al. | |
| 7,776,902 | B2 * | 8/2010 | Del Soldato et al. | 514/406 |
| 2003/0191051 | A1 * | 10/2003 | Needleman et al. | 514/8 |

OTHER PUBLICATIONS

Chiu et al., "Pharmacological Exploitation of an Off-Target Antibacterial Effect of the Cyclooxygenase-2-Inhibitor Celecoxib against Francisella tularensis", Antimicrobial Agents and Chemotherapy, vol. 53, No. 7, pp. 2998-3002 (2009).*

Valade et al., "Susceptibility of 71 French isolates of *Francisella tularensis* subsp. *holarctica* to eight antibiotics and accuracy of the Etest method", Journal of Antimicrobial Chemotherapy, vol. 62, No. 1, pp. 208-210 (2008).*

Morici, "Post-Exposure Therapeutic Efficacy of COX-2 Inhibition against Pneumonic Melioidosis" Oral Presentation at the 11th ASM Biodefense and Emerging Diseases Research Meeting, Feb. 27, 2013, Session "022 Therapeutics and Immune Response" (abstract at 290—Asakrah et al.), 25 pages.

Morici et al., "Differential susceptibility of inbred mouse strains to Burkholderia thailandensis aerosol infection" Microb. Pathog. (2010) vol. 48, pp. 9-17.

Nieves et al., "A naturally derived outer-membrane vesicle vaccine protects against lethal pulmonary Burkholderia pseudomallei infection" Vaccine (2011) vol. 29, pp. 8381-8389.

Nokta et al., "Human immunodeficiency virus replication: modulation by cellular levels of cAMP" AIDS Res. Hum. Retroviruses (1992) vol. 8, No. 7, pp. 1255-1261.

Ozaki et al., "Cyclooxygenase metabolites are compartmentalized in the human lower respiratory tract" J. Appl. Physiol. (1987) vol. 62, No. 1, pp. 219-222.

Peskar et al., "Role of cyclooxygenase-1 and -2, phospholipase C, and protein kinase C in prostaglandin-mediated gastroprotection" J. Pharmacol. Exp. Ther. (2003) vol. 305, No. 2, pp. 1233-1238.

Reddy et al., "Selective inhibition of COX-2 improves early survival in murine endotoxemia but not in bacterial peritonitis" Am. J. Physiol. Lung Cell Mol. Physiol. (2001) vol. 281, pp. L537-L543.

Rodriguez et al., "Arginase I in myeloid suppressor cells in induced by COX-2 in lung carcinoma" J. Exp. Med. (2005) vol. 202, No. 7, pp. 931-939.

Rozak et al., "CpG oligodeoxyribonucleotides protect mice from Burkholderia pseudomallei but not Francisella tularensis Schu S4 aerosols" J. Immune Based Ther. Vaccines (2010) vol. 8, Article 2, 5 pages.

Sadikot et al., "Bacterial clearance of Pseudomonas aeruginosa is enhanced by the inhibition of COX-2" Eur. J. Immunol. (2007) vol. 37, pp. 1001-1009.

Schmelzer et al., "Enhancement of antinociception by coadministration of nonsteroidal anti-inflammatory drugs and soluble epoxide hydrolase inhibitors" Proc. Natl Acad. Sci. U.S.A. (2006) vol. 103, No. 37, pp. 13646-13651.

Serezani et al., "Prostaglandin E2 suppresses bacterial killing in alveolar macrophages by inhibiting NADPH oxidase" Am. J. Respir. Cell Mol. Biol. (2007) vol. 37, No. 5, pp. 562-570.

Sivalingam et al., "Pre- and post-exposure prophylaxis of experimental Burkholderia pseudomallei infection with doxycycline, amoxicillin/clavulanic acid and co-trimoxazole" J Antimicrobial Chemotherapy (2008) vol. 61, pp. 674-678.

Skyberg et al., "Nasal Acai polysaccharides potentiate innate immunity to protect against pulmonary Francisella tularensis and Burkholderia pseudomallei Infections" PLoS Pathog. (2012) vol. 8, Issue 3, Article ID e1002587, 14 pages.

(Continued)

*Primary Examiner* — Kevin E Weddington

(74) *Attorney, Agent, or Firm* — Arrigo, Lee & Guttman LLP; Harry J. Guttman

(57) ABSTRACT

Methods to treat infectious diseases are disclosed herein. Some embodiments of the invention include administration of one or more COX inhibitors (e.g., COX-1 or COX-2 inhibitors) to treat infectious diseases. Other embodiments of the invention include administration of one or more COX inhibitors (e.g., COX-1 or COX-2 inhibitors) and administration of one or more antibiotics to treat infectious diseases.

36 Claims, 29 Drawing Sheets

(56) References Cited

OTHER PUBLICATIONS

Stevens et al., "Actin-binding proteins from Burkholderia mallei and Burkholderia thailandensis can functionally compensate for the actin-based motility defect of a Burkholderia pseudomallei bimA mutant" J. Bacteriol. (2005) vol. 187, No. 22, pp. 7857-7862.
Titball, "Bacterial phospholipases C" Microbiol. Rev. (1993) vol. 57, No. 2, pp. 347-366.
Uematsu et al., "Detection of pathogenic intestinal bacteria by Toll-like receptor 5 on intestinal CD11c+ lamina propria cells" Nat. Immunol. (2006) vol. 7, No. 8, pp. 868-874.
Vancheri et al., "The lung as a privileged site for the beneficial actions of PGE2" Trends Immunol. (2004) vol. 25, No. 1, pp. 40-46.
Warawa, "Evaluation of surrogate animal models of melioidosis" Front Microbiol. (2010) vol. 1, Article ID 141, 12 pages.
Warner et al., "Cyclooxygenases: new forms, new inhibitors, and lessons from the clinic" FASEB J. (2004) vol. 18, pp. 790-804.
Weischenfeldt et al., "Bone Marrow-Derived Macrophages (BMM): Isolation and Applications" Cold Spring Harbor Protocols (2008) vol. 3, No. 12, pp. 1-6.
West et al., "Activation of Toll-like receptors by Burkholderia pseudomallei" BMC Immunol. (2008a) vol. 9, Article ID 46, 10 pages.
West et al., "Inhalation of Burkholderia thailandensis results in lethal necrotizing pneumonia in mice: a surrogate model for pneumonic melioidosis," Trans. R. Soc. Trop. Med. Hyg. (2008b) vol. 102, Suppl. 1, pp. S119-S126.
White, "Melioidosis" Lancet (2003) vol. 361, pp. 1715-1722.
Wiersinga et al., "Melioidosis: Insights into the pathogenicity of Burkholderia pseudomallei" Nature Rev. Microbiol. (2006) vol. 4, pp. 272-282.
Wiersinga et al., "Toll-like receptor 2 impairs host defense in gram-negative sepsis caused by Burkholderia pseudomallei (melioidosis)" PLoS Med. (2007) vol. 4, Issue 7, Article ID e248, 14 pages.
Wiersinga et al., "Gene-expression profiles in murine melioidosis" Microbes Infect. (2008) vol. 10, pp. 868-877.
Wiersinga et al., "Immunity to Burkholderia pseudomallei" Curr. Opin. Infect. Dis. (2009) vol. 22, pp. 102-108.
Wiersinga et al., "Melioidosis" N. Engl. J. Med. (2012) vol. 367, pp. 1035-1044.
Woolard et al., "Respiratory Francisella tularensis live vaccine strain infection induces Th17 cells and prostaglandin E2, which inhibits generation of gamma interferon-positive T cells" Infect. Immun. (2008) vol. 76, No. 6, pp. 2651-2659.
Zhang et al., "The p38 mitogen-activated protein kinase signaling pathway is coupled to Toll-like receptor 5 to mediate gene regulation in response to Pseudomonas aeruginosa infection in human airway epithelial cells" Infect. Immun. (2007) vol. 75, No. 12, pp. 5985-5992.
Asakrah, "Role of Prostaglandin E2 in the pathogenesis of Burkholderia pseudomallei" (Submitted to Tulane Library system after Apr. 25, 2012) Ph.D. thesis, 129 pages.
Asakrah et al., "TLR2 and Prostaglandin E2 promote Burkholderia intracellular survival" Poster presented at 111th General Meeting of the American Society for Microbiology, May 21-24, 2011, New Orleans, 1 page.
Asakrah et al., "Post-Exposure Therapeutic Efficacy of COX-2 Inhibition Against Burkholderia pseudommallei" (2013a) Program and Abstracts Book of 11th ASM Biodefense and Emerging Diseases Research Meeting, Abstract 290 at p. 97, 2 pages.
Asakrah et al., "Post-Exposure Therapeutic Efficacy of COX-2 Inhibition Against Burkholderia pseudommallei" PLoS Neg. Trop. Dis. (2013b) vol. 7, Issue 5, Article ID e2212, 10 pages.
Ballinger et al., "Critical role of prostaglandin E2 overproduction in impaired pulmonary host response following bone marrow transplantation" J. Immunol. (2006) vol. 177, No. 8, pp. 5499-5508.
Beutler et al., "Genetic analysis of innate immunity: TIR adapter proteins in innate and adaptive immune responses," Microbes Infect. (2004) vol. 6, pp. 1374-1381.
Brett et al., "*Burkholderia thailandensis* sp. nov., a *Burkholderia pseuomallei*-like species" Int. J. Syst. Bacteriol. (1998) vol. 48, pp. 317-320.
Burtnick et al., "Burkholderia pseudomallei type III secretion system mutants exhibit delayed vacuolar escape phenotypes in RAW 264.7 murine macrophages" Infect. Immun. (2008) vol. 76, No. 7, pp. 2991-3000.
Ceballos-Olvera et al., "Inflammasome-dependent pyroptosis and IL-18 protect against Burkholderia pseudomallei lung infection while IL-1beta is deleterious" PLoS Pathog. (2011) vol. 12, Issue 12, Article ID e1002452, 13 pages.
Chang et al., "Macrophage arginase promotes tumor cell growth and suppresses nitric oxide-mediated tumor cytotoxicity" Cancer Res. (2001) vol. 61, pp. 1100-1106.
Chaowagul et al., "Melioidosis: a major cause of community-acquired septicemia in northeastern Thailand" J. Infect. Dis. (1989) vol. 159, No. 5, pp. 890-899.
Chaowagul et al., "Open-label randomized trial of oral trimethoprim-sulfamethoxazole, doxycycline, and chloramphenicol compared with trimethoprim-sulfamethoxazole and doxycycline for maintenance therapy of melioidosis" Antimicrob Agents Chemother. (2005) vol. 49, No. 10, pp. 4020-4025.
Cheng, "Melioidosis: advances in diagnosis and treatment" Current Opinion in Infect. Dis. (2010) vol. 23, pp. 554-559.
Cheng et al., "Melioidosis: epidemiology, pathophysiology, and management" Clin. Microbial Rev. (2005) vol. 18, No. 2, pp. 383-416. Also includes Erratum at Clin. Microbial Rev. (2007) vol. 20, No. 3, p. 533.
Cheng et al., "A randomized controlled trial of granulocyte colony-stimulating factor for the treatment of severe sepsis due to melioidosis in Thailand" Clin. Infect. Dis. (2007) vol. 45, pp. 308-314.
Currie et al., "The epidemiology of melioidosis in Australia and Papua New Guinea," Acta Trop. (2000), vol. 74, No. 2-3, pp. 121-127.
Currie et al., "The epidemiology and clinical spectrum of melioidosis: 540 cases from the 20 year Darwin prospective study" PLoS Neglected Trop. Dis. (2010) vol. 4, Issue 11, Article ID e900, 11 pages.
Das et al., "Modulation of the arginase pathway in the context of microbial pathogenesis: a metabolic enzyme moonlighting as an immune modulator" PLoS Pathog. (2010) vol. 6, Issue 6, Article ID e1000899, 7 pages.
Easton et al., "Combining vaccination and postexposure CpG therapy provides optimal protection against lethal sepsis in a biodefense model of human melioidosis" J. Infect. Dis. (2011) vol. 204, pp. 636-644.
Feterl et al., "The effect of different Burkholderia pseudomallei isolates of varying levels of virulence on toll-like-receptor expression," Trans. R. Soc. Trop. Med. Hyg. (2008) vol. 102, Suppl. 1, pp. S82-S88.
Fritz et al., "Naturally occurring melioidosis in a colonized rhesus monkey (*Macaca mulatta*)" Laboratory Animals (1986) vol. 20, pp. 281-285.
Galyov et al., "Molecular insights into Burkholderia pseudomallei and Burkholderia mallei pathogenesis" Annu. Rev. Microbiol. (2010) vol. 64, pp. 495-517.
Goodyear et al., "Protection from pneumonic infection with burkholderia species by inhalational immunotherapy" Infect. Immun. (2009) vol. 77, No. 4, pp. 1579-1588.
Gotoh et al., "Arginase II downregulates nitric oxide (NO) production and prevents NO-mediated apoptosis in murine macrophage-derived RAW 264.7 cells" J. Cell. Biol. (1999) vol. 144, No. 3, pp. 427-434.
Haas et al., "Cycloxygenase-2 inhibition augments the efficacy of a cancer vaccine" Clin. Cancer Res. (2006) vol. 12, pp. 214-222.
Haraga et al., "Burkholderia thailandensis as a model system for the study of the virulence-associated type III secretion system of Burkholderia pseudomallei" Infect. Immun. (2008) vol. 76, No. 11, pp. 5402-5411.
Harbrecht et al., "Timing of prostaglandin exposure is critical for the inhibition of LPS- or IFN-gamma-induced macrophage NO synthesis by PGE2," J. Leukoc. Biol. (1997) vol. 61, pp. 712-720.

(56) References Cited

OTHER PUBLICATIONS

Hawn et al., "Altered inflammatory responses in TLR5-deficient mice infected with Legionella pneumophila" J. Immunol. (2007) vol. 179, pp. 6981-6987.
Holt et al., "Modulation of host natural killer cell functions in breast cancer via prostaglandin E2 receptors EP2 and EP4" J. Immunother (2012) vol. 35, No. 2, pp. 179-188.
Inglis, "The Treatment of Melioidosis" Pharmaceuticals (2010) vol. 3, pp. 1296-1303.
Inglis et al., "Comparison of the susceptibilities of Burkholderia pseudomallei to meropenem and ceftazidime by conventional and intracellular methods" Antimicrob. Agents Chemother. (2004) vol. 48, No. 8, pp. 2999-3005.
Ireland et al., "Effective, broad spectrum control of virulent bacterial infections using cationic DNA liposome complexes combined with bacterial antigens" PLoS Pathog. (2010) vol. 6, Issue 5, Article ID e1000921, 16 pages.
Jones-Carson et al., "Nitric oxide-dependent killing of aerobic, anaerobic and persistent Burkholderia pseudomallei" Nitric Oxide (2012) vol. 27, pp. 25-31.
Judy et al., "Prophylactic application of CpG oligonucleotides augments the early host response and confers protection in acute melioidosis" Plos One (2012) vol. 7, Issue 3, Article ID e34176, 11 pages.
Kalinski, "Regulation of immune responses by prostaglandin E2" J. Immunol. (2012) vol. 188, pp. 21-28.
Kunkel et al., "Regulation of macrophage tumor necrosis factor production by prostaglandin E2" Biochem. Biophys. Res. Comm. (1986) vol. 137, No. 1, pp. 404-410.
Larson et al., "Pathogenesis of Burkholderia pseudomallei and Burkholderia mallei" Mil. Med. (2009) vol. 174, No. 6, pp. 647-651.
Levy et al., "Antibacterial resistance worldwide: causes, challenges and responses" Nat. Med. (2004) vol. 10, No. 12, pp. S122-S129.
Limmathurotsakul et al., "Increasing Incidence of Human Melioidosis in Northeast Thailand" Am J Trop Med Hyg. (2010), vol. 82, No. 6, pp. 1113-1117.
Limmathurotsakul et al., "Short Report: Repeat Blood Culture Positive for B. pseudomallei Indicates an Increased Risk of Death from Melioidosis" Am J Trop Med Hyg. (2011a) vol. 84, No. 6, pp. 858-861.
Limmathurotsakul et al., "Melioidosis: a clinical overview" Br Med Bull. (2011b) vol. 99, pp. 125-139.
Marotta et al., "Modulation of the induction of nitric oxide synthase by eicosanoids in the murine macrophage cell line J774" Br. J. Pharmacol. (1992) vol. 107, pp. 640-641.
Miyagi et al., "Role of reactive nitrogen and oxygen intermediates in gamma interferon-stimulated murine macrophage bactericidal activity against Burkholderia pseudomallei" Infect. Immun. (1997) vol. 65, No. 10, pp. 4108-4113.
Moreno et al., "The role of prostaglandin E2 in the immunopathogenesis of experimental pulmonary tuberculosis" Immunology (2002) vol. 106, pp. 257-266.
Morici, Presentation to the American Society for Microbiology, South Central Branch Meeting Oct. 27, 2012, 26 pages.
Agard et aL, "PGE2 suppression of innate immunity during mucosal bacterial infection" Frontiers in Cellular and Infection Microbiology (2013) vol. 3, No. 45, pp. 1-11.
Alba-Loureiro et al., "Evidence that arachidonic acid derived from neutrophils and prostaglandin E2 are associated with the induction of acute lung inflammation by lipopolysaccharide of *Escherichia coli*" Inflamm.Res. (2004) vol. 53, pp. 558-663.
Aronoff, "Cyclooxygenase inhibition in sepsis: is there life after death?" Mediators of Inflamm. (2012) Article ID 696897, 7 pages. (doi:10.1155/2012/696897).
Aronoff et al., "Prostaglandin E2 inhibits alveolar macrophage phagocytosis through an E-prostanoid 2 receptor-mediated increase in intracellular cyclic AMP" J. Immunol. (2004) vol. 173, pp. 559-565.
Aronoff et al., "E-prostanoid 3 receptor deletion improves pulmonary host defense and protects mice from death in severe *Streptococcus pneumoniae* infection" J. Immunol. (2009) vol. 183, pp. 2642-2649.
Aronoff et al., "E-prostanoid 2 receptor signaling suppresses lung innate immunity against *Streptococcus pneumoniae*" Prostaglandins & Other Lipid Mediat. (2012) vol. 98, pp. 23-30.
Asakrah et aL, "Post-exposure therapeutic efficacy of COX-2 inhibition against Burkholderia pseudomallei" PLoS Neglected Tropical Diseases (2013) vol. 7, No. 5, Article ID e2212, 10 pages. (doi:10.1371/journal.pntd.0002212).
Ballinger et al., "Critical role of prostagland in E2overproduction in impaired pulmonary host response following bone marrow transplantation" J. Immunol. (2006) vol. 177, pp. 5499-5508.
Bankhurst, "The modulation of human natural killer cell activity by prostaglandins" J. Clin. Lab.lmmunol. (1982) vol. 7, pp. 85-91.
Bansal et al., "M. bovis BCG induced expression of COX- 2 involves nitric oxide-dependent and -independent signaling pathways" J. Leukoc. Biol. (2009) vol. 85, pp. 804-816.
Berthelot et al., "Genotypic and phenotypic analysis of type III secretion system in a cohort of Pseudomonas aeruginosa bacteremia isolates: evidence for a possible association between O serotypes and exogenous" J. Infect. Dis. (2003) vol. 188, pp. 512-518.
Bowman et al., "Cyclooxygenase-2-mediated prostaglandin E2 production in mesenteric lymph nodes and in cultured macrophages and dendritic cells after infection with *Salmonella*" J. Immunol. (2004) vol. 172, pp. 2469-2475.
Bozyk et al., "Prostaglandin E2 and the pathogenesis of pulmonary fibrosis" Am. J. Respir. Cell Mol. Biol. (2011) vol. 45, No. 3, pp. 445-452.
Burch et al. "Cholera toxin and pertussis toxin stimulate prostaglandin E2 synthesis in a murine macrophage cellline" J. Pharmacol. Exp. Ther. (1988) vol. 244, pp. 765-773.
Edwards et al., "Chronic infection due to *Mycobacterium intracellulare* in mice: association with macrophage release of prostaglandin E2 and reversal by injection of indomethacin, muramyl dipeptide, or interferon-gamma" J Immunol (1986) vol. 136, No. 5, pp. 1820-1827.
Harbrecht et al., "Timing of prostaglandin exposure is critical for the inhibition of LPS- or IFN-y-induced macrophage NO synthesis by PGE2" Journal of Leukocyte Biology (1997) vol. 61, pp. 712-720.
Kumar et al., "ESAT-6 induced COX-2 expression involves coordinated interplay between PI3Kand MAPK signaling" Mol. Immunol. (2012) vol. 49, pp. 655-663.
Kuroda et al., "Sensitivity difference to the suppressive effect of prostaglandin E2 among mouse strains: a possible mechanism to polarize Th2 type response in BALB/c mice" Journal of immunology (2000) vol. 164, pp. 2386-2395.
Rangel Moreno et al., "The role of prostaglandin E2 in the immunopathogenesis of experimental pulmonary tuberculosis" Immunology (2002) vol. 106, pp. 257-266.
Rastogi et al., "Intracellular growth of *Mycobacterium avium* in human macrophages is linked to the increased synthesis of prostaglandin E2 and inhibition of the phagosome-lysosome fusions" FEMS Microbiol Immunol (1992) vol. 89, pp. 273-279.
Resta-Lenert et al., "Enteroinvasive bacteria alter barrier and transport properties of human intestinal epithelium: role of iNOS and COX-2" Gastroenterology (2002) vol. 122, No. 4, pp. 1070-1087.
Speelman et al., "Increased jejunal prostaglandin E2 concentrations in patients with acute cholera" Gut (1985) vol. 26, No. 2, pp. 188-193.
Stables et al., "Priming innate immune responses to infection by cyclooxygenase inhibition kills antibiotic-susceptible and -resistant bacteria" Blood (2010) vol. 116, No. 16, pp. 2950-2959.
Uchiya et al., "*Salmonella enterica* Serovar Typhimurium Infection Induces Cyclooxygenase 2 Expression in Macrophages: Involvement of *Salmonella Pathogenicity* Island 2" Infect Immun (2004) vol. 72, No. 12, pp. 6860-6869.
Wilson et al., "Immune Modulation as an Effective Adjunct Post-exposure Therapeutic for B. pseudomallei" PLOS Neglected Tropical Diseases (2016) vol. 10, No. 10, Article ID e0005065, 15 pages. (D01:10.1371/journal.ontd.0005065).

(56) References Cited

OTHER PUBLICATIONS

Xu et al., "Nontypeable Haemophilus influenzae induces COX-2 and PGE2 expression in lung epithelial cells via activation of p38 MAPK and NF-kappa B" Respiratory research (2008) Epub. 9:16, 9 pages. (doi:10.1186/1465-9921-9-16).

* cited by examiner

A

B

A

B

C

A

B

C

CFU/mg in lung homogenates from mice aerosol challenged with B. pseudomallei

D

CFU/mg in stomach homogenates from mice aerosol challenged with B. pseudomallei

METHODS TO TREAT INFECTIONS

CROSS REFERENCE TO RELATED APPLICATION

This application claims the benefit of U.S. Provisional Application No. 61/814,983, entitled "Methods to Treat Infections" filed Apr. 23, 2013, which is herein incorporated by reference in its entirety.

U.S. GOVERNMENT RIGHTS

This invention was made with U.S. Government support by grant number U54 AI057156 awarded by the National Institutes of Health, National Institute of Allergy and Infectious Diseases. The U.S. Government has certain rights in this invention.

BACKGROUND

The present invention relates to a method of treating infections. Some embodiments of the invention include administration of one or more COX inhibitors (e.g., COX-1 or COX-2 inhibitors) to treat infectious diseases. Other embodiments of the invention include administration of one or more COX inhibitors (e.g., COX-1 or COX-2 inhibitors) and administration of one or more antibiotics to treat infectious diseases.

U.S. Provisional Application No. 61/794,815 entitled "Efficacy of Cox-2 inhibition in melioidosis" with inventors Lisa A. Morici and Saja Asakrah, filed Mar. 15, 2013, is herein incorporated by reference in its entirety.

SUMMARY

Some embodiments of the invention include methods for treating a bacterial infectious disease in an animal comprising administering a therapeutically effective amount of one or more COX inhibitors to the animal. Other embodiments of the invention include methods for treating a bacterial infectious disease in an animal comprising administering a therapeutically effective amount of one or more COX inhibitors, and optionally administering a therapeutically effective amount of one or more antibiotics, wherein the administering steps are applied to the animal. Certain embodiments of the invention include methods for treating a bacterial infectious disease in an animal comprising administering a therapeutically effective amount of one or more COX inhibitors to the animal prior to exposure to the bacterial infectious disease; sometimes these methods can further comprise administering a therapeutically effective amount of one or more antibiotics to the animal prior to exposure to the bacterial infectious disease. Some embodiments of the invention include methods for prophylactically treating a bacterial infectious disease in an animal comprising administering a therapeutically effective amount of one or more COX inhibitors to the animal; sometime these methods can further comprise administering a therapeutically effective amount of one or more antibiotics to the animal. Other embodiments of the invention include methods for decreasing a bacterial load of an infecting bacteria in an animal comprising administering a therapeutically effective amount of one or more COX inhibitors to the animal; sometimes these methods can further comprise administering a therapeutically effective amount of one or more antibiotics to the animal. Some embodiments of the invention include methods for decreasing PGE-2 production in an animal comprising administering a therapeutically effective amount of one or more COX inhibitors to the animal; sometimes these methods can further comprise administering a therapeutically effective amount of one or more antibiotics to the animal.

Some embodiments of the inventions disclosed herein include methods for treating a bacterial infectious disease in an animal comprising administering a therapeutically effective amount of one or more COX inhibitors, and optionally administering a therapeutically effective amount of one or more antibiotics, wherein the administering steps are applied to the animal.

Other embodiments of the inventions disclosed herein include methods for treating a bacterial infectious disease comprising administering a therapeutically effective amount of one or more COX inhibitors (e.g., a COX-2 inhibitor), and optionally administering a therapeutically effective amount of one or more antibiotics, wherein the administering steps are applied to an animal exposed to the bacterial infectious disease.

Still other embodiments of the inventions disclosed herein include methods for decreasing a bacterial load of an infecting bacteria in an animal comprising administering a therapeutically effective amount of one or more COX inhibitors, and optionally administering a therapeutically effective amount of one or more antibiotics, wherein one or both administering steps are applied to the animal.

Further embodiments of the inventions disclosed herein include methods for decreasing PGE-2 production in an animal comprising administering a therapeutically effective amount of one or more COX inhibitors, and optionally administering a therapeutically effective amount of one or more antibiotics, wherein one or both administering steps are applied to the animal.

Additional embodiments of the inventions disclosed herein include methods for treating a bacterial infectious disease in an animal comprising administering a therapeutically effective amount of one or more COX inhibitors, and optionally administering a therapeutically effective amount of one or more antibiotics, wherein one or both administering steps are applied to the animal prior to exposure to the bacterial infectious disease.

Other embodiments of the inventions disclosed herein include methods for prophylactically treating a bacterial infectious disease in an animal comprising administering a therapeutically effective amount of one or more COX inhibitors, and optionally administering a therapeutically effective amount of one or more antibiotics, wherein one or both administering steps are applied to the animal.

In certain embodiments, the one or more administering steps are applied to the animal post-exposure to the bacterial infectious disease or prior to exposure to the bacterial infectious disease. Other embodiments include administering a therapeutically effective amount of one or more COX inhibitors not more than about 30 minutes after exposure, not more than about 24 hours after exposure, or not more than about 48 hours after exposure. In some instances, exposure is through contact with a mucous membrane.

In some embodiments, the methods can further comprise administering a therapeutically effective amount of one or more antibiotics. For example, the method can further comprise administering a therapeutically effective amount of one or more antibiotics applied to the animal post-exposure to the bacterial infectious disease or prior to exposure to the bacterial infectious disease. In other examples, the method can further comprise administering a therapeutically effective amount of one or more antibiotics selected from Sulfonamides, Cephalosporins, Sulfamethizole, Sulfamethoxazole, Sulfisoxazole, Trimethoprim-Sulfamethoxazole, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, and Doxycycline.

In some embodiments of the invention the method does not comprise administering an antibiotic to the animal.

Still other embodiments include administering a therapeutically effective amount of one or more antibiotics that is not optional.

In certain aspects, the bacterial infectious disease, when untreated or when treated by one or more antibiotics only, results in one or more of (a) increasing PGE-2 production in the animal, (b) increasing Arg2 expression in the animal, (c) increasing arginase production in the animal, (d) decreasing NO production in the animal, (e) weight loss in the animal, or (f) an increase in the bacterial load of the infecting bacteria in the animal.

In other aspects, the bacterial infectious disease, when untreated or when treated by one or more antibiotics only, results in increasing PGE-2 production in the animal, an increase in the bacterial load of the infecting bacteria in the animal, or both.

In some embodiments, the bacterial infectious disease is caused by a Gram-negative bacteria or a Gram-positive bacteria. In other embodiments, the bacterial infectious disease is caused by a drug-resistant bacteria or a multidrug-resistant bacteria. In further embodiments, the bacterial infectious disease is caused by a drug-resistant bacteria or a multidrug-resistant bacteria and the bacterial infectious disease results in increasing PGE-2 production in the animal. In other embodiments, the bacterial infectious disease is (a) a mucosal bacterial infection, a *Burkholderia* infection, a *Mycobacterial* infection, an *Enterococcus* infection, melioidosis, or tuberculosis, or (b) an infection caused by *Burkholderia pseudomallei, Burkholderia mallei, Burkholderia thailandensis, Mycobacterium tuberculosis, Francisella tularensis, Pseudomonas aeruginosa, Klebsiella pneumoniae, Salmonella*, or *Shigella flexneri.*

In certain embodiments, the one or more COX inhibitors is a COX-2 inhibitor. In other embodiments, the one or more COX inhibitors is Lumiracoxib, Etoricoxib, Valdicoxib, Roficoxib, Etodolac, Celecoxib, NS398, or Indomethacin. In some aspects, the dosage of the COX inhibitor is at least about two-fold higher compared to a COX inhibitor dosage for long term usage.

In certain embodiments, the bacterial load of the infecting bacteria in the animal decreases by at least about 50% in about 24 hours after starting the treatment. In other embodiments, the method results in one or more of (a) decreasing PGE-2 production in the animal, (b) decreasing Arg2 expression in the animal, (c) decreasing arginase production in the animal, (d) increasing NO production in the animal, (e) a lack of weight loss in the animal, or (f) a decrease in the bacterial load of the infecting bacteria.

In other embodiments, the bacterial infectious disease infects, in the animal, one or more of lung, liver, esophagus, stomach, eye, nose, sinus, ear, ear canal, mouth, hand, foot, urethra, or spleen.

In some aspects, an antibiotic is not administered to the animal.

In other aspects, the animal is not cured of the bacterial infectious disease by an antibiotic(s) only treatment.

In certain aspects of the invention, the animal is exposed to the bacterial infectious disease and exposure is through the skin, inhalation, injection, or contact with a mucous membrane.

In some embodiments, the manner of administration of one of the one or more COX inhibitors is by pill, liquid, aerosol, intranasal administration, topical administration, or injection.

In other embodiments, the manner of administration of the one or more COX inhibitors does not include topical administration of an eye.

In yet other embodiments, the manner of administration of one of the one or more antibiotics is by pill, liquid, aerosol, intranasal administration, topical administration, or injection.

In still other embodiments, the manner of administration of the one or more antibiotics does not include topical administration of an eye.

In other instances, the animal is post-exposure to the bacterial infectious disease.

In certain embodiments, the animal displays one or more symptoms of the bacterial infectious disease. In some instances, the animal is diagnosed with the bacterial infectious disease.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

NO levels in nor-NOHA treated cells two and four hours post-infection with Bt and Bp respectively. *$p<0.001$

FIG. 14A shows percent intracellular survival of Bps. FIG. 14B shows corresponding nitrite levels in BMDM supernatants. The data represent biological triplicates per time point. Error bars represent the SEM. Statistical significance was determined using a two way ANOVA with Bonferroni post-test. *$p<0.05$, ***$p<0.001$. Data is representative of two independent experiments.

FIG. 15A shows fold-change in mRNA expression for iNOS, arginase 1 (Arg1) and Arg2 in response to Bps was measured by RT-PCR. Error bars represent the SEM. FIG. 15B shows intracellular survival of Bps in BMDM pre-treated with 100 μM nor-NOHA for 30 minutes. FIG. 15C shows corresponding nitrite production by Bps-infected cells in the presence or absence of nor-NOHA. The data represent biological triplicates per time point. Error bars represent the SEM. Statistical significance was determined using a two way ANOVA with Bonferroni post-test. ***$p<0.001$. Data is representative of two independent experiments.

In FIG. 19D, using ELISA assays, PGE-2 was measured in lung homogenates of mock, Celecoxib-treated and DMSO-treated (uninfected) mice. *$p<0.05$ by Mann-Whitney test. shows bacterial burdens in (A) lung, (B) liver, and (C) spleen 48 hrs post-infection in Celecoxib-treated and DMSO (mock)-treated mice; (D) PGE-2 level in the lungs of mock, Celecoxib-treated and DMSO-treated mice.

***$p<0.001$.

Figure 21:
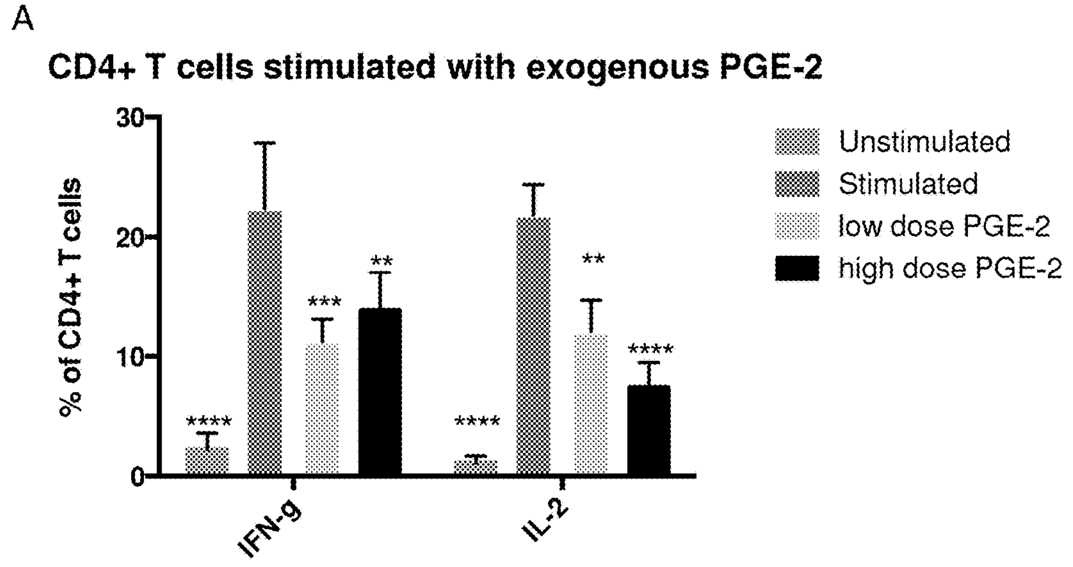
Figure 21:
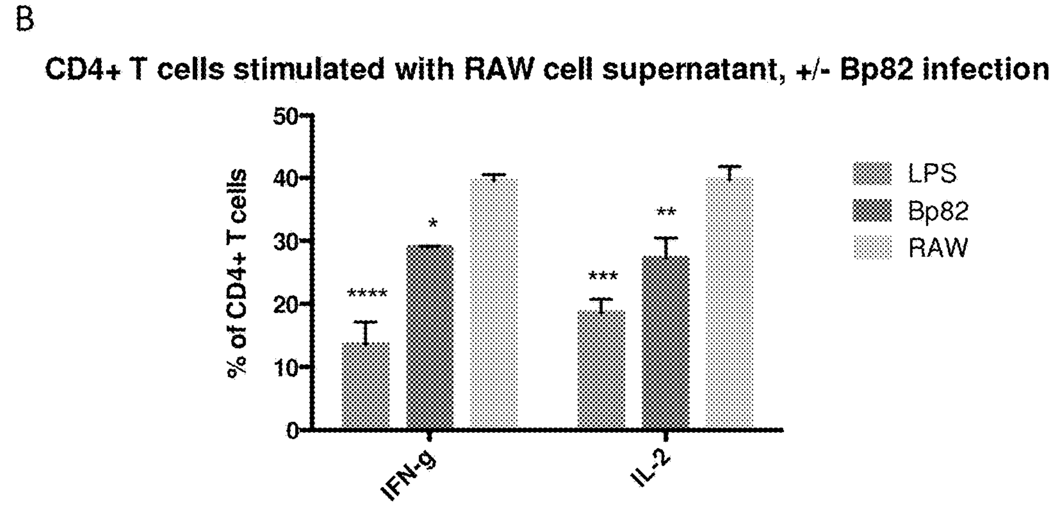
Figure 22:
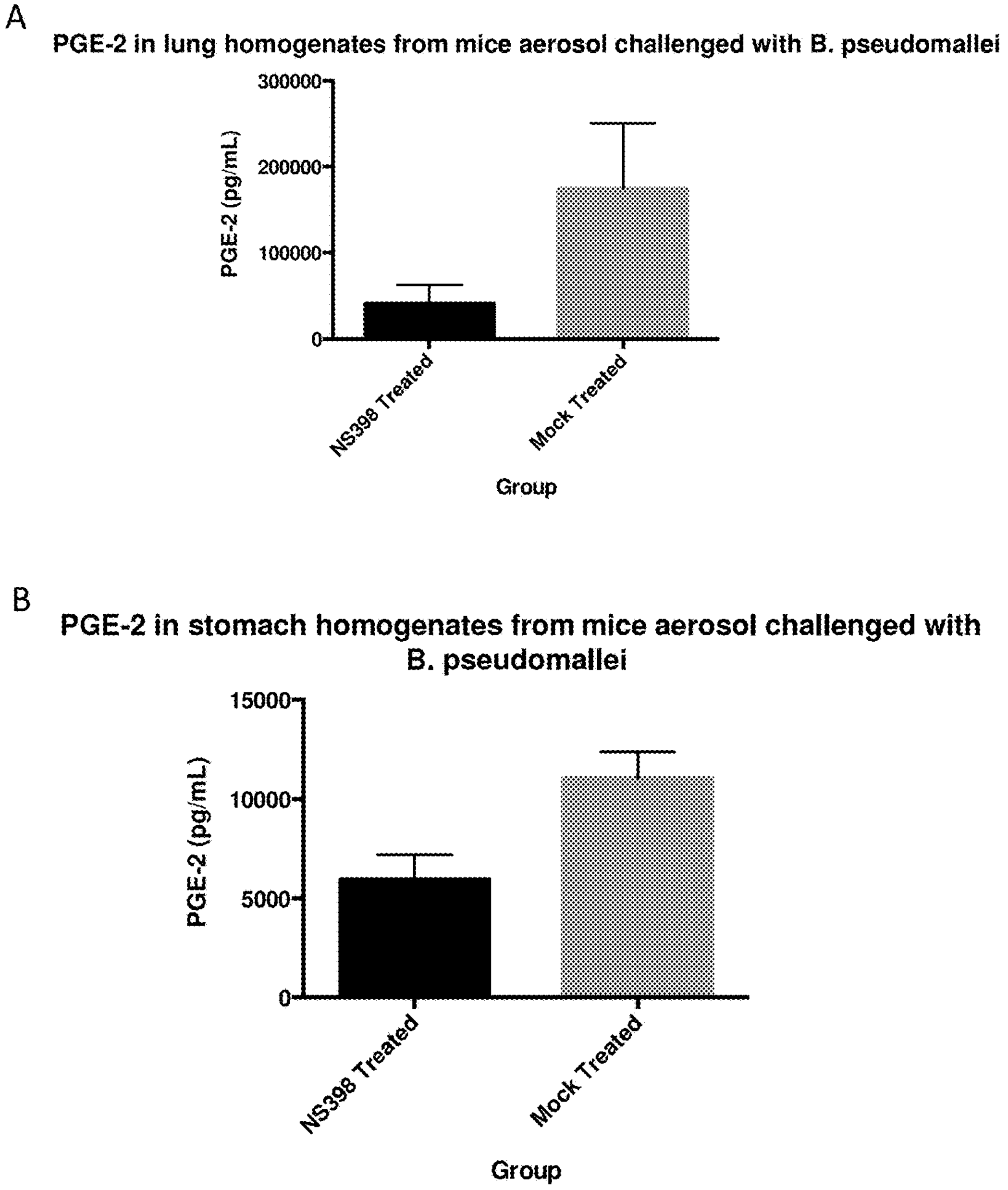
Figure 22:
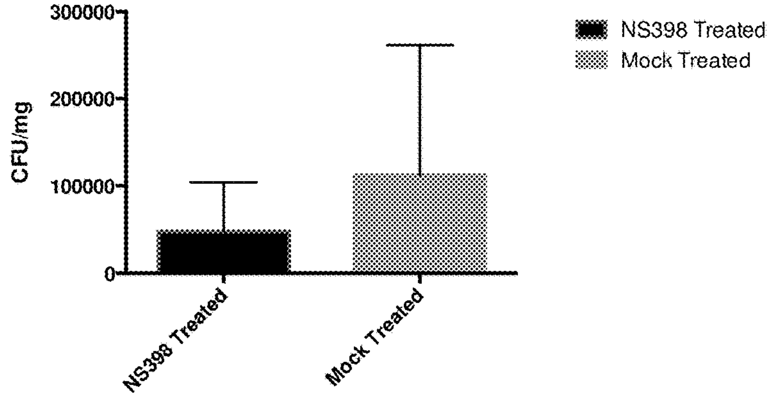
Figure 22:
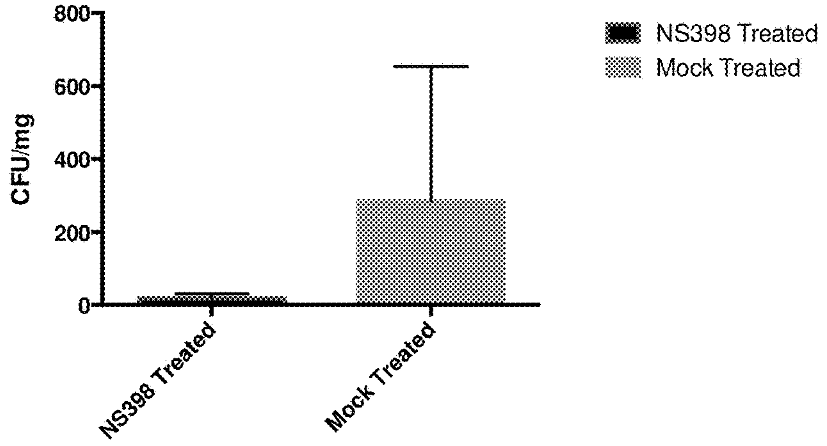

FIG. 21. Exogenous PGE-2 reduces IFN-γ and IL-2 production by stimulated CD4+ T-cells (FIG. 21A). Supernatant from Bp82-infected RAW macrophages reduces IFN-γ and IL-2 production by stimulated CD4+ T-cells (FIG. 21B). *$p<0.05$, $p<0.01$, *$p<0.001$, **$p<0.0001$ FIG. 22**. COX-2 inhibition in *B. pseudomallei* infected mice. FIG. 22A shows that COX-2 inhibition reduces PGE-2 in lung tissue. FIG. 22B shows that COX-2 inhibition reduces PGE-2 in stomach tissue. FIG. 22C shows that COX-2 inhibition suppresses growth of *B. pseudomallei* in lung tissue. FIG. 22D shows that COX-2 inhibition suppresses growth of *B. pseudomallei* in stomach tissue.

DETAILED DESCRIPTION

Some embodiments of the present invention include methods to treat an infectious disease (e.g., bacterial) comprising administering to an animal an amount (e.g., a therapeutically effective amount) of one or more COX inhibitors; in some embodiments, the methods can further include (e.g., optionally) administering an amount (e.g., a therapeutically effective amount) of one or more antibiotics. In some instances, the administration of a COX inhibitor, an antibiotic, or both are applied to the animal post-exposure or prior to exposure to the bacterial infectious disease. In some embodiments, the animal will be exposed to a bacterial infectious disease after one or more administrations of the COX inhibitor, after one or more administrations of the optional antibiotic, or after one or more administrations of both. In other embodiments, the animal will not be exposed to a bacterial infectious disease.

As used herein, the term “treating” (and its variations, such as “treatment”) is to be considered in its broadest context. In particular, the term “treating” does not necessarily imply that an animal is treated until total recovery. Accordingly, “treating” includes amelioration of the symptoms, relief from the symptoms or effects associated with a condition (e.g., bacterial infection or effects thereof), decrease in severity of a condition, or preventing, preventively ameliorating symptoms, or otherwise reducing the risk of developing a particular condition (e.g., bacterial infection or effects thereof). As used herein, reference to “treating” an animal includes prophylaxis (e.g., pre-exposure prophylaxis or post-exposure prophylaxis).

Some embodiments of the invention encompass a method for decreasing a bacterial load of an infecting bacteria in an animal comprising administering a therapeutically effective amount of one or more COX inhibitors, and optionally administering a therapeutically effective amount of one or more antibiotics, wherein one or both administering steps are applied to the animal.

Other embodiments of the invention encompass a method for decreasing PGE-2 production in an animal comprising administering a therapeutically effective amount of one or more COX inhibitors, and optionally administering a therapeutically effective amount of one or more antibiotics, wherein one or both administering steps are applied to the animal.

Still other embodiments of the invention encompass a method for treating a bacterial infectious disease in an animal comprising administering a therapeutically effective amount of one or more COX inhibitors, and optionally administering a therapeutically effective amount of one or more antibiotics, wherein the administering steps are applied to an animal that displays one or more symptoms of the bacterial infectious disease.

Some embodiments of the invention encompass a method for treating a bacterial infectious disease in an animal comprising administering a therapeutically effective amount of one or more COX inhibitors, and optionally administering a therapeutically effective amount of one or more antibiotics, wherein the administering steps are applied to an animal that is diagnosed with the bacterial infectious disease.

Some embodiments of the invention encompass a method for treating a bacterial infectious disease in an animal comprising administering a therapeutically effective amount of one or more COX inhibitors, and optionally administering a therapeutically effective amount of one or more antibiotics, wherein the administering steps are applied to an animal post-exposure to the bacterial infectious disease.

Certain embodiments of the invention encompass a method for prophylactically treating a bacterial infectious disease in an animal comprising administering a therapeutically effective amount of one or more COX inhibitors, and optionally administering a therapeutically effective amount of one or more antibiotics. In some embodiments of this prophylactic treatment, the animal will be exposed to a bacterial infectious disease after one or more administrations of the COX inhibitor, after one or more administrations of the optional antibiotic, or after one or more administrations of both. In other embodiments of this prophylactic treatment, the animal will not be exposed to a bacterial infectious disease.

Some embodiments of the invention include methods for treating a bacterial infectious disease in an animal comprising administering a therapeutically effective amount of one or more COX inhibitors to the animal. Other embodiments of the invention include methods for treating a bacterial infectious disease in an animal comprising administering a therapeutically effective amount of one or more COX inhibitors, and optionally administering a therapeutically effective amount of one or more antibiotics, wherein the administering steps are applied to the animal. Certain embodiments of the invention include methods for treating a bacterial infectious disease in an animal comprising administering a therapeutically effective amount of one or more COX inhibitors to the animal prior to exposure to the bacterial infectious disease; sometimes these methods can further comprise administering a therapeutically effective amount of one or more antibiotics to the animal prior to exposure to the bacterial infectious disease. Some embodiments of the invention include methods for prophylactically treating a bacterial infectious disease in an animal comprising administering a therapeutically effective amount of one or more COX inhibitors to the animal; sometime these methods can further comprise administering a therapeutically effective amount of one or more antibiotics to the animal. Other embodiments of the invention include methods for decreasing a bacterial load of an infecting bacteria in an animal comprising administering a therapeutically effective amount of one or more COX inhibitors to the animal; sometimes these methods can further comprise administering a therapeutically effective amount of one or more antibiotics to the animal. Some embodiments of the invention include methods for decreasing PGE-2 production in an animal comprising administering a therapeutically effective amount of one or more COX inhibitors to the animal; sometimes these methods can further comprise administering a therapeutically effective amount of one or more antibiotics to the animal.

In certain embodiments, the administration of a COX inhibitor takes place not more than about 7 days after exposure, not more than about 72 hours after exposure, not more than about 48 hours after exposure, not more than about 24 hours after exposure, not more than about 18 hours after exposure, not more than about 15 hours after exposure, not more than about 12 hours after exposure, not more than about 9 hours after exposure, not more than about 6 hours after exposure, not more than about 4 hours after exposure, not more than about 3 hours after exposure, not more than about 2 hours after exposure, not more than about 60 minutes after exposure, not more than about 30 minutes after exposure, not more than about 10 minutes after exposure, or not more than about 5 minutes after exposure. In some instances, administration of a COX inhibitor (e.g., a COX-2 inhibitor) post-exposure can be no more than about 1 minute, about 1 minute, about 5 minutes, about 10 minutes, about 30 minutes, about 45 minutes, about 1 hour, about 4 hours, about 6 hours, about 12 hours, about 18 hours, about 24 hours, about 48 hours, about 72 hours, about 4 days, about 5 days, about 6 days, about 7 days, about 8 days, about 9 days, about 10 days, about 11 days, about 12 days, about 1 week, about 2 weeks, about 3 weeks, about 4 weeks, about 2 months, about 6 months, about 9 months, about 1 year, about 2 years, about 5 years, about 10 years or not less than about 10 years, after exposure. In some instances, administration of a COX inhibitor (e.g., a COX-2 inhibitor) prior to exposure can be no more than about 1 hour, about 1 hour, about 4 hours, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 1 week, about 2 weeks, about 3 weeks, about 4 weeks, about 2 months, or not less than 2 months, before exposure. In some instances, the amount of time prior to exposure is informed by the half-life (i.e., the amount of time it takes for the animal's blood plasma concentration of the COX inhibitor to decrease by half) of a COX inhibitor (e.g., a COX-2 inhibitor or a COX-1 inhibitor) being administered; for example, administration of a COX inhibitor (e.g., a COX-2 inhibitor) can be no more than about 1 half-life, about 1 half-life, about 2 half-lives, about 3 half-lives, about 4 half-lives, about 5 half-lives, about 6 half-lives, about 7 half-lives, about 8 half-lives, about 9 half-lives, about 10 half-lives, or about 20 half-lives of the COX inhibitor, before exposure.

In certain embodiments, a COX inhibitor can inhibit one or more activities of one or more isozymes of COX (prostaglandin-endoperoxide synthase) (e.g., COX-1, COX-2, and/or COX-3). In some embodiments, a COX inhibitor can include COX-2 inhibitors, COX-1 inhibitors, or combinations thereof. In some embodiments, the one or more COX inhibitors are selected from but not limited to 4,5-Bis(4-methoxyphenyl-2-[(1-methylpiperazin-4-yl)carbonyl]thiazole, HCl; 4-Amino-(N-(4-cholorophenyl)-N-methyl)benzenesulfonamide); (Methyl [5-methylsulfonyl-1-(4-chlorobenzyl)-1H-2-indolyl]carboxylate); (4-[(5-Difluoromethyl-3-phenyl)-4-isoxazolyl] benzenesulfonamide); (N-(5-Acetyl-2-piperidinophenyl)-N'-(2,5-dichlorophenyl)thiourea); (5-(4-Methoxyphenyl)-3,7-dimethyl-4,5-dihydroisoxazolo[4,5-d]pyridazin-4-one); (4'-Acetyl-2'-(2,4-Difluorophenoxy)methanesulfonanilide); Diclofenac (4'-Hydroxy-(2-R(2',6'-Dichloro-4'-hydroxy) phenyl)amino]benzeneacetic Acid)); Diclofenac Sodium ((2-[(2,6-Dichlorophenyl)amino]benzeneacetic Acid, Sodium)); DuP-697 ((5-Bromo-2-(4-fluorophenyl)-3-(4-(methylsulfonyl)phenyl)thiophene)); Ebselen ((2-Phenyl-1,2-benzisoselenazol-3(2H)-one)); Flurbiprofen ((±)-2-Fluoro-a-methyl[1,1'-biphenyl]-4-acetic Acid)); (±)-Ibuprofen; Indomethacin (1-(p-Chlorobenzoyl)-5-methoxy-2-methyl-1H-indole-3-acetic Acid); Indomethacin Ester (4-Methoxyphenyl-(1-(p-Chlorobenzoyl)-5-methoxy-2-methyl-1H-indole-3-acetic Acid, 4-Methoxyphenyl Ester); Kaempferol ((3,4',5,7-Tetrahydroxyflavone)); MEG Hydrochloride ((Mercaptoethylguanidine, HCl)); Meloxicam ((4-Hydroxy-2-methyl-N-(5-methyl-2-thiazoyl)-2H-1,2-benzothiazine-3-carboxamide-1,1-dioxide)); NS398 ((N-(2-Cyclohexyloxy-4-nitrophenyl)methane sulfonamide; Parthenolide (e.g., from the plant *Tanacetum parthenium*); Pterostilbene, (e.g., from the tree *Pterocarpus marsupium*) (trans-3,5-Dimethoxy-4'-hydroxystilbene); Radicicol (e.g., from the fungus *Diheterospora chlamydosporia*); Resveratrol (trans-3,4',5-Trihydroxystilbene); SC-560 ((5-(4-Chlorophenyl)-1-(4-methoxyphenyl)-3-trifluoromethylpyrazole); Sodium Salicylate; Sulindac Sulfide (((Z)-5-Fluoro-2-methyl-1-[p-(methylthio)benzylidenelindene-3-acetic Acid)); and Sulindac Sulfone (((Z)-5-Fluoro-2-methyl-1-[p-(methylsulfonyl) benzylidene]indene-3-acetic Acid). In other embodiments, the one or more COX inhibitors can be extracts (e.g., using one or more solvents such as, ethanol, water, propanol, methanol or others) of certain organisms such as plants, trees, fungi, including but not limited to *Tribulus terrestris, Tanacetum parthenium, Pterocarpus marsupium*, and *Diheterospora chlamydosporia.*

In other embodiments, the one or more COX inhibitors can be a COX-2 inhibitor selected from but not limited to Lumiracoxib ({2-[(2-chloro-6-fluorophenyl)amino]-5-methylphenyl}acetic acid); Etoricoxib (5-chloro-6'-methyl-3-[4-(methylsulfonyl)phenyl]-2,3'-bipyridine); NS398 ((N-(2-Cyclohexyloxy-4-nitrophenyl)methanesulfonamide; Valdicoxib (4-(5-methyl-3-phenylisoxazol-4-yl)benzenesulfonamide); Roficoxib (4-(4-methylsulfonylphenyl)-3-phenyl-5H-furan-2-one); Etodolac ((RS)-2-(1,8-Diethyl-4,9-dihydro-3H-pyrano [3,4-b]indol-1-yl)acetic acid); Celecoxib (4-[5-(4-methylphenyl)-3-(trifluoromethyl)pyrazol-1-yl] benzenesulfonamide); and Indomethacin (2-{1-[(4-chlorophenyl)carbonyl]-5-methoxy-2-methyl-1H-indol-3-yl}acetic acid.

In still other embodiments, the one or more COX inhibitors can be an NSAID (Non Steroidal Anti Inflammatory Drug). NSAIDs can include but are not limited to Ibuprofen, Aspirin, Ketoprofen, Sulindac, Naproxen, Etodolac, Fenoprofen, Diclofenac, Flurbiprofen, Ketorolac, Piroxicam, Indomethacin, Mefenamic Acid, Meloxicam, Nabumetone, Oxaprozin, Ketoprofen, Famotidine (e.g., in combination with ibuprofen), Meclofenamate, Tolmetin, and Salsalate.

In certain embodiments, the method of treatment (e.g., by administration of the COX inhibitor alone or with antibiotics) results in one or more of (a) reducing PGE-2 production in the animal, (b) decreasing Arg2 expression in the animal, (c) decreasing arginase production in the animal, (d) increasing NO production in the animal (e) increasing leukocyte activation, (f) increasing macrophage microbicidal activity, (g) increasing NK cell function, (h) up-regulation of cell-mediated immunity, (i) lack of weight loss in the animal, or (j) a reduction in the bacterial load of the infecting bacteria. A modulation (e.g., an increase or a decrease) of any of the above in the animal can be a result of such a modulation in one or more organs in the animal. A reduction in PGE-2 production can be, for example, about 5% reduction, about 10% reduction, about 20% reduction, about 30% reduction, about 50% reduction, about 75% reduction, about 80% reduction, about 90% reduction, about 95% reduction, about 99% reduction, about 99.9% reduction, about 99.99% reduction, or about 99.999% reduction. A reduction in bacterial load of the infecting bacteria can be, for example, about 5% reduction, about 10% reduction, about 20% reduction, about 30% reduction, about 50% reduction, about 75% reduction, about 80% reduction, about 90% reduction, about 95% reduction, about 99% reduction, about 99.9% reduction, about 99.99% reduction, about 99.999% reduction, about 99.9999% reduction, or about 99.99999% reduction. A lack of weight loss of the animal can be, for example, any weight gain, zero weight loss, or a weight loss of about 1%, about 2%, about 3%, about 5%, about 6%, about 8%, about 10%, no more than about 10%, no more than about 5%, or no more than about 1%.

In certain embodiments, the one or more antibiotics can be selected from, but are not limited to Aminoglycosides (e.g., Amikacin, Gentamicin, Kanamycin, Neomycin, Netilmicin, Paromomycin, Streptomycin, Tobramycin); Cephalosporins, First Generation (e.g., Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole); Cephalosporins, Second Generation (e.g., Cefaclor, Cefamandole, Cefmetazole, Cefonicid, Cefotetan, Cefoxitin, Cefprozil (cefproxil), Cefuroxime, Cefuzonam); Cephalosporins, Third Generation (e.g., Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime); Cephalosporins, Fourth Generation (e.g., Cefclidine, Cefepime, Cefluprenam, Cefoselis, Cefozopran, Cefpirome, Cefquinome); Cephalosporins, Not Classified (e.g., Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide); Carbapenems (e.g., Imipenem, Imipenem/cilastatin, Doripenem, Meropenem); Quinolone Antibiotics, First Generation (e.g., Flumequine, Nalidixic acid, Oxolinic acid, Piromidic acid, Pipemidic acid, Rosoxacin); Quinolone Antibiotics, Second Generation (e.g., Ciprofloxacin, Enoxacin, Lomefloxacin, Nadifloxacin, Norfloxacin, Ofloxacin, Pefloxacin, Rufloxacin); Quinolone Antibiotics, Third Generation (e.g., Balofloxacin, Gatifloxacin, Grepafloxacin, Levofloxacin, Moxifloxacin, Pazufloxacin, Sparfloxacin, Temafloxacin, Tosufloxacin); Quinolone Antibiotics, Fourth Generation (e.g., Besifloxacin, Clinafloxacin, Gemifloxacin, Sitafloxacin, Trovafloxacin, Prulifloxacin); Macrolide Antibiotics (e.g., Azithromycin, Erythromycin, Clarithromycin, Dirithromycin, Roxithromycin and Ketolides (e.g., Telithromycin)); Penicillins (e.g., Amoxicillin, Ampicillin, Bacampicillin, Carbenicillin, Cloxacillin, Dicloxacillin, Flucloxacillin, Mezlocillin, Nafcillin, Oxacillin, Penicillin G, Penicillin V, Piperacillin, Pivampicillin, Pivmecillinam, Ticarcillin); Sulfonamides (e.g., Sulfamethizole, Sulfamethoxazole, Sulfisoxazole, Trimethoprim-Sulfamethoxazole); Tetracycline Antibiotics (e.g., Demeclocycline, Doxycycline, Minocycline, Oxytetracycline, Tetracycline, and Glycylcyclines (e.g., Tigecycline)); Other Antibiotics (e.g., Vancomycin, Metronidazole, Tinidazole, Nitrofurantoin, Chloramphenicol, and Oxazolidinones (e.g., linezolid, eperezolid, N-((5S)-3-(3-fluoro-4-(4-(2-fluoroethyl)-3-oxopiperazin-1-yl)phenyl)-2-oxooxazolidin-5-ylmethyl)acetamide, (S)—N-[[3-[5-(3-pyridyl)thiophen-2-yl]-2-oxo-5-oxazolidinyl]methyl]acetamide, (S)—N-[[3-[5-(4-pyridyl)pyrid-2-yl]-2-oxo-5-oxazolidinyl]methyl]acetamide hydrochloride and N-[[(5S)-3-[4-(1,1-dioxido-4-thiomorpholinyl)-3,5-difluorophenyl]-2-oxo-5-oxazolidinyl]methyl]acetamide), and Rifamycins (e.g., Rifampin, Rifabutin, Rifapentine), and Lincosamides (e.g., Clindamycin, Lincomycin), and Streptogramins (e.g., Pristinamycin, Quinupristin/dalfopristin); and still other antibiotics (e.g., Lipopeptides, Fluoroquinolone, Lipoglycopeptides, Cephalosporin (5th generation), Macrocyclics).

In certain embodiments, the one or more antibiotics does not include an oxazolidinone drug. In other embodiments, the one or more anitibiotic does not include one or more of (e.g., does not include any of the following) linezolid, eperezolid, N-((5S)-3-(3-fluoro-4-(4-(2-fluoroethyl)-3-oxopiperazin-1-yl)phenyl)-2-oxooxazolidin-5-ylmethyl)acetamide, (S)—N-[[3-[5-(3-pyridyl)thiophen-2-yl]-2-oxo-5-oxazolidinyl]methyl]acetamide, (S)—N-[[3-[5-(4-pyridyl)pyrid-2-yl]-2-oxo-5-oxazolidinyl]methyl]acetamide hydrochloride, or N-[[(5S)-3-[4-(1,1-dioxido-4-thiomorpholinyl)-3,5-difluorophenyl]-2-oxo-5-oxazolidinyl]methyl]acetamide.

An antibiotic or a combination of antibiotics (and their dosages) can be suitably chosen to optimize treatment.

In some instances, administration of the antibiotic post-exposure can be no more than about 1 minute, about 1 minute, about 5 minutes, about 10 minutes, about 30 minutes, about 45 minutes, about 1 hour, about 4 hours, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 1 week, about 2 weeks, about 3 weeks, about 4 weeks, about 2 months, about 6 months, about 9 months, about 1 year, about 2 years, about 5 years, about 10 years or not less than about 10 years, after exposure. In some instances, administration of the antibiotic prior to exposure can be no more than about 1 hour, about 1 hour, about 4 hours, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 1 week, about 2 weeks, about 3 weeks, about 4 weeks, about 2 months, or not less than 2 months, before exposure. In some instances, the amount of time prior to exposure is informed by the half-life (i.e., the amount of time it takes for the animal's blood plasma concentration of the antibiotic to decrease by half) of the antibiotic being administered; for example, administration of the antibiotic can be no more than about 1 half-life, about 1 half-life, about 2 half-lives, about 3 half-lives, about 4 half-lives, about 5 half-lives, about 6 half-lives, about 7 half-lives, about 8 half-lives, about 9 half-lives, about 10 half-lives, or about 20 half-lives of the antibiotic, before exposure.

In some embodiments, the bacterial infectious disease infects one or more of the following animal organs: Brain, Basal ganglia, Brain stem, medulla, Midbrain, pons, Cerebellum, Cerebral cortex, Hypothalamus, Limbic system, Amygdala, Eyes (or tissues of the eyes), Pineal gland, Pituitary gland, Thyroid gland, Parathyroid glands, Heart, Lungs, Esophagus, Thymus gland, Pleura, Adrenal glands, Appendix, Bladder, Gallbladder, Large intestine, Small intestine, Kidneys, Liver, Pancreas, Spleen, Stomach, Prostate gland, Testes, Ovaries, or Uterus. In certain embodiments, bacterial infectious disease infects one or more of lungs, liver, esophagus, stomach, nose, eyes (or tissues of the eyes), sinuses, ear, ear canals, mouth, hands, feet, urethra, or spleen. In certain embodiments, the bacterial infectious disease does not infect an eye, both eyes, tissues of the eyes, combinations thereof, or any of them.

In certain embodiments, the bacteria responsible for the bacterial infectious disease can be, but is not limited to one or more of *Acetobacter aurantius, Acinetobacter baumannii, Actinomyces israelii, Agrobacterium radiobacter, Agrobacterium tumefaciens, Azorhizobium caulinodans, Azotobacter vinelandii, Anaplasma* (e.g., *Anaplasma phagocytophilum*), *Bacillus* (e.g., *Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis*), *Bacteroides* (e.g., *Bacteroides fragilis, Bacteroides gingivalis, Bacteroides melaninogenicus* (now known as *Prevotella melaninogenica*)), *Bartonella* (e.g., *Bartonella henselae, Bartonella quintana*), *Bordetella*

(e.g., *Bordetella bronchiseptica, Bordetella pertussis*), *Borrelia burgdorferi, Brucella* (e.g., *Brucella abortus, Brucella melitensis, Brucella suis*), *Burkholderia* (e.g., *Burkholderia mallei, Burkholderia pseudomallei, Burkholderia cepacia, Burkholderia tailandensis*), *Calymmatobacterium granulomatis, Campylobacter* (e.g., *Campylobacter coli, Campylobacter fetus, Campylobacter jejuni, Campylobacter pylori*), *Chlamydia* (e.g., *Chlamydia trachomatis*), *Chlamydophila* (e.g., *Chlamydophila pneumoniae* (previously called *Chlamydia pneumoniae*), *Chlamydophila psittaci* (previously called *Chlamydia psittaci*), *Clostridium* (e.g., *Clostridium botulinum, Clostridium difficile, Clostridium perfringens* (previously called *Clostridium welchii*), *Clostridium tetani*), *Corynebacterium* (e.g., *Corynebacterium diphtheria, Corynebacterium fusiforme*), *Coxiella burnetii, Ehrlichia chaffeensis, Enterobacter cloacae, Enterococcus* (e.g, *Enterococcus avium, Enterococcus durans, Enterococcus faecalis, Enterococcus faecium, Enterococcus galllinarum, Enterococcus maloratus*), *Escherichia coli, Francisella tularensis, Fusobacterium nucleatum, Gardnerella vaginalis, Haemophilus* (e.g., *Haemophilus ducreyi, Haemophilus influenza, Haemophilus parainfluenzae, Haemophilus pertussis, Haemophilus vaginalis*), *Helicobacter pylori, Klebsiella pneumonia, Lactobacillus* (e.g., *Lactobacillus acidophilus, Lactobacillus bulgaricus, Lactobacillus casei, Lactococcus lactis*), *Legionella pneumophila, Listeria monocytogenes, Methanobacterium extroquens, Microbacterium multiforme, Micrococcus luteus, Moraxella catarrhalis, Mycobacterium* (e.g., *Mycobacterium avium, Mycobacterium bovis, Mycobacterium diphtheria, Mycobacterium intracellulare, Mycobacterium leprae, Mycobacterium lepraemurium, Mycobacterium phlei, Mycobacterium smegmatis, Mycobacterium tuberculosis*), *Mycoplasma* (e.g., *Mycoplasma fermentans, Mycoplasma genitalium, Mycoplasma hominis, Mycoplasma penetrans, Mycoplasma pneumonia*), *Neisseria* (e.g., *Neisseria gonorrhoeae, Neisseria meningitides*), *Pasteurella* (e.g., *Pasteurella multocida, Pasteurella tularensis*), *Peptostreptococcus, Porphyromonas gingivalis, Prevotella melaninogenica* (previously called *Bacteroides melaninogenicus*), *Pseudomonas aeruginosa, Rhizobium radiobacter, Rickettsia* (e.g., *Rickettsia prowazekii, Rickettsia psittaci, Rickettsia quintana, Rickettsia rickettsia, Rickettsia trachomae*), *Rochalimaea* (e.g., *Rochalimaea henselae, Rochalimaea quintana*), *Rothia dentocariosa, Salmonella* (e.g., *Salmonella enteritidis, Salmonella typhi, Salmonella typhimurium, Serratia marcescens*), *Shigella dysenteriae, Shigella flexneri, Staphylococcus* (e.g., *Staphylococcus aureus, Staphylococcus epidermidis*), *Stenotrophomonas maltophilia, Streptococcus* (e.g., *Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumonia, Streptococcus pyogenes, Streptococcus rattus, Streptococcus salivarius, Streptococcus sanguis, Streptococcus sobrinus*), *Treponema* (e.g., *Treponema pallidum, Treponema denticola*), *Vibrio* (e.g., *Vibrio cholera, Vibrio comma, Vibrio parahaemolyticus, Vibrio vulnificus*), *Wolbachia*, or *Yersinia* (e.g., *Yersinia enterocolitica, Yersinia pestis, Yersinia pseudotuberculosis*). In some embodiments, the bacteria responsible for the bacterial infectious disease can be a Gram-negative bacteria. In other embodiments, the bacteria responsible for the bacterial infectious disease can be a Gram-positive bacteria.

In still other embodiments, the bacterial infectious disease can be but is not limited to one or more of the infections (where the infection is not bacterial in nature, the item listed below indicates that secondary bacterial infectious diseases could result) *Acinetobacter* infections, Actinomycosis, Anaplasmosis, Anthrax, *Arcanobacterium haemolyticum* infection, *Ascariasis, Aspergillosis, Babesiosis, Bacillus cereus* infection, Bacterial pneumonia, Bacterial vaginosis (BV), *Bacteroides* infection, *Balantidiasis, Baylisascaris* infection, *Blastocystis hominis* infection, *Blastomycosis, Borrelia* infection, Botulism (and Infant botulism), *Brucellosis, Burkholderia* infection, Buruli ulcer, *Campylobacteriosis*, Cat-scratch disease, Cellulitis, Chagas Disease (American trypanosomiasis), *Chancroid, Chlamydia, Chlamydophila pneumoniae* infection (Taiwan acute respiratory agent or TWAR), *Cholera, Chromoblastomycosis, Clonorchiasis, Clostridium difficile* infection, *Coccidioidomycosis, Cryptococcosis, Cryptosporidiosis, Cutaneous larva migrans* (CLM), *Cyclosporiasis, Cysticercosis, Dientamoebiasis, Diphtheria, Diphyllobothriasis, Dracunculiasis, Echinococcosis, Ehrlichiosis, Enterococcus* infection, *Epidemic typhus, Fasciolopsiasis, Fasciolosis*, Fatal familial insomnia (FFI), Filariasis, Food poisoning by *Clostridium perfringens, Fusobacterium* infection, Gas gangrene (*Clostridial myonecrosis*), *Giardiasis, Glanders, Gnathostomiasis, Gonorrhea, Granuloma inguinale* (Donovanosis), Group A streptococcal infection, Group B streptococcal infection, *Haemophilus* influenzae infection, *Helicobacter pylori* infection, Hemolytic-uremic syndrome (HUS), HIV, Human ewingii ehrlichiosis, Human granulocytic anaplasmosis (HGA), Human monocytic ehrlichiosis, Hymenolepiasis, Isosporiasis, Kawasaki disease, Keratitis, *Kingella kingae* infection, Kuru, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Malaria, Melioidosis (Whitmore's disease), Meningitis, Meningococcal disease, Metagonimiasis, Microsporidiosis, Murine typhus (Endemic typhus), *Mycoplasma pneumonia*, Mycetoma, Myiasis, Neonatal conjunctivitis (Ophthalmia neonatorum), Nocardiosis, Onchocerciasis (River blindness), Paracoccidioidomycosis (South American blastomycosis), Paragonimiasis, Pasteurellosis, Pelvic inflammatory disease (PID), Pertussis (Whooping cough), Plague, Pneumococcal infection, *Pneumocystis pneumonia* (PCP), Pneumonia, *Prevotella* infection, Primary amoebic meningoencephalitis (PAM), Psittacosis, Q fever, Rat-bite fever, Rhinosporidiosis, Rickettsial infection, Rickettsialpox, Rocky mountain spotted fever (RMSF), Salmonellosis, Scabies, Schistosomiasis, Sepsis, Shigellosis (Bacillary dysentery), Sporotrichosis, *Staphylococcal* food poisoning, *Staphylococcal* infection, Strongyloidiasis, Syphilis, Taeniasis, Tetanus (Lockjaw), Trichinellosis, Tuberculosis, Tularemia, Ureaplasma urealyticum infection, *Yersinia pseudotuberculosis* infection, Yersiniosis, or Zygomycosis. In certain embodiments, the bacterial infectious disease is a *Burkholderia* infection (e.g., due to *Burkholderia pseudomallei, Burkholderia mallei, Burkholderia cepacia, Burkholderia cepacia complex, Burkholderia thailandensis*), tuberculosis (e.g., due to *Mycobacterium tuberculosis*), or an infection due to *Francisella tularensis, Klebsiella pneumonia, Pseudomonas aeruginosa*, or *Shigella flexneri.*

In some embodiments, the bacterial infectious disease can be a mucosal bacterial infection (e.g., a bacterial infection of a mucous membrane). For example, a mucosal bacterial infection can be a *Burkholderia* infection, a *Mycobacterial* infection, an *Enterococcus* infection, melioidosis, or tuberculosis. In certain instances, a mucosal bacterial infection can be caused by any of the bacteria disclosed herein. In certain embodiments, the mucosal bacterial infection can be caused by *Burkholderia pseudomallei, Burkholderia mallei, Burkholderia thailandensis, Mycobacterium tuberculosis, Francisella tularensis, Pseudomonas aeruginosa, Klebsiella pneumoniae, Salmonella*, or *Shigella flexneri.*

In certain embodiments, the bacteria responsible for the bacterial infectious disease can be, but is not limited to one or more of a multidrug-resistant strain of bacteria including, but not limited to, *Burkholderia pseudomallei*, Methicillin-resistant *Staphylococcus aureus* (Methicillin-RSA), Vancomycin-Resistant *Enterococcus* (VRE), and Linezolid-Resistant *Enterococcus* (LRE). In some embodiments, the bacteria can be a drug-resistant or multidrug-resistant strain of *Burkholderia pseudomallei, Bacillus subtilis, Escherichia coli, Pseudmonadas aeruginosa, Mycobacterium vaccae, Sporobolomyces salmonicolor, Candida albicans, Penicilluum notatum*, and *Mycobacterium tuberculosis*. In certain instances, the multidrug-resistant or drug-resistant strain of bacteria can cause an increase in PGE-2 production in the infected animal. Thus, in certain embodiments, methods of using one or more COX inhibitors described herein (plus optionally an antibiotic) may be provided for the treatment of an infection from a drug-resistant strain or multidrug-resistant strain of bacteria.

In other embodiments, the untreated bacterial infectious disease can result in death to the animal in an average timeframe of about 30 days, about 20 days, about 10 days, about 5 days, about 4 days, about 3 days, about 2 days, about 1 day, about 18 hours, about 12 hours, about 6 hours, about 3 hours, about 2 hours, or about one hour.

In some instances, the bacterial infectious disease does not respond to an antibiotic(s)-only treatment, which can be displayed as one or more of (but not limited to) the following (a) the animal is unable to recover from the infection, (b) the animal dies from the infection, (c) the bacterial load of the infecting bacteria in the animal does not decrease in about 24 hour or in about 48 hours by about 1%, about 5%, about 10%, about 15%, about 20%, about 30%, about 40%, about 50%, about 90%, about 98%, or about 99%. In certain embodiments, the bacterial infectious disease (when untreated or, in some instances, when treated by one or more antibiotics only) can result in one or more of (a) increasing PGE-2 production in the animal, (b) increasing Arg2 expression in the animal, (c) increasing arginase production in the animal, (d) decreasing NO production in the animal (e) decreasing leukocyte activation, (f) decreasing macrophage microbicidal activity, (g) decreasing NK cell function, (h) down-regulation of cell-mediated immunity, (i) weight loss in the animal, or (j) an increase in the bacterial load of the infecting bacteria. A modulation (e.g., an increase or a decrease) of any of the above in the animal can be a result of such a modulation in one or more organs in the animal. Weight loss of the animal can be, for example, a weight loss of about 1%, about 2%, about 3%, about 5%, about 6%, about 8%, about 10%, about 20%, about 25%, about 30%, about 40%, about 50%, more than about 5%, more than about 10%, more than about 25%, or more than about 40%.

The term "exposed" or "exposure" means that the animal was subjected to an environment and/or an event that could result in being infected. Such exposures can be, but are not limited to, direct or indirect contact with or nearness to (e.g., sharing the same room, space, pen, instrument, furniture, food, or utensils) an infected person, accidental dissemination or release of biological agents (e.g., from a research laboratory, from a farm, from waste processing, from food processing), a bioterrorism event (e.g., from dissemination, deployment, release, or production of a biological agent), a civilian training event, a military training event, a battlefield event (e.g., from dissemination, deployment, release, or production of a biological agent), a medical procedure, a surgical procedure, or a health-related procedure. An exposed animal may or may not ultimately contract the infectious disease. An exposed animal may or may not have, in fact, come into direct contact or indirect contact with one or more contagions. Exposure can be through any means including but not limited to, contact with skin (e.g., broken skin or abraded skin), contact with blood or a bodily fluid (e.g., via an open sore or cut), injection, inhalation, ingestion, or contact with mucous membrane. In some instances a mucous membrane is a membrane that secretes mucin and that lines a bodily cavity and/or canal that lead to the outside of the body; examples include but are not limited to cavities and/or canals in the respiratory, digestive, and urogenital tracts, and these cavities and/or canals include but are not limited to the mouth, eyes, nose, eyelids, windpipe and lungs, stomach and intestines, and the ureters, urethra, and urinary bladder. "Post-exposure" means any time that is after exposure has occurred (e.g., any time from one microsecond to seconds, minutes, hours, days, weeks, months, or years after exposure). In some instances, administration post-exposure can be no more than about 1 minute, about 1 minute, about 5 minutes, about 10 minutes, about 30 minutes, about 45 minutes, about 1 hour, about 4 hours, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 1 week, about 2 weeks, about 3 weeks, about 4 weeks, about 2 months, about 6 months, about 9 months, about 1 year, about 2 years, about 5 years, about 10 years or not less than about 10 years, after exposure. "Prior to exposure" means any time that is before exposure has occurred (e.g., any time from one microsecond to seconds, minutes, hours, days, weeks, or months, or years before exposure). In some instances, administration prior to exposure can be no more than about 1 hour, about 1 hour, about 4 hours, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 1 week, about 2 weeks, about 3 weeks, about 4 weeks, about 2 months, or not less than 2 months, before exposure. In some instances, the amount of time prior to exposure is informed by the half-life (i.e., the amount of time it takes for the animal's blood plasma concentration of the drug to decrease by half) of the drug (e.g., a COX-2 inhibitor, a COX-1 inhibitor, or an antibiotic) being administered; for example administration can be no more than about 1 half-life, about 1 half-life, about 2 half-lives, about 3 half-lives, about 4 half-lives, about 5 half-lives, about 6 half-lives, about 7 half-lives, about 8 half-lives, about 9 half-lives, about 10 half-lives, or about 20 half-lives of the drug, before exposure.

"Therapeutically effective amount" of a COX inhibitor means an amount effective to achieve a desired and/or beneficial effect. A therapeutically effective amount can be administered in one or more administrations. For some purposes of this invention, a therapeutically effective amount is an amount appropriate to treat an infectious disease. By treating an infectious disease is meant achieving any desirable effect, such as one or more of palliate, ameliorate, stabilize, reverse, slow, or delay disease progression, increase the quality of life, or to prolong life. Such achievement can be measured by any method known in the art, such as measurement of PGE-2 production, Arg2 expression, bacterial load, the level of relevant antigens in blood serum, or measuring animal (e.g., a human patient) life. In some instances, the therapeutically effective amount can depend on many factors, including but not limited to the species, age, weight, specifics of the bacterial infection, specifics of the animal's physiology (e.g., immune system or state of health), or combinations thereof.

"Therapeutically effective amount" of an antibiotic means an amount effective to achieve a desired and/or beneficial effect. A therapeutically effective amount can be administered in one or more administrations. For some purposes of this invention, a therapeutically effective amount is an amount appropriate to treat an infectious disease. By treating an infectious disease is meant achieving any desirable effect, such as one or more of palliate, ameliorate, stabilize, reverse, slow, or delay disease progression, increase the quality of life, or to prolong life. Such achievement can be measured by any method known in the art, such as measuring bacterial load, measuring body temperature, monitoring of the level of relevant antigens in blood serum, or measuring animal (e.g., a human patient) life. In some instances, the therapeutically effective amount can depend on many factors, including but not limited to the species, age, weight, specifics of the bacterial infection, specifics of the animal's physiology (e.g., immune system or state of health), or combinations thereof.

Some embodiments of the invention can include methods of treating an animal. In some embodiments, the animal is a mammal, for example, but not limited to, a human, rodent (e.g., mice or rats), horse, dog, cat, pig, cow, or goat. In some embodiments, the mammal is a human. In other embodiments, the animal is in need of treatment for a disease, condition, or disorder related to an infectious disease (e.g., a bacterial infectious disease). In certain embodiments, a human is in need of the treatment for a disease, condition, or disorder related to an infectious disease (e.g., a bacterial infectious disease). For example, an animal (e.g., a human) in need thereof can include but is not limited to an animal (e.g., human) that was exposed to a bacterial infectious disease, that could in the future be exposed to a bacterial infectious disease, that displays symptoms of a bacterial infectious disease, or that is diagnosed with a bacterial infectious disease.

In some embodiments of the methods of the invention, the treating of an animal may occur in any manner of administration (e.g., for a COX inhibitor or for an antibiotic), including, but not limited to oral treatment (e.g., via pill or liquid), inhalation, aerosol, intranasal treatment, topical administration, or injection. For example, injection may include, but is not limited to, intravenous, intraperitoneal, intramuscular, or subcutaneous injection. Administration by inhalation (e.g., for a COX inhibitor or for an antibiotic), in some instances, can be delivered using an aerosol spray in the form of solution, dry powder, or cream. The aerosol can use, for example, a pressurized pack or a nebulizer and a suitable propellant. In the case of a pressurized aerosol, the dosage unit can be controlled by providing a valve to deliver a metered amount. Capsules and cartridges of, for example, gelatin for use in an inhaler may be formulated containing a power base such as lactose or starch. In other embodiments (e.g., for a COX inhibitor or for an antibiotic), the manner of administration (e.g., for a COX inhibitor or for an antibiotic) does not include topical administration. In additional embodiments, the manner of administration (e.g., for a COX inhibitor or for an antibiotic) does not include topical administration to an eye (e.g., with eye drops, creams, or gels). In still other embodiments, the manner of administration (e.g., for a COX inhibitor or for an antibiotic) does not include topical administration to an eye, but may include treatment of the eye by systemic administration (e.g., by pill or inhalation). In still other embodiments, treatment (e.g., by a COX inhibitor or by an antibiotic) does not include treatment of the eye.

In certain embodiments the methods of treating an animal can include treatment with an amount of a COX inhibitor (e.g., a COX-1 inhibitor or a COX-2 inhibitor) that is effective to treat the disease that the animal has or is suspected of having, or to bring about a desired physiological effect. In some embodiments, the amount of a COX inhibitor (i.e., a COX inhibitor which is one of the one or more COX inhibitors) is administered at a concentration of about 0.05 to about 800 mg/kg body weight, about 0.05 to about 200 mg/kg body weight, about 0.2 to about 40 mg/kg body weight, about 0.5 to about 20 mg/kg body weight, about 0.01 mg/kg, about 0.02 mg/kg, about 0.05 mg/kg, about 0.08 mg/kg, about 0.1 mg/kg, about 0.15 mg/kg, about 0.2 mg/kg, about 0.25 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.2 mg/kg, about 1.4 mg/kg, about 1.6 mg/kg, about 1.8 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 12.0 mg/kg, about 14.0 mg/kg, about 16.0 mg/kg, about 18.0 mg/kg, about 20.0 mg/kg, about 25.0 mg/kg, about 30.0 mg/kg, about 40.0 mg/kg, about 50.0 mg/kg, about 60.0 mg/kg, about 70.0 mg/kg, about 80.0 mg/kg, about 90.0 mg/kg, about 100.0 mg/kg, about 125.0 mg/kg, about 150.0 mg/kg, about 175.0 mg/kg, about 200.0 mg/kg, about 300.0 mg/kg, about 400.0 mg/kg, about 600.0 mg/kg, or about 800.0 mg/kg. In regard to some conditions, the dosage can be about 15 mg/kg body weight, about 75 mg/kg body weight, or about 200 mg/kg body weight. In some embodiments, the amount of a COX inhibitor (i.e., a COX inhibitor which is one of the one or more COX inhibitors) is administered at an amount of from about 0.05 to about 50 g, from about 1 mg to about 10 g, from about 10 mg to about 1 g, about 0.05 mg, about 0.1 mg, about 0.2 mg, about 0.5 mg, about 1 mg, about 1.5 mg, about 2 mg, about 5 mg, about 10 mg, about 20 mg, about 50 mg, about 100 mg, about 200 mg, about 500 mg, about 1 g, about 2 g, about 5 g, about 10 g, about 20 g, about 30 g, or about 50 g. For instance, one or more doses (e.g., 1, 2, 3, 4, or 5 doses) can be administered in a 24 hour period or at any suitable interval. The aforementioned administration amounts and dosages of a COX inhibitor are examples of therapeutically effective amounts of a COX inhibitor.

In certain embodiments, the dosage of a COX inhibitor can be higher compared to a dosage a COX inhibitor for long term usage (e.g., weeks, months, years, or for the rest of one's life). In some embodiments, the dosage can be higher than one or more long term usage dosages by at about 2 fold, at least about 5 fold, at least about 10 fold, about 1.5 fold, about 2 fold, about 3 fold, about 4 fold, about 5 fold, about 6 fold, about 7 fold, about 8 fold, about 9 fold, about 10 fold, about 20 fold, about 40 fold, about 50 fold, about 75 fold, about 100 fold, or more than about 100 fold. The term "fold" is meant to indicate a multiplicative factor; for example, a dosage that is 2 fold higher than a long term dosage of 325 mg is calculated by multiplying by 2 to yield a dosage of 650 mg (i.e., 2 times the long term dosage). Long term usage dosages of COX inhibitors include, for example, dosages of a COX inhibitor used for extended periods of time (e.g., weeks, months, years, or for the rest of one's life) to treat diseases that can indicate such long term usage dosage regimes such as, but not limited to osteoarthritis, rheumatoid arthritis, or an injury (e.g., a sports injury). The aforementioned dosages of a COX inhibitor are examples of therapeutically effective amounts of a COX inhibitor.

Table 1 shows some Cox-2 inhibitors and some examples of long term dosages.

TABLE 1

| Generic Name | Brand Name | Source | Human Dose Used | Route of Administration |
|---|---|---|---|---|
| Lumiracoxib | Prexige | Novartis | 50 mg, 100 mg, and 400 mg | oral |
| Etoricoxib | Arcoxia | Merck | | oral |
| Valdicoxib | Bextra | Pfizer | 40 mg tab 2× day | oral |
| Roficoxib | Vioxx | Pfizer | 12.5 mg, 25 mg, 50 mg tabs 2× day | oral |
| Etodolac | Lodine | Wyeth, Possibly Pfizer | 200 mg, 300 mg, 400 mg, 500 mg and 600 mg capsules 2× day | oral |
| Celecoxib | Celebrex | Pfizer | 200 mg and 400 mg capsules 2× day | oral |
| Indomethacin | Indocin | | 25 mg, 50 mg, 75 mg, 150 mg, 200 mg | oral |

It is possible to employ many concentrations and/or dosage regimes in the methods of the present invention. Adjusting and testing any number of concentrations and/or dosage regimes can be used in order to find one that achieves the desired result in a given circumstance. Moreover, some embodiments of the methods of the invention can include administration of one or more other therapeutic agents, including but not limited to antibiotics. In other embodiments, no antibiotics are administered.

In certain embodiments the methods of treating an animal can include treatment (e.g., in combination with one or more COX inhibitors) with an amount of an antibiotic (i.e., the antibiotic may be one of the one or more antibiotics) that is effective to treat the disease that the animal has, or is suspected of having, or to bring about a desired physiological effect. In some embodiments, the amount of an antibiotic is administered at a concentration of about 0.05 to about 200 mg/kg body weight, about 0.2 to about 40 mg/kg body weight, about 0.5 to about 20 mg/kg body weight, about 0.01 mg/kg, about 0.02 mg/kg, about 0.05 mg/kg, about 0.08 mg/kg, about 0.1 mg/kg, about 0.15 mg/kg, about 0.2 mg/kg, about 0.25 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.2 mg/kg, about 1.4 mg/kg, about 1.6 mg/kg, about 1.8 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 12.0 mg/kg, about 14.0 mg/kg, about 16.0 mg/kg, about 18.0 mg/kg, about 20.0 mg/kg, about 25.0 mg/kg, about 30.0 mg/kg, about 40.0 mg/kg, about 50.0 mg/kg, about 60.0 mg/kg, about 70.0 mg/kg, about 80.0 mg/kg, about 90.0 mg/kg, about 100.0 mg/kg, about 125.0 mg/kg, about 150.0 mg/kg, about 175.0 mg/kg, about 200.0 mg/kg, about 300.0 mg/kg, or about 400.0 mg/kg. In regard to some conditions, the dosage can be about 15 mg/kg, about 25 mg/kg, or about 60 mg/kg body weight. In some embodiments, the amount of an antibiotic is administered at an amount of from about 0.1 mg to about 10 g, from about 1 mg to about 5 g, from about 10 mg to about 1 g, about 0.1 mg, about 0.2 mg, about 0.5 mg, about 1 mg, about 1.5 mg, about 2 mg, about 5 mg, about 10 mg, about 20 mg, about 50 mg, about 100 mg, about 200 mg, about 500 mg, about 1 g, about 2 g, about 3 g, about 4 g, about 5 g, about 8 g, or about 10 g. For instance, one or more doses (e.g., 1, 2, 3, 4, or 5 doses) can be administered in a 24 hour period or at any suitable interval. It is possible to employ many concentrations and/or dosage regimes in the methods of the present invention. Adjusting and testing any number of concentrations and/or dosage regimes can be used in order to find one that achieves the desired result in a given circumstance. In some embodiments, an antibiotics can be administered within about zero minutes, within about 5 minutes, within about 10 minutes, within about 20 minutes, within about 30 minutes, within about 60 minutes, within about 90 minutes, within about 120 minutes, within about 3 hours, within about 4 hours, within about 5 hours, within about 10 hours, within about 15 hours, within about 24 hours, within about 36 hours, within about 48 hours, within about 50 hours, within about 3 days, within about 4 days, within about 5 days, within about 1 week, or within about 2 weeks of one or more of the administrations of a Cox inhibitor. Moreover, some embodiments of the methods of the invention can include administration of one or more additional therapeutic agents, at any timing specified herein for a COX inhibitor or for an antibiotic. The aforementioned are examples of therapeutically effective amounts of an antibiotic.

EXAMPLE SET A

Example A1—*Burkholderia thailandensis* (Bt) and Bps Induce PGE-2 Production in a Time and Dose-Dependent Manner

*Burkholderia pseudomallei* can induce cell death known as pyroptosis in macrophages as early as eight hours post infection at a multiplicity of infection (MOI) of 10:1 or greater. In pilot experiments, J774 macrophages infected with Bt at MOI 10:1 or 1:1 displayed 80% and 28% cytotoxicity, respectively at eight hours post-infection. Therefore, experiments utilizing primary BMDM or macrophage cell lines were limited to an eight hour experimental time course using *Burkholderia* at MOI 1:1 or lower (1:10).

Figure 1:
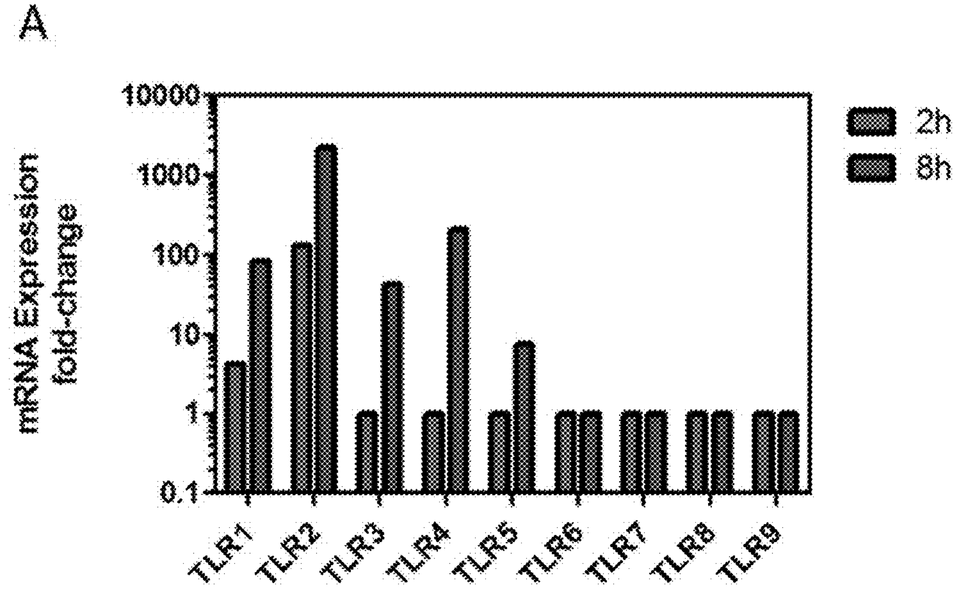
FIG. 1A and FIG. 1B show mRNA expression fold-change in responses to *Burkholderia thailandensis* (Bt) infection of macrophages.
Figure 1:
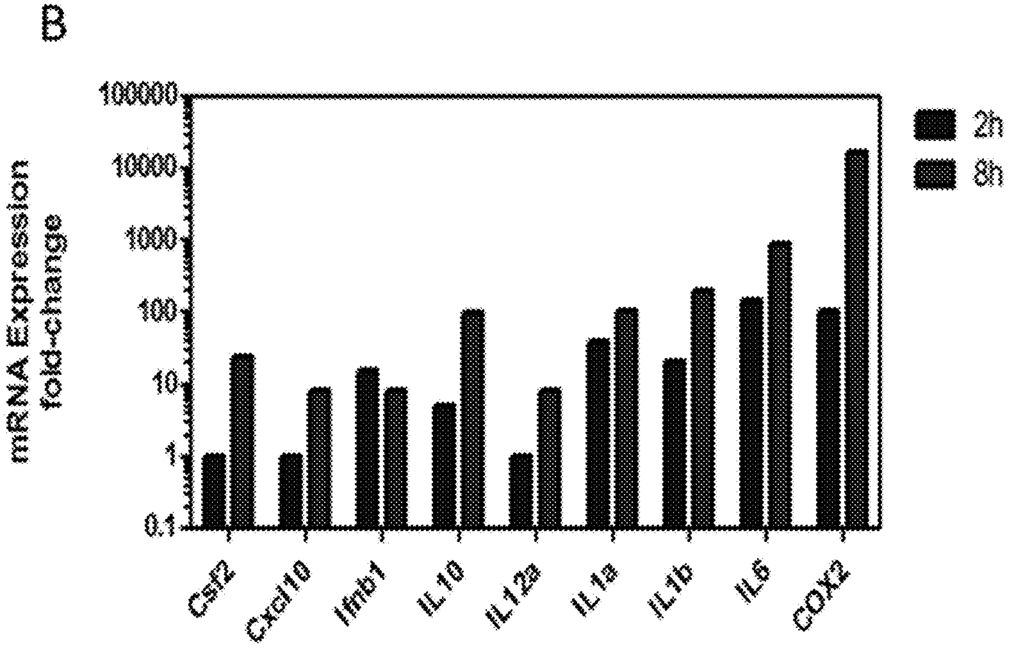

In order to elucidate innate immune responses to *Burkholderia* infection, a TLR PCR array was performed on J774A-1 macrophages infected with Bt. Consistent with previous reports, Bt upregulated expression of TLR1 and TLR2 by two hours post-infection, and increases in TLR1, TLR2, TLR3, TLR4, and TLR5 mRNA expression were observed by eight hours post-infection, as shown in FIG. 1A. No change in mRNA expression was observed for TLR6, TLR7, TLR8, or TLR9. Cox-2 mRNA expression increased more than 10,000 fold by eight hours post-infection with Bt, as shown in FIG. 1B.

To confirm the PCR array, macrophages were infected with Bt and Bps, and supernatants were harvested for measurement of PGE-2 concentration. At four and eight hours post-infection, the levels of PGE-2 were increased in macrophages infected with Bt at MOI 1:1 compared to macrophages infected with Bt at MOI 1:10 and uninfected cells, as shown in FIG. 2A.

Figure 2:
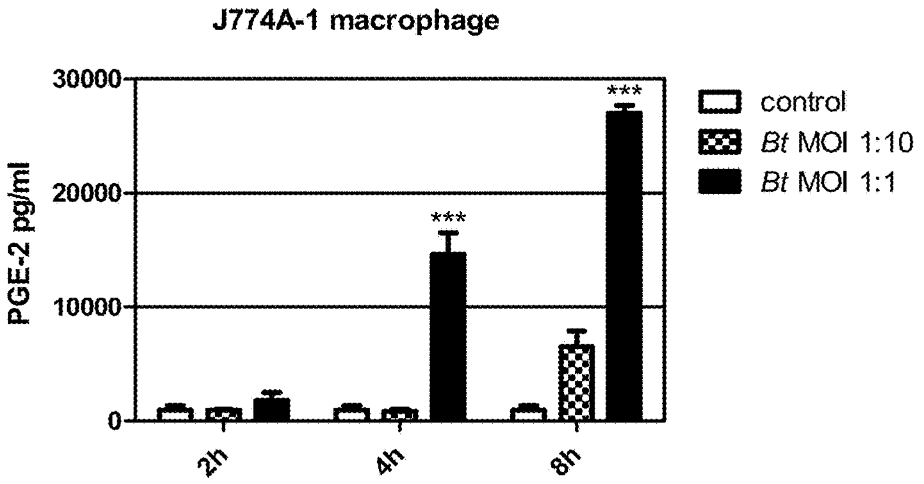
FIG. 2 shows PGE-2 concentration levels in supernatants harvested from macrophages infected with *Burkholderia thailandensis* and *Burkholderia pseudomallei* (Bp). (A) Levels of PGE-2 at two, four, and eight hours post-infection in J774A-1 macrophages infected with Bt; (B) PGE-2 levels at two, four, and six hours post-infection of bone marrow derived macrophages (BMDM) with Bp; and (C) PGE-2 levels at eight and 24 hours post-infection in A549 human lung alveolar epithelial cells in response to Bt infection. *$p<0.05$, $p<0.01$, *$p<0.001$.
Figure 2:
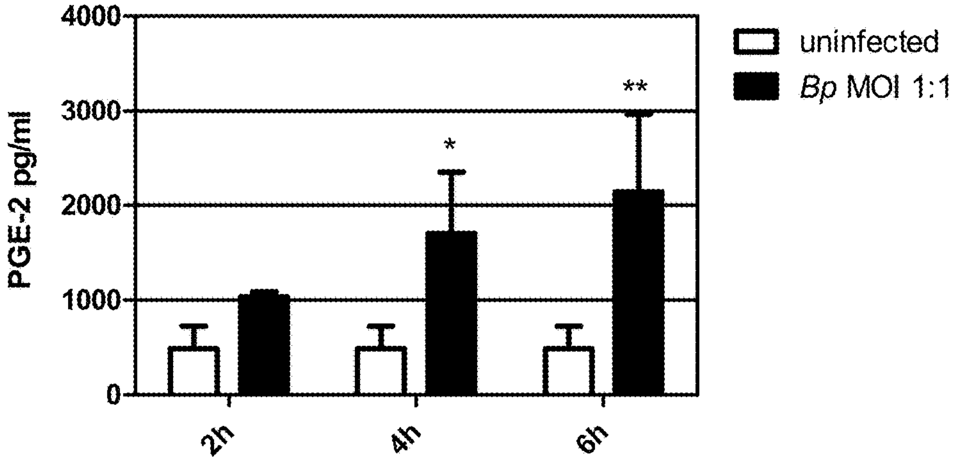
Figure 2:
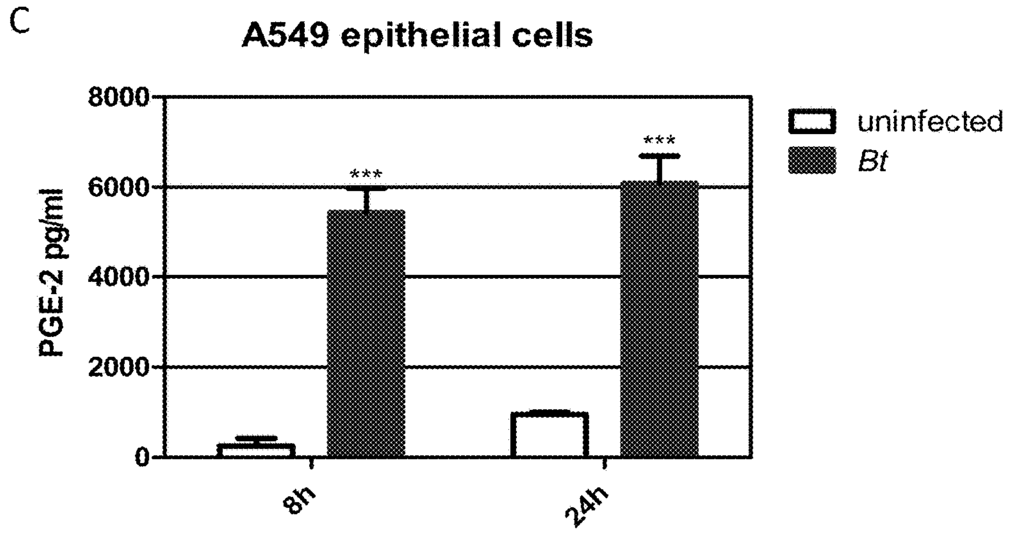

Upon infection of BMDM with Bps, PGE-2 levels were also increased at four and six hours post-infection, as shown in FIG. 2B. In addition, human lung alveolar epithelial cells (A549) produced high levels of PGE-2 in response to Bt after eight and 24 hours of infection, as shown in FIG. 2C, indicating that the response is not restricted to the mouse macrophage.

Example A2—Endogenous PGE-2 Enhances Intracellular Survival of Bt and Bp

The influence of PGE-2 on *Burkholderia* intracellular survival was assessed. J774A-1 macrophages pre-treated with NS398 (a selective Cox-2 inhibitor) demonstrated enhanced intracellular killing of Bt, as evidenced by a decrease in survival of intracellular bacteria compared to non-treated cells six hours post-infection, shown in FIG. 3A.

Figure 3:
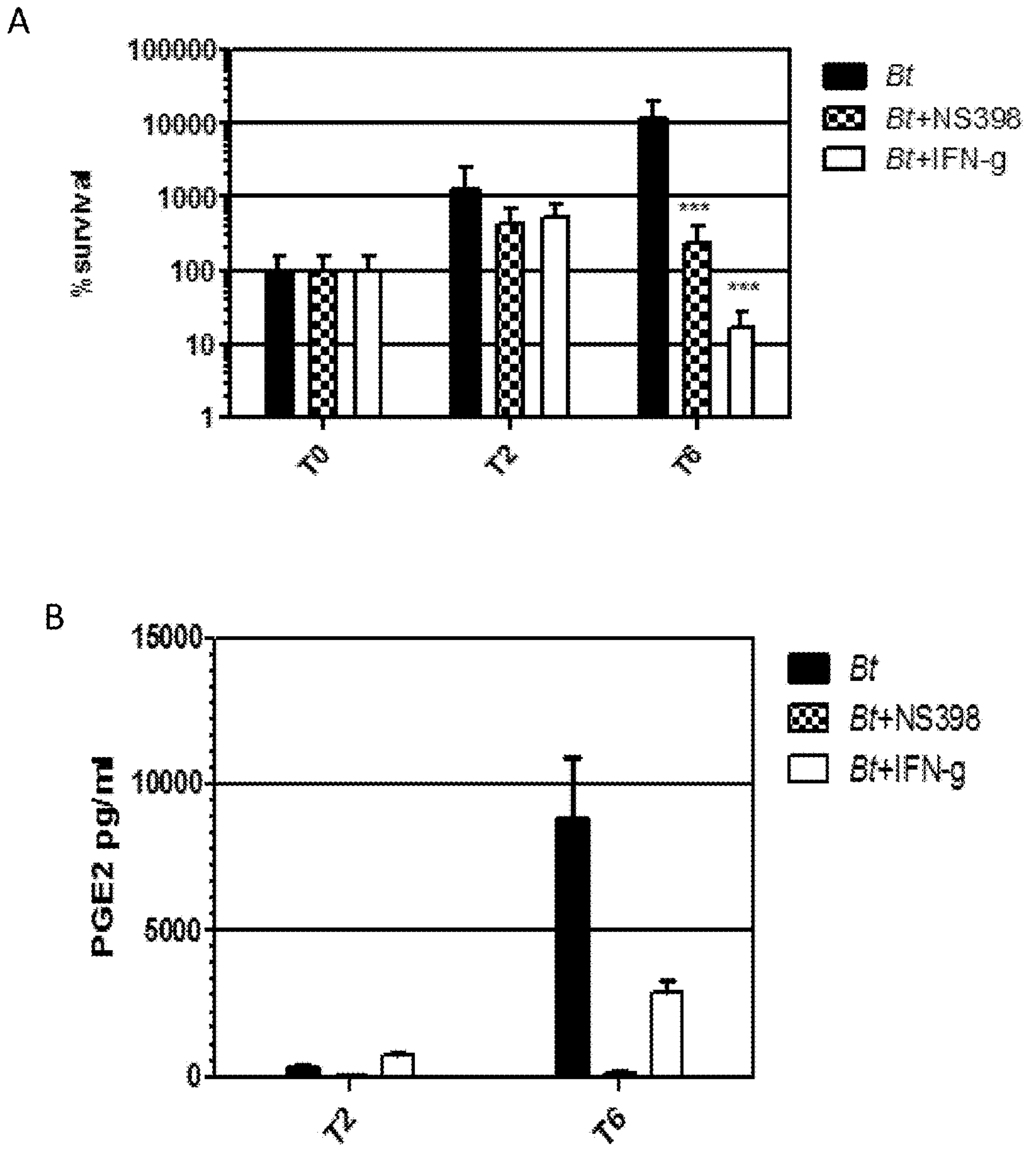
FIG. 3 shows an assessment of the influence of PGE-2 on *Burkholderia intracellular* survival. (A) Bt survival in J774A-1 macrophages pre-treated with NS398 (a selective Cox-2 inhibitor); (B) PGE-2 levels measured in the supernatants of NS398-treated and non-treated macrophages; and (C) Bps survival six hours post-invasion after pre-treatment of BMDM with NS398 with or without the addition of 1 μM of exogenous PGE-2 to the Cox-2 inhibitor pre-treated cells. *$p<0.001$
Figure 3:
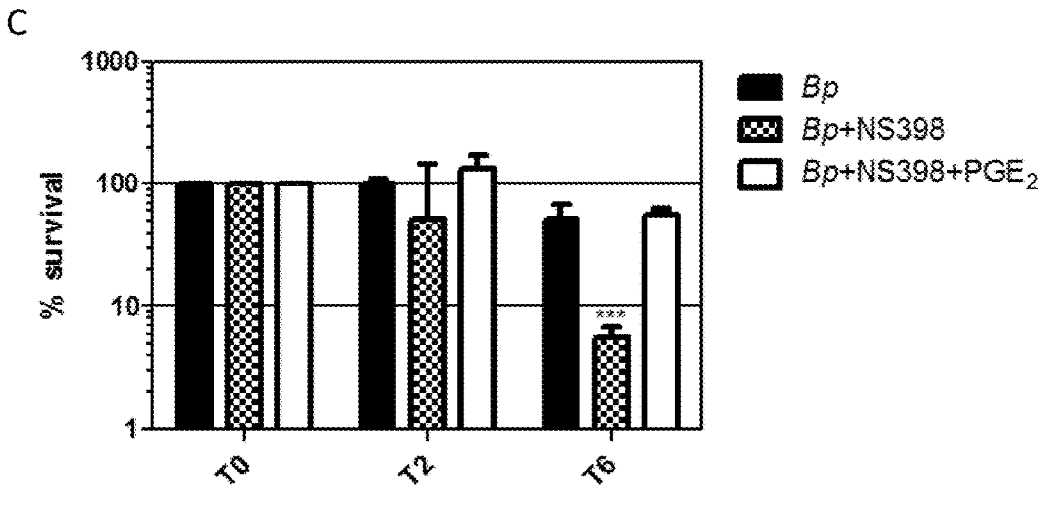

To verify that endogenous PGE-2 is responsible for the suppression of bacterial killing, PGE-2 levels were measured in the supernatants of NS398-treated and non-treated macrophages. PGE-2 levels were reduced in cells treated with NS398, as shown in FIG. 3B. Similar to that observed with Bt, pre-treatment of BMDM with NS398 led to a reduction in Bps survival six hours post-invasion, as shown in FIG. 3C. The suppression of Bps growth by NS398 was abrogated when 1 μM of exogenous PGE-2 was added to the Cox-2 inhibitor pre-treated cells, also shown in FIG. 3C. These results demonstrate a decline in *Burkholderia's* intracellular survival after inhibiting endogenous PGE-2 production.

Figure 4:
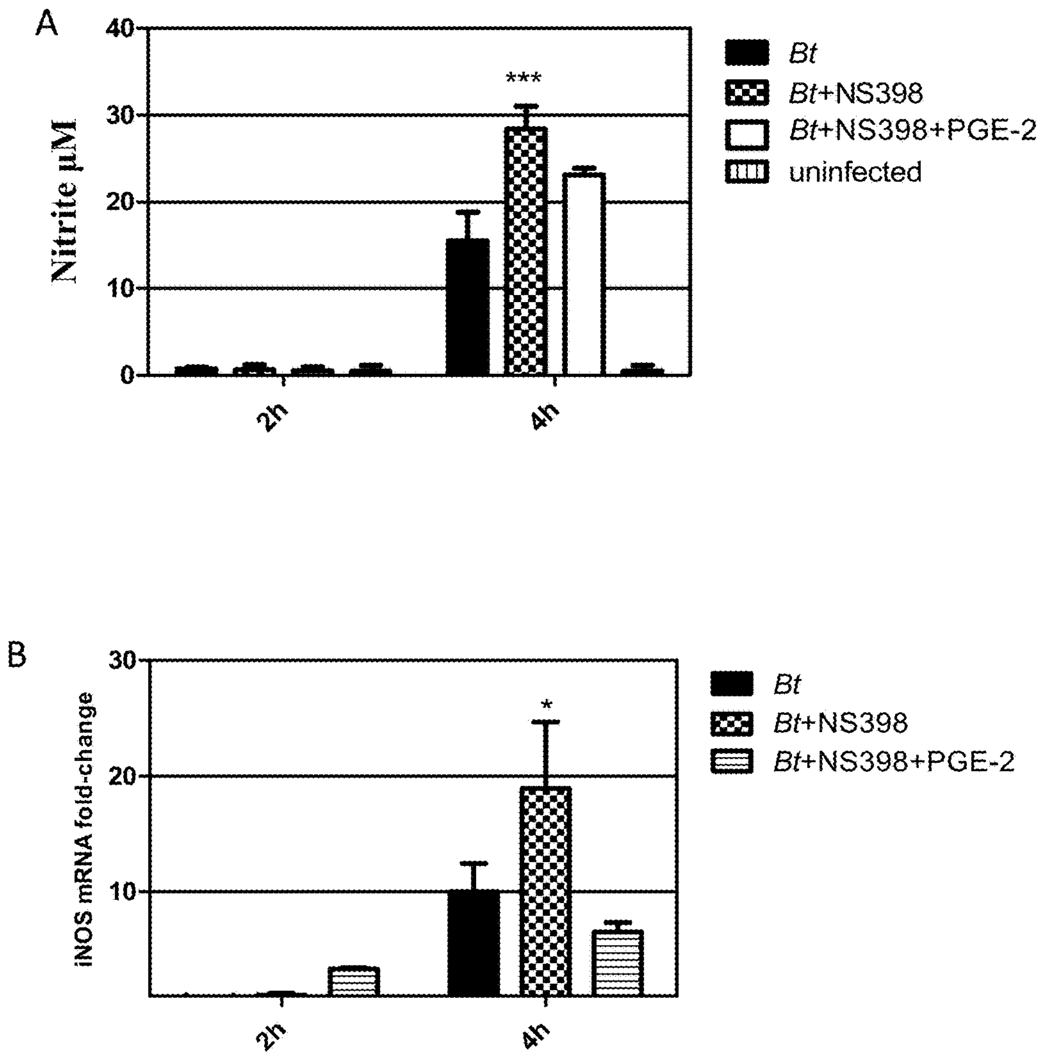
FIG. 4** shows the effect of PGE-2 on NO in response to Bt and Bps infection. (A) NO (B) iNOS levels observed after two and four hours post-infection in BMDM, after pre-treatment of macrophages with the Cox-2 inhibitor NS398 and after the addition of 1 μM PGE-2 to NS398-treated macrophages infected with Bt; (C) Arg1 and Arg2 mRNA levels four hours post-exposure to Bps. *$p<0.05$*$p<0.001$
Figure 4:
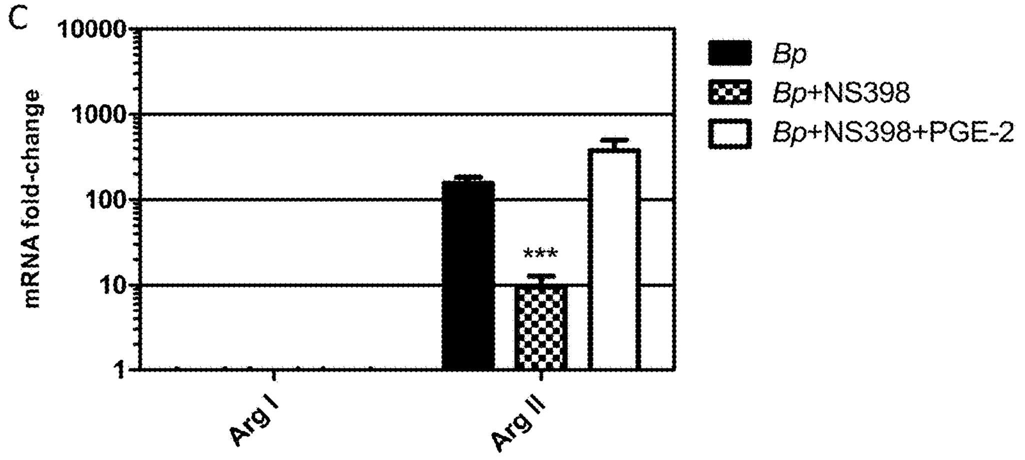

Example A3—PGE-2 Suppresses Nitric Oxide Generation and Induces Arginase Expression PGE-2 has been shown to suppress NO levels. Therefore, the downstream effect of PGE-2 on NO in response to Bt and Bps infection was evaluated. NO was determined using the Griess assay which measures nitrite, the stable end product of NO. A statistically significant increase in NO levels were observed in BMDM infected with Bt and Bps by four and six hours post-infection, respectively, as shown in FIGS. 4A and 4B. Pre-treatment of macrophages with the Cox-2 inhibitor NS398 resulted in higher production of NO, while the addition of 1 μM PGE-2 to NS398-treated macrophages reduced NO levels, also shown in FIGS. 4A and 4B. This indicates that PGE-2 is suppressing NO production in macrophages infected with Bps or Bt.

The effect of endogenous PGE-2 production on the expression of iNOS, which is required for the synthesis of NO, was examined. A two-fold increase in iNOS expression in Bt infected cells after treatment with NS398 was observed, as shown in FIG. 4B. However, no differences in iNOS mRNA expression in NS398-treated or PGE-2-treated cells infected with Bps were observed (data not shown).

Since arginase competes with iNOS for L-arginine, PGE-2 induction of arginase could alter the level of NO production during *Burkholderia* infection. Arg1 expression was not detected after four hours of infection, but the expression of Arg2 was increased in Bt-infected BMDM. This was confirmed in Bps-infected BMDM, which demonstrated a 155-fold increase in Arg2 expression after four hours. NS398 pre-treated macrophages demonstrated a reduction in Arg2 expression, while treatment with exogenous PGE-2 led to a 376-fold increase in Arg2 expression, as shown in FIG. 4C. These data suggest that endogenous PGE-2 may interfere with NO production by enhancing Arg2 expression.

Example A4—Arginase Enhances *Burkholderia intracellular* Survival

Figure 5:
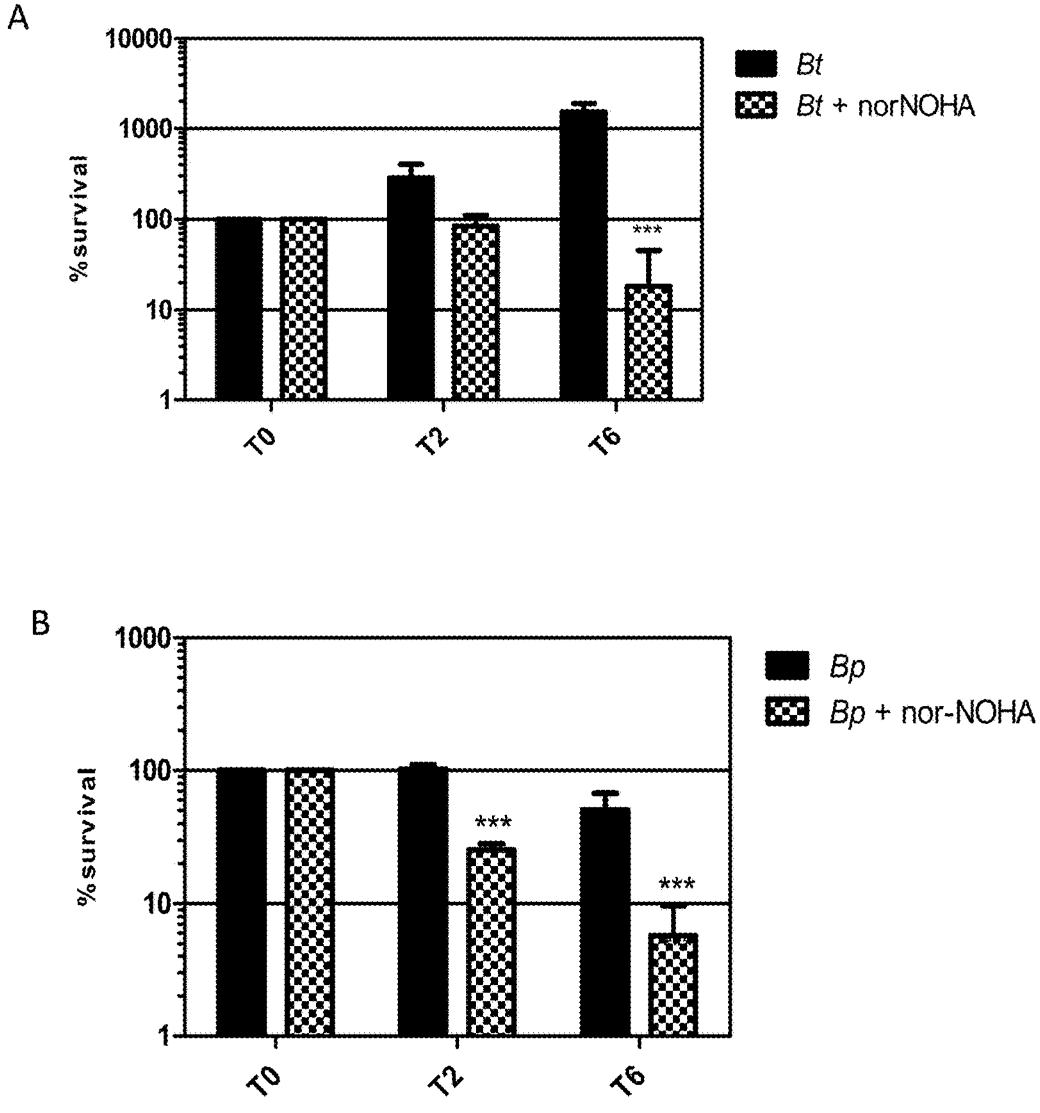
FIG. 5** shows NO levels and intracellular bacterial survival after inhibition of arginase with nor-NOHA. (A), (B) Intracellular survival in nor-NOHA treated cells two and six hours post-infection with Bt and Bp respectively. (C), (D)
Figure 5:
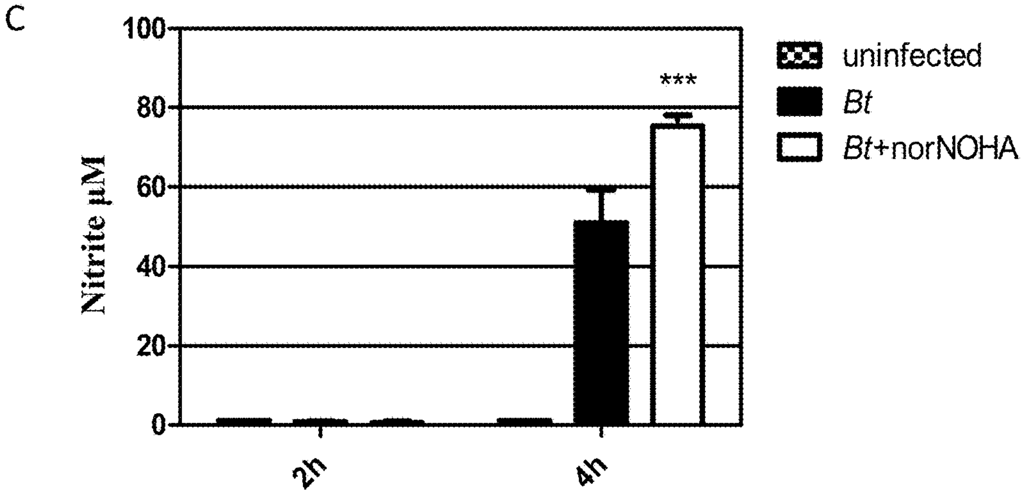
Figure 5:
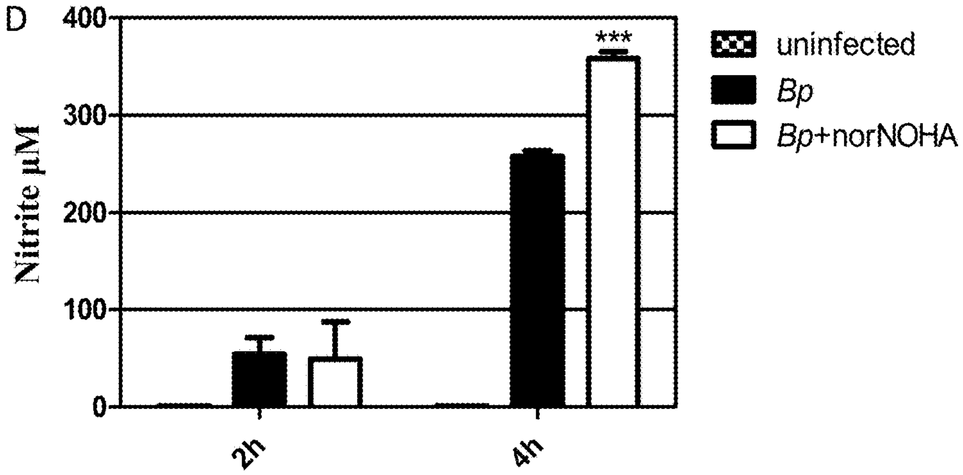

Many intracellular pathogens induce arginase expression as a mechanism for suppressing intracellular killing by macrophages. To determine whether Arg2 directly interferes with NO production and enhances *Burkholderia's* intracellular survival, the NO levels (determined using the Griess assay) and intracellular bacterial survival were examined after inhibition of arginase with nor-NOHA. A decrease in both Bt and Bps intracellular survival was observed six hours post-infection in nor-NOHA treated cells, as shown in FIGS. 5A and 5B. Furthermore, nor-NOHA treatment led to a increase in NO levels four hours post-infection, as shown in FIGS. 5C and 5D. This indicates that arginase is promoting bacterial survival, which might be partly attributed to its impact on NO production.

Example A5—PGE-2 is Produced in the Lung During *Burkholderia* Infection

Figure 6:
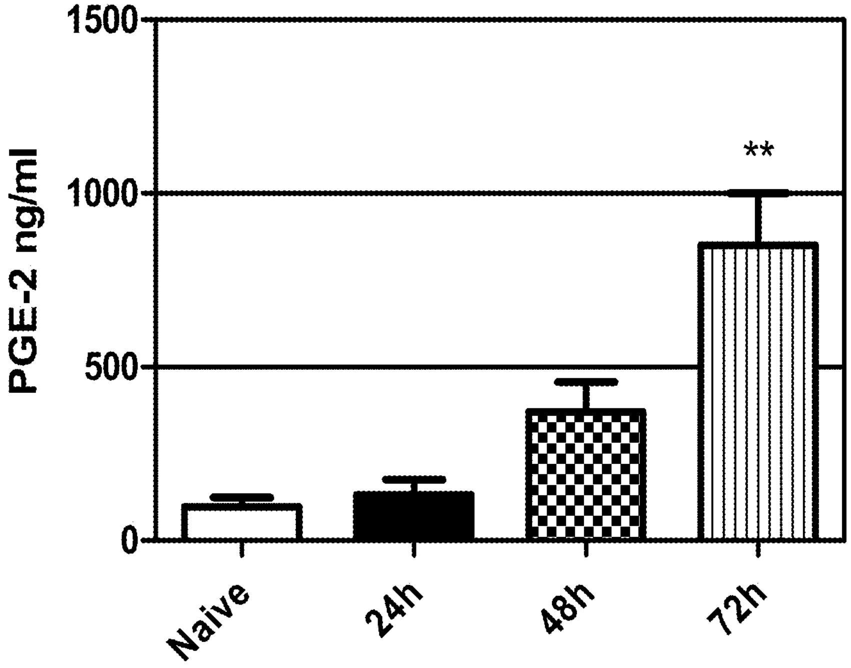
FIG. 6 shows PGE-2 levels in lung homogenates of BALB/c mice obtained at 24, 48, and 72 hours post-infection with a lethal dose of Bt ($10^6$ cfu). $p<0.01$
Figure 7:
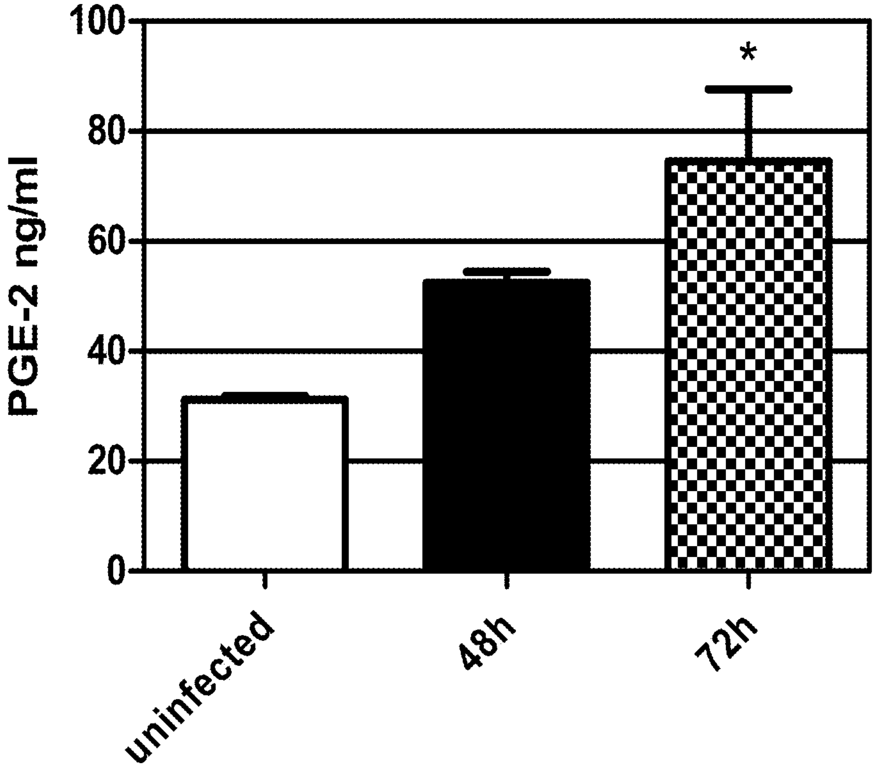
FIG. 7 shows PGE-2 levels in lung homogenates of BALB/c mice obtained at 24, 48, and 72 hours post-infection with a lethal dose of Bps ($3\times10^3$ cfu). *$p<0.05$

Pneumonia is a frequent clinical presentation of melioidosis and is involved in at least half of all melioidosis cases. Patients presenting with pneumonia are more prone to septic shock compared with other clinical primary presentations. To study the role of PGE-2 in pulmonary melioidosis, BALB/c mice (Bps susceptible strain) were challenged by the intranasal route with a lethal dose of Bt ($10^6$ cfu) or Bps ($3\times10^3$ cfu). PGE-2 levels were measured in lung homogenates obtained at 24, 48, and 72 hours post-infection. An increase in PGE-2 was observed after 72 hours of infection, as shown in FIGS. 6 and 7.

Figure 8:
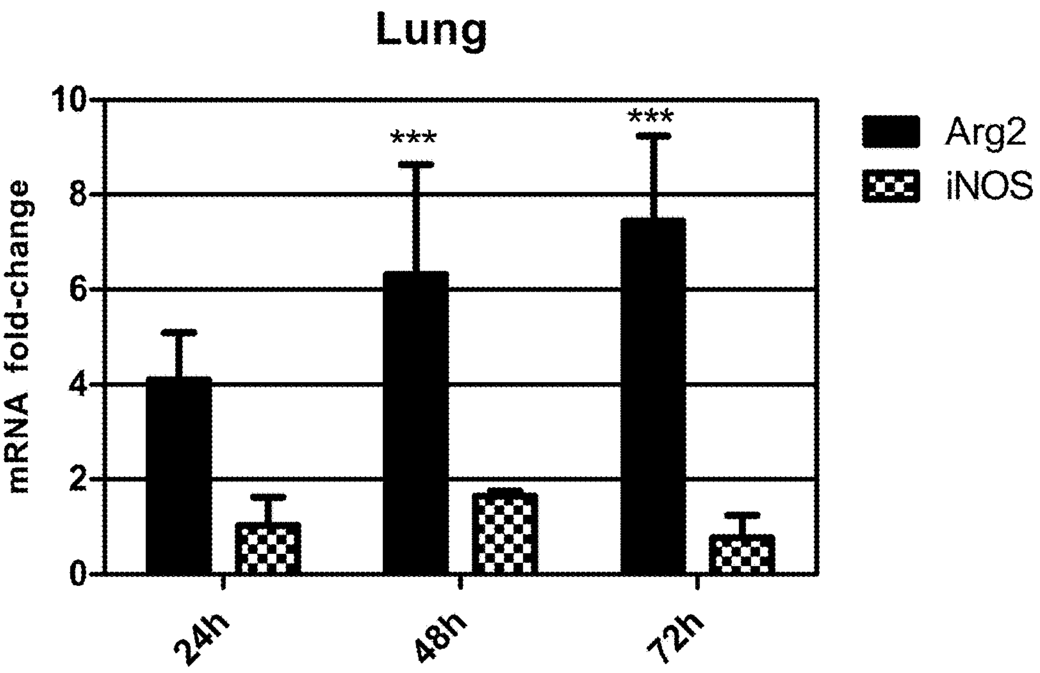
FIG. 8 shows Arg2 and iNOS expression 48 and 72 hours post-infection in the lungs of Bt-infected mice. *$p<0.001$
Figure 9:
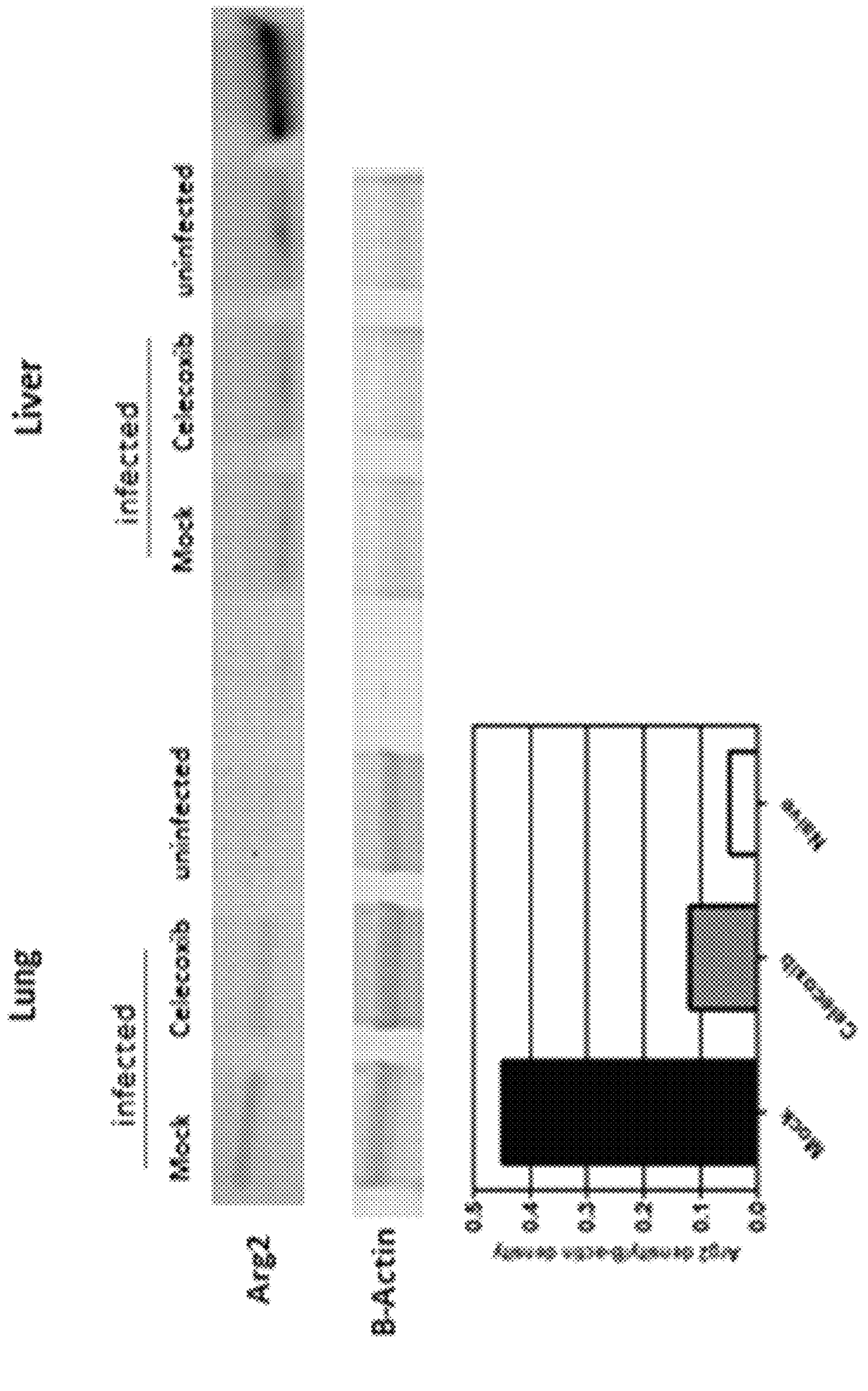
FIG. 9** shows a Western blot analysis of lung and liver tissue for Arg2 levels in mice treated with 80 mg/kg Celecoxib compared to mock-treated mice 48 hours after pulmonary Bt infection.
Figure 10:
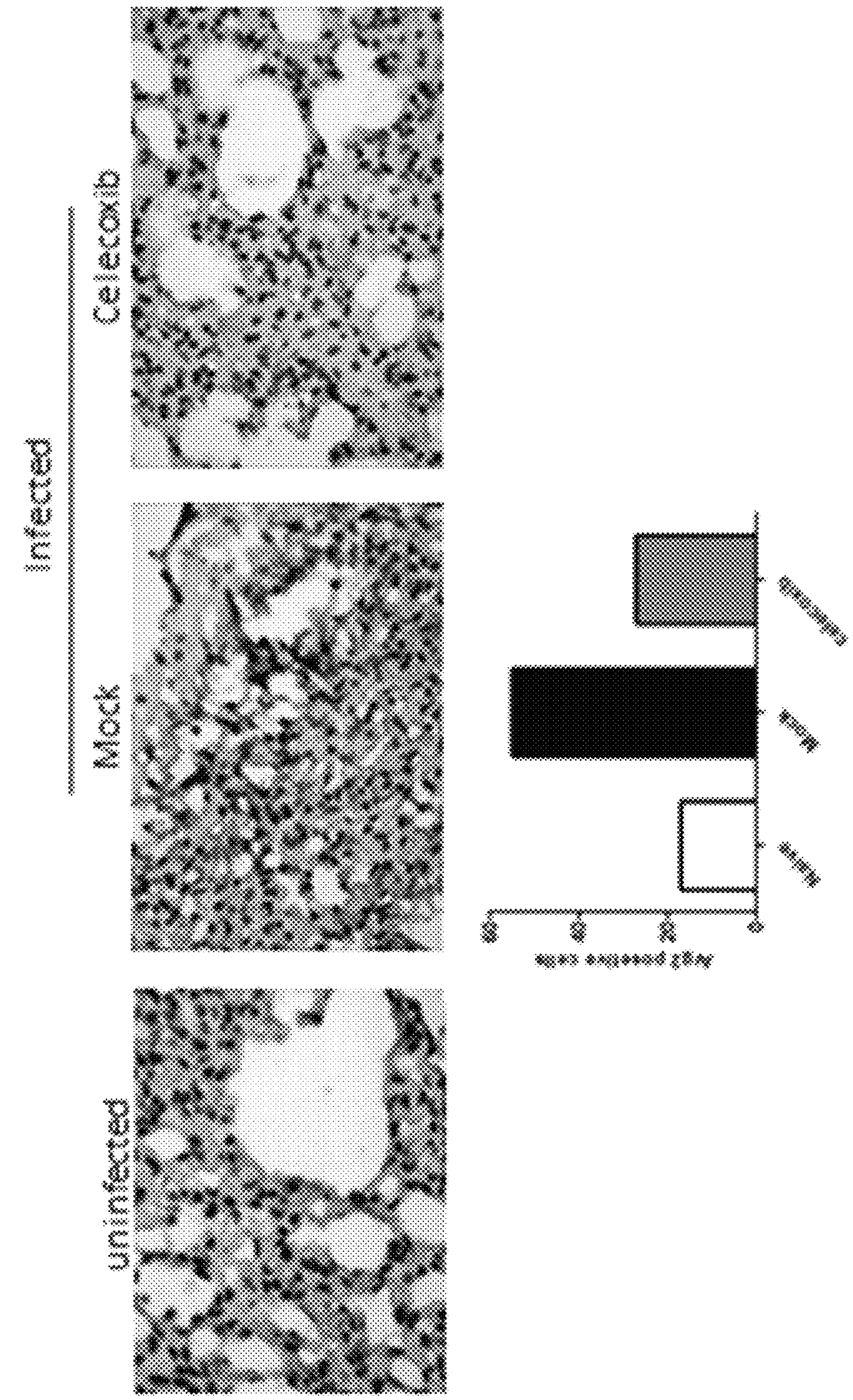
FIG. 10 shows immunohistochemical staining analyses of Arg2 in the lungs of mice treated with 80 mg/kg Celecoxib and mock-treated infected mice and untreated uninfected mice.

Example A6—Arg2 Expression Increases in Bt Challenged Mice and Decreases after Blocking PGE-2 Production PGE-2 enhanced Arg2 expression and bacterial intracellular survival in vitro. Therefore, Arg2 expression was evaluated in the lungs of Bt-infected mice. A six to eight fold increase in Arg2 expression was observed at 48 and 72 hours post-infection, as shown in FIG. 8, while no increase in iNOS expression was observed up to 72 hours. Western blot analysis of lung and liver tissue for Arg2 demonstrated a reduction in Arg2 in the lungs, but not in the liver, of Celecoxib-treated mice compared to mock-treated mice 48 hours after pulmonary Bt infection, as shown in FIG. 9. Similarly, immunohistochemical staining analyses revealed a reduction in the number of Arg2 positively-stained cells in Celecoxib-treated mice, shown in FIG. 10. Both Western blot and IHC staining demonstrated increased Arg2 in the lungs of Bt-infected mice compared to uninfected mice.

Figure 11:
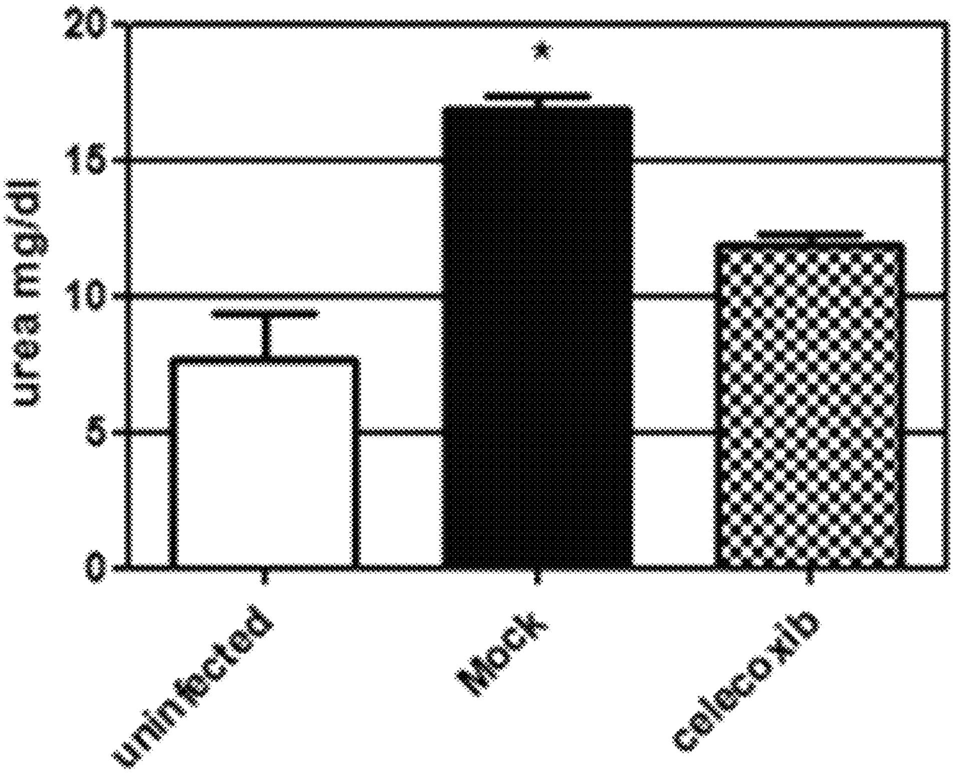
FIG. 11 shows urea levels in the lungs of uninfected mice, mock-treated infected mice and infected mice treated with 80 mg/kg Celecoxib. *$p<0.05$

To further confirm differences in Arg2 expression in the lungs of Celecoxib- and mock-treated mice, a quantitative assay for urea was employed. Urea is a byproduct of L-arginine degradation by arginase and thus provides an indirect measurement of Arg activity. Urea levels were lower in the lungs of Celecoxib-treated mice compared to mock-treated animals, as shown in FIG. 11. Taken together, these findings support that Cox-2 inhibition resulted in a reduction in Arg2 activity in the lungs of infected mice.

Figure 12:
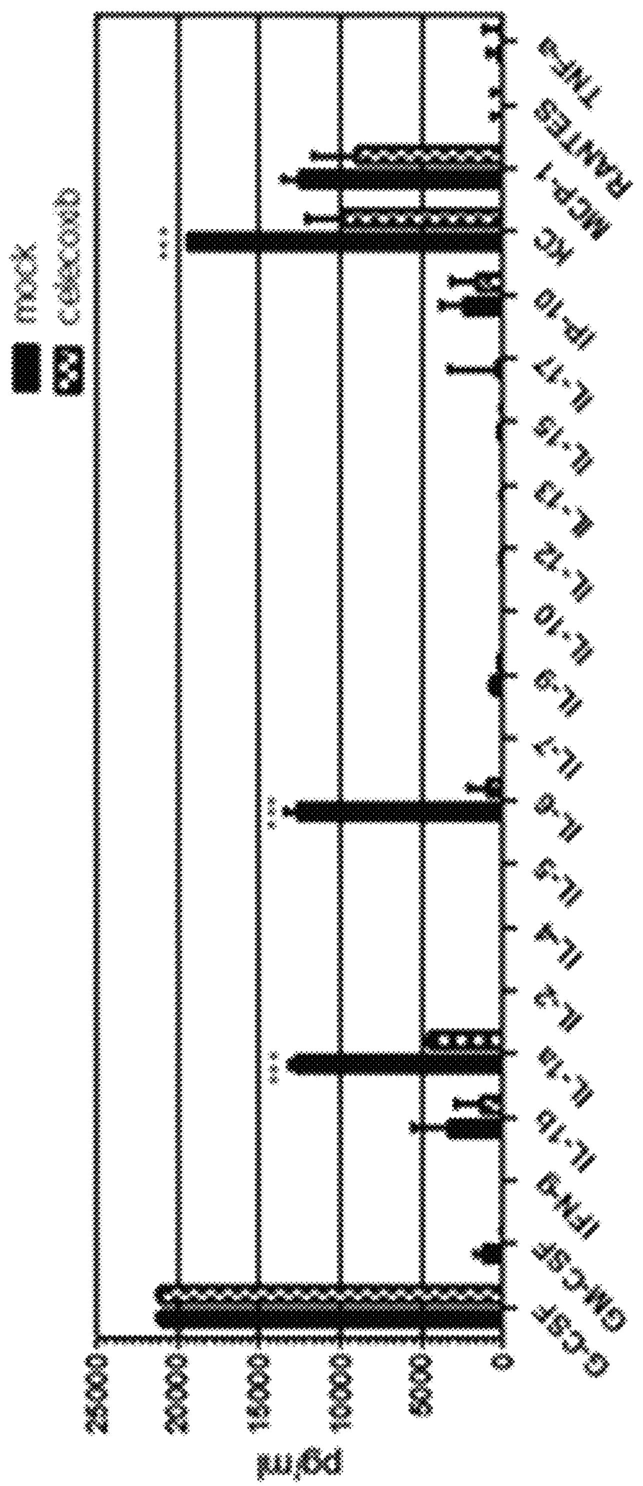
FIG. 12 shows differences in IL-1α, IL-6 and KC in the lungs of mock-treated mice and mice treated with 80 mg/kg Celecoxib 48 hours post-infection with Bt. *$p<0.001$ FIG. 13**. *B. pseudomallei* rapidly induces COX-2 and PGE-2 production by macrophages.

Example A7—Celecoxib Treatment Reduces Lung Inflammation During *Burkholderia* Infection Similar to the histological findings, high concentrations of IL-1α and IL-6 (pro-inflammatory cytokines) and KC (neutrophil chemokine) were measured in the lungs of mock-treated mice 48 hours post-infection with Bt. Conversely, IL-1α, IL-6 and KC were reduced in the lungs of Celecoxib-treated mice, as shown in FIG. 12. Overall, these data suggest that Celecoxib-treated mice have a reduction in lung inflammation during the early course of Bt infection.

EXAMPLE SET B

Method—Mice and Bacterial Challenges

Animal experiments were performed in strict accordance with the recommendations in the Guide for the Care and Use of Laboratory Animals of the National Institutes of Health. The protocol was approved by the Tulane University Institutional Animal Care and Use Committee. Six to eight week old, female BALB/c mice (Charles River) were maintained under pathogen-free conditions and fed sterile food and water ad libitum. Infections utilizing Bps were performed under Animal Biosafety Level 3 containment.

*Burkholderia pseudomallei* strain 1026b (BEI Resources) was used in this study. For infectious challenge, mice were anesthetized with Ketamine/xylazine (88 mg/kg) (Fort Dodge Animal Health). The bacterial inoculum contained $3\times10^3$ cfu (~4 $LD_{50}$) suspended in 40 μl sterile saline and 20 μL was delivered to each nostril via pipet. Bacterial cfu were confirmed by plating the inoculum on LB agar. Euthanasia endpoints used in this study included loss of >20% body weight, hunched posture and decreased movement or response to stimuli, or paralysis. In a subset of experiments, mice were treated with the selective COX-2 inhibitor, (N-[2-(cyclohexyloxy)-4-nitrophenyl]-methanesulfonamide) (NS398) (Cayman Chemicals), 3 hours post-exposure. Mice received 50 μl of NS398 (15 mg/kg) dissolved in DMSO or vehicle control (DMSO) by intraperitoneal injection. Treatments were repeated for two consecutive days. After euthanasia, tissues were removed, weighed and homogenized in 1 ml 0.9% sterile saline. Serial dilutions of tissue homogenates were plated on LB agar and bacterial cfu were counted after 2-4 days of incubation at 37° C.

Method—Cell Culture and In Vitro Experiments

J774A.1 murine macrophage-like cells were obtained from ATCC. Cells were propagated in media containing DMEM (Invitrogen) with 10% FBS (Atlanta Biologicals), 1% Pen/Strep (Invitrogen) and 1% sodium bicarbonate (Invitrogen). Bone marrow-derived macrophages (BMDM) were extracted from 8-10 week old BALB/c mice as previously described (WEISCHENFELDT et al., "Bone Marrow-Derived Macrophages: Isolation and Applications" (2008) Cold Spring Harb. Protoc., Vol. 3, Issue 12, doi:10.1101/pdb.prot5080). BMDM were propagated in RPMI (ATCC), containing 15% L929 fibroblast-conditioned media, 2 g/L D-glucose (Invitrogen), 10% FBS, 5% horse serum (Invitrogen), 1% Pen/Strep and 2 mM L-glutamine (Invitrogen). Prior to each experiment, the cytotoxic dose of bacteria and chemical treatments were pre-determined using a colorimetric assay for LDH release (Clontech). Intracellular survival assays were performed as previously described in Burtnick et al. 2008 (BURTNICK et al., "*Burkholderia pseudomallei* type III secretion system mutants exhibit delayed vacuolar escape phenotypes in RAW 264.7 murine macrophages" Infect Immun (2008) Vol. 76, pp. 2991-3000). In some experiments, cells were treated with 100 μM of NS398, 100 μM nor-$N^{\omega}$-hydroxy-L-arginine (nor-NOHA; Cayman Chemical), or 1 μM PGE-2 (Sigma). PGE-2 was measured in cell culture supernatants and lung homogenates by competitive ELISA (Pierce). Nitric oxide was measured as its stable end product nitrite by Griess assay (Invitrogen).

Method—TLR Pathway PCR Array

Fold-change in mRNA expression of 84 genes central to TLR-mediated signal transduction and innate immunity were measured by PCR array following the manufacturer's protocol and data analysis software (SABiosciences).

Method—Real Time-PCR

RT-PCR was conducted using an iCycler (BioRad) with iScript cDNA Synthesis Kit (BioRad). 1 μg of RNA was converted to cDNA following the manufacturer's protocol. 1 μl of cDNA was added to 12.5 μL of iQ SYBR Green Super Mix containing 350 nM of each forward and reverse primer. Primer sequences were as follows:

```
GAPDH:
forward,
                                  (SEQ ID NO: 1)
5'-ACAGCCGCATCTTCTTGTGCAGTG-3';

reverse,
                                  (SEQ ID NO: 2)
5'-GGCCTTGACTGTGCCGTTGAATTT-3';

Arg1:
forward,
                                  (SEQ ID NO: 3)
5'-GGGCTGGACCCAGCATTCACCCCG-3';

reverse,
                                  (SEQ ID NO: 4)
5'TCACTTAGGTGGTTTAAGGTAGTC-3';

Arg2:
forward,
                                  (SEQ ID NO: 5)
5'-GACCCTAAACTGGCTCCAGCCACA-3';

reverse,
                                  (SEQ ID NO: 6)
5'-CTAAATTCTCACACATTCTTCATT-3';

iNOS:
forward,
                                  (SEQ ID NO: 7)
5'-ATGACCAGTATAAGGCAAGC-3';

reverse,
                                  (SEQ ID NO: 8)
5'-GCTCTGGATGAGCCTATATTG-3';

COX-2:
forward,
                                  (SEQ ID NO: 9)
5'-GGAGAGAAGGAAATGGCTGCA-3';

reverse,
                                  (SEQ ID NO: 10)
5'-ATCTAGTCTGGAGTGGGAGG-3'.
```

Nuclease-free water was added to bring the total reaction volume to 25 μL. PCR was performed using the following conditions: reverse transcriptase inactivation (95° C., 3 min) followed by 40 PCR cycles (95° C., 15 seconds and 60° C., 30 seconds) followed by melt curve analysis. Fold change (up- or down-regulation) relative to base line expression in uninfected cells was calculated using the ΔΔCt method using Ct values for arginase 1, arginase 2, iNOS, COX-2, and GAPDH.

Method—Detection of COX-2 and Arginase

For Western blot, equal amounts of protein (50 μg) from cell lysates or lung homogenates were resolved by SDS-PAGE and transferred to nitrocellulose using an iBLOT (Invitrogen). Detection of COX-2 enzyme was performed using a 1:1000 dilution of rabbit polyclonal anti-COX-2 (Cell Signaling Technology), followed by peroxidase-conjugated, donkey anti-rabbit IgG (1:5000). Arg2 was detected using a 1:200 dilution of rabbit polyclonal anti-mouse Arg2 (sc-20151, Santa Cruz) and Arg1 was detected using a 1:500 dilution of Arg1 antibody 18351 (Santa Cruz). Mouse Arg2- transfected 293T cell lysate (Santa Cruz) was used a positive control for Arg2 and 5 μg of mouse liver extract was used a positive control for Arg1. β-actin, a protein loading control, was detected using 1:1000 dilution of polyclonal rabbit anti-mouse β-actin (Cell Signaling). Detection of bound antibodies was visualized by a chromogenic reaction using Opti-4CN Substrate (BioRad).

Method—Statistical Analysis

Statistical analyses were performed using Prism 5.0 software (Graph Pad). Kaplan-Meier survival curves were compared by log-rank analysis. All other data were analyzed using a one-way or two-way ANOVA followed by the Bonferroni post-test to determine statistical differences between groups. $p<0.05$ was considered statistically significant. All data are representative of at least two independent experiments.

Example B1—*B. pseudomallei* Rapidly Induces PGE-2 Production by Macrophages In order to identify host cell signaling pathways that might contribute to *B. pseudomallei* intracellular persistence, we performed a Toll-like receptor (TLR or Tlr) PCR array on J744A.1 macrophages infected with *B. thailandensis*. *B. thailandensis* is a commonly used biosafety level 2 surrogate organism for the study of *B. pseudomallei* and, with the exception of capsular polysaccharide, possesses all of the known *B. pseudomallei* virulence determinants such as Type 3 and Type 6 secretion systemS. Although *B. thailandensis* is 1,000- to 100,000-fold less virulent than *B. pseudomallei* in animal models, the organisms behave very similarly in vitro. *B. thailandensis* and *B. pseudomallei* induce pyroptosis in macrophages as early as 8 hours post infection at a multiplicity of infection (MOI) 10 or greater. In pilot experiments, we determined that J774A.1 macrophages infected with *B. thailandensis* at MOI 10 or 1 displayed 80% and 28% cytotoxicity, respectively at 8 hours post-infection (data not shown). Therefore, experiments utilizing J774A.1 macrophages or primary bone marrow-derived macrophages (BMDM) were limited to an eight hour experimental time course using *B. thailandensis* or *B. pseudomallei* at MOI 1 or lower (0.1).

Table 2 shows the fold-change in mRNA expression of 84 different genes from the Toll-like receptor pathway. J774A.1 macrophages were infected with *B. thailandensis* E264 (MOI 1) and gene expression was analyzed at 2 and 8 hours post-infection. Change in mRNA expression is represented as fold change over uninfected controls. The abbreviation n.c. indicates no change in expression.

TABLE 2

| Symbol | Description | Fold-Difference 2 h | Fold-Difference 8 h |
|---|---|---|---|
| Agfg1 | ArfGAP with FG repeats 1 | n.c. | 128.0 |
| Btk | Bruton agammaglobulinemia tyrosine kinase | n.c. | n.c. |
| Casp8 | Caspase 8 | n.c. | n.c. |
| Ccl2 | Chemokine (C-C motif) ligand 2 | 5.0 | 13.9 |
| Cd14 | CD14 antigen | n.c. | 4.5 |
| Cd80 | CD80 antigen | n.c. | 17.1 |
| Cd86 | CD86 antigen | n.c. | 3821.7 |
| Cebpb | CCAAT/enhancer binding protein (C/EBP), beta | n.c. | 24.2 |
| Chuk | Conserved helix-loop-helix ubiquitous kinase | −5.4 | 1448.1 |
| Clec4e | C-type lectin domain family 4, member e | n.c. | 274.3 |
| Csf2 | Colony stimulating factor 2 (granulocyte-macrophage) | 4.4 | 24.2 |
| Csf3 | Colony stimulating factor 3 (granulocyte) | 66.2 | 5042.7 |
| Cxcl10 | Chemokine (C-X-C motif) ligand 10 | 30.9 | 8.0 |
| Eif2ak2 | Eukaryotic translation initiation factor 2-alpha kinase 2 | 7.2 | 445.7 |
| Elk1 | ELK1, member of ETS oncogene family | n.c. | 5.2 |
| Fadd | Fas (TNFRSF6)-associated via death domain | n.c. | n.c. |
| Fos | FBJ osteosarcoma oncogene | n.c. | 34.2 |
| Hmgb1 | High mobility group box 1 | −5.8 | n.c. |
| Hras1 | Harvey rat sarcoma virus oncogene 1 | n.c. | n.c. |
| Hspa1a | Heat shock protein 1A | n.c. | n.c. |
| Hspd1 | Heat shock protein 1 (chaperonin) | n.c. | 7643.4 |
| Ifnb1 | Interferon beta 1, fibroblast | 5.8 | 8.0 |
| Ifng | Interferon gamma | n.c. | 8.0 |
| Ikbkb | Inhibitor of kappaB kinase beta | n.c. | 55.7 |
| Il10 | Interleukin 10 | 10.1 | 97.0 |
| Il12a | Interleukin 12A | n.c. | 8.0 |
| Il1a | Interleukin 1 alpha | 21.8 | 103.9 |
| Il1b | Interleukin 1 beta | 26.9 | 194.0 |
| Il1r1 | Interleukin 1 receptor, type I | n.c. | n.c. |
| Il2 | Interleukin 2 | n.c. | n.c. |
| Il6 | Interleukin 6 | 76.1 | 891.4 |
| Il6ra | Interleukin 6 receptor, alpha | n.c. | n.c. |
| Irak1 | Interleukin-1 receptor-associated kinase 1 | −5.0 | 73.5 |
| Irak2 | Interleukin-1 receptor-associated kinase 2 | n.c. | 2702.3 |
| Irf1 | Interferon regulatory factor 1 | n.c. | 207.9 |
| Irf3 | Interferon regulatory factor 3 | n.c. | 25.9 |
| Jun | Jun oncogene | n.c. | 1552.0 |
| Lta | Lymphotoxin A | n.c. | n.c. |
| Ly86 | Lymphocyte antigen 86 | −13.4 | n.c. |
| Ly96 | Lymphocyte antigen 96 | n.c. | n.c. |
| Map2k3 | Mitogen-activated protein kinase kinase 3 | n.c. | n.c. |
| Map2k4 | Mitogen-activated protein kinase kinase 4 | n.c. | 36.7 |
| Map3k1 | Mitogen-activated protein kinase kinase kinase 1 | n.c. | 8.0 |
| Map3k7 | Mitogen-activated protein kinase kinase kinase 7 | n.c. | 831.7 |

TABLE 2-continued

| Symbol | Description | Fold-Difference 2 h | Fold-Difference 8 h |
|---|---|---|---|
| Mapk8 | Mitogen-activated protein kinase 8 | n.c. | 128 |
| Mapk8ip3 | Mitogen-activated protein kinase 8 interacting protein 3 | n.c. | 1024 |
| Mapk9 | Mitogen-activated protein kinase 9 | n.c. | 55.7 |
| Muc13 | Mucin 13, epithelial transmembrane | −8.2 | 8 |
| Myd88 | Myeloid differentiation primary response gene 88 | n.c. | 18.3 |
| Nfkb1 | Nuclear factor of kappa light polypeptide gene enhancer in B-cells 1, p105 | 8.8 | n.c. |
| Nfkb2 | Nuclear factor of kappa light polypeptide gene enhancer in B-cells 2, p49/p100 | n.c. | 8 |
| Nfkbia | Nuclear factor of kappa light polypeptide gene enhancer in B-cells inhibitor, alpha | 6.2 | 19.6 |
| Nfkbib | Nuclear factor of kappa light polypeptide gene enhancer in B-cells inhibitor, beta | n.c. | 8 |
| Nfkbil1 | Nuclear factor of kappa light polypeptide gene enhancer in B-cells inhibitor-like 1 | n.c. | n.c. |
| Nfrkb | Nuclear factor related to kappa B binding protein | n.c. | 18.3 |
| Nr2c2 | Nuclear receptor subfamily 2, group C, member 2 | n.c. | 5.6 |
| Peli1 | Pellino 1 | n.c. | 3326.9 |
| Pglyrp1 | Peptidoglycan recognition protein 1 | n.c. | 8 |
| Ppara | Peroxisome proliferator activated receptor alpha | n.c. | 22.6 |
| Ptgs2 (COX-2) | Prostaglandin-endoperoxide synthase 2 | 430.5 | 16384 |
| Rel | Reticuloendotheliosis oncogene | 8.2 | n.c. |
| Rela | V-rel reticuloendotheliosis viral oncogene homolog A (avian) | n.c. | n.c. |
| Ripk2 | Receptor (TNFRSF)-interacting serine-threonine kinase 2 | n.c. | 6.4 |
| Tbk1 | TANK-binding kinase 1 | n.c. | n.c. |
| Ticam1 | Toll-like receptor adaptor molecule 1 | n.c. | n.c. |
| Ticam2 | Toll-like receptor adaptor molecule 2 | n.c. | 16 |
| Tirap | Toll-interleukin 1 receptor (TIR) domain-containing adaptor protein | 6.7 | 5.6 |
| Tlr1 | Toll-like receptor 1 | n.c. | 84.4 |
| Tlr2 | Toll-like receptor 2 | n.c. | 2194.9 |
| Tlr3 | Toll-like receptor 3 | n.c. | 42.2 |
| Tlr4 | Toll-like receptor 4 | 5.8 | 207.9 |
| Tlr5 | Toll-like receptor 5 | n.c. | 7.4 |
| Tlr6 | Toll-like receptor 6 | n.c. | n.c. |
| Tlr7 | Toll-like receptor 7 | n.c. | −4.5 |
| Tlr8 | Toll-like receptor 8 | n.c. | −8 |
| Tlr9 | Toll-like receptor 9 | n.c. | −6.4 |
| Tnf | Tumor necrosis factor | 7.2 | 7.4 |
| Tnfaip3 | Tumor necrosis factor, alpha-induced protein 3 | 5.8 | 42.2 |
| Tnfrsf1a | Tumor necrosis factor receptor superfamily, member 1a | 76.1 | n.c. |
| Tollip | Toll interacting protein | n.c. | 9.1 |
| Tradd | TNFRSF1A-associated via death domain | n.c. | 181.0 |
| Traf6 | Tnf receptor-associated factor 6 | 28.8 | 588.1 |
| Ube2n | Ubiquitin-conjugating enzyme E2N | 10.9 | 32 |
| Ube2v1 | Ubiquitin-conjugating enzyme E2 variant 1 | n.c. | 256 |

*B. thailandensis* upregulated expression of TLR1 and TLR2 by two hours post-infection, and increases in TLR1, TLR2, TLR3, TLR4, and TLR5 mRNA expression were observed by eight hours post-infection (Table 2). No change in mRNA expression was observed for TLR6, TLR7, TLR8, or TLR9. An increase (430-fold) in COX-2 mRNA expression occurred by two hours post-infection and further increased by >16,000-fold at eight hours (Table 2). COX-2 is an enzyme involved in the production of PGE-2.

Figure 13:
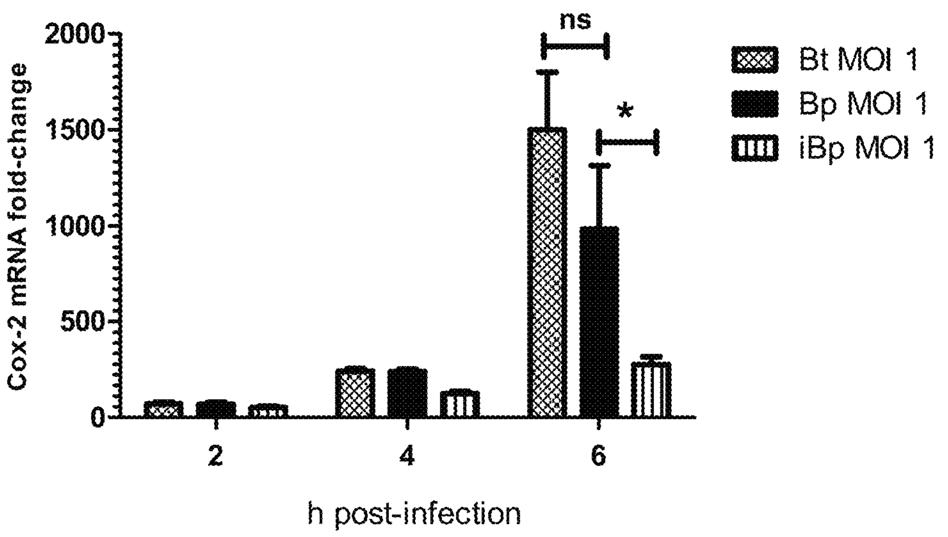
FIG. 13A. Bone-marrow derived macrophages (BMDM) were treated with viable *B. thailandensis* (Bt), *B. pseudomallei* (Bp) or heat-inactivated Bp (iBp) at MOI 1 and COX-2 mRNA expression was measured by RT-PCR.
FIG. 13B. COX-2 enzyme was detected by Western blot in BMDM infected with Bp at MOI 1.
FIG. 13C. BMDM were treated with Bp at MOI 0.1 or 1 and iBp at MOI 1 and PGE-2 was measured in culture supernatants by ELISA. The data represent biological triplicates per time point. Error bars represent the standard deviation (SD). Statistical significance was determined using a two way ANOVA with Bonferroni post-test. *$p<0.05$, ***$p<0.001$. Data is representative of two independent experiments.
Figure 13:
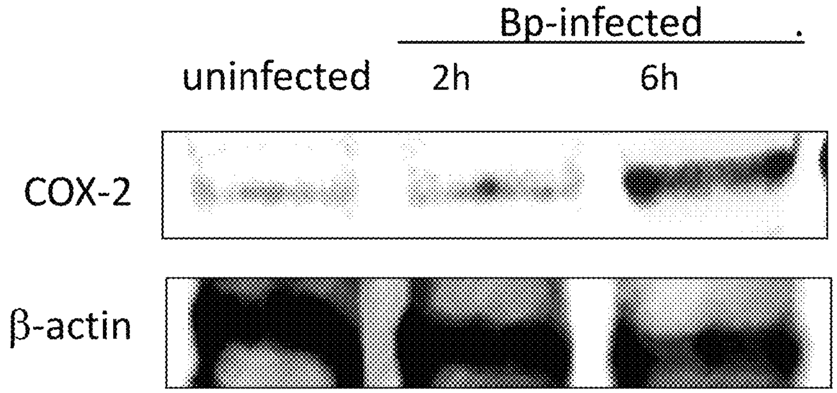
Figure 13:
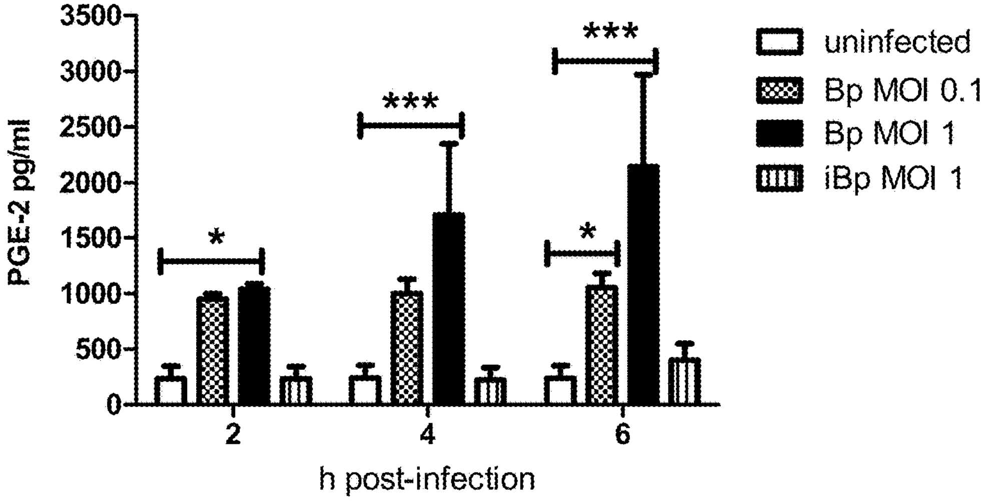

To confirm the TLR array results obtained for *B. thailandensis*-infected J774A.1 macrophages, BMDM were infected with *B. thailandensis and B. pseudomallei* (MOI 1) and COX-2 mRNA expression was measured by RT-PCR. *B. thailandensis* and *B. pseudomallei* both up-regulated COX-2 mRNA expression in BMDM to a similar extent (FIG. 13A), although the levels of mRNA expression were lower than that observed for *B. thailandensis*-infected J774A.1 cells and may reflect differences between immortalized and primary cell lines (FIG. 13A, Table 2). COX-2 enzyme and its end product, PGE-2, were also produced by macrophages in response to *B. pseudomallei* in a time- and dose-dependent manner (FIG. 13B-C). Since lipopolysaccharide (LPS) of Gram-negative bacteria is known to induce COX-2 and PGE-2 production, we evaluated whether the PGE-2 response of infected macrophages was simply a passive signaling event mediated by TLR4 recognition of LPS. Notably, heat inactivation of *B. pseudomallei* appeared to abolished COX-2 and PGE-2 expression (FIG. 13A-C) indicating that viable bacteria and/or bacterial proteins are required for early PGE-2 production by macrophages.

Example B2—PGE-2 Enhances *B. pseudomallei* Intracellular Survival

Figure 14:
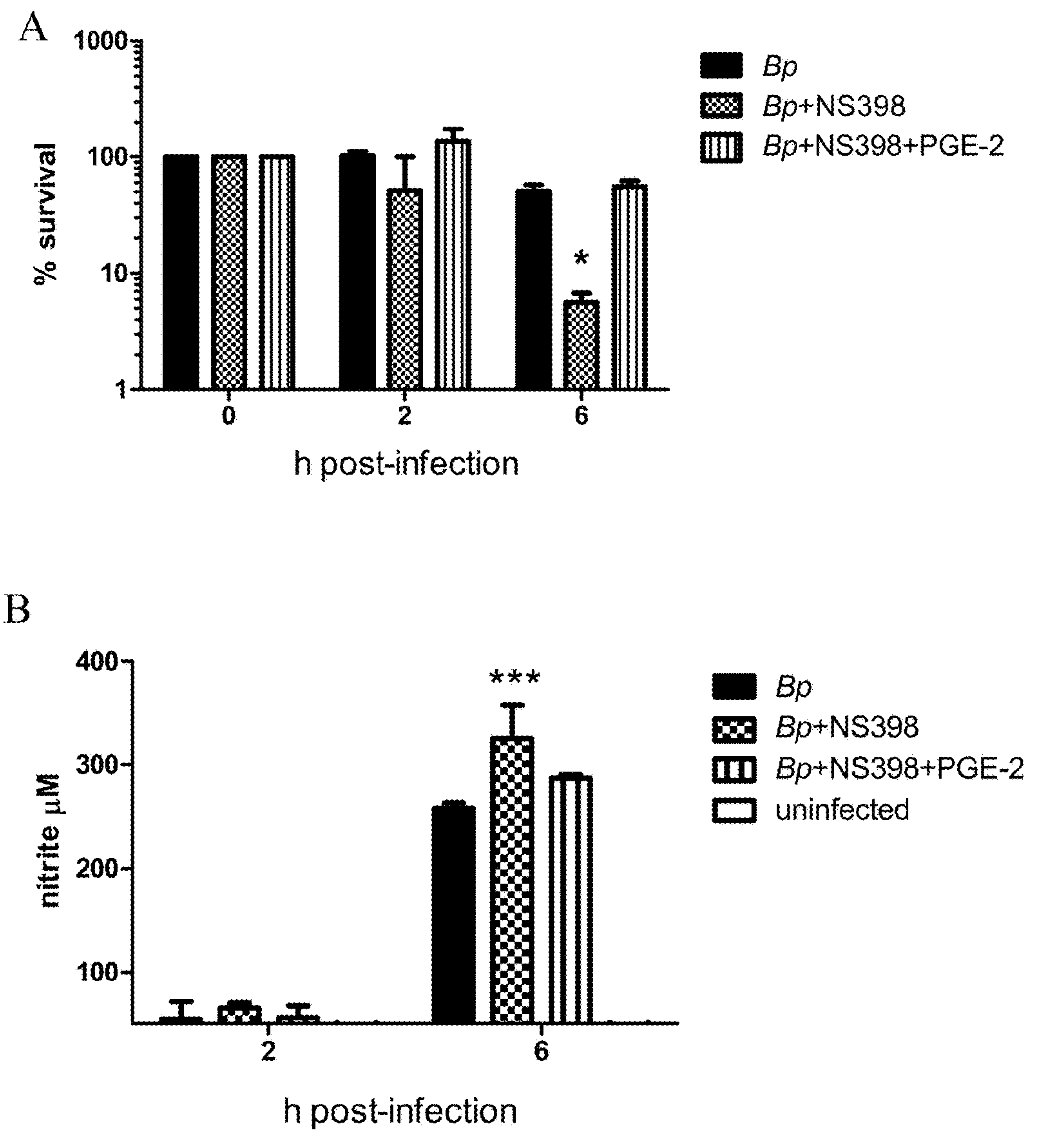
FIG. 14. PGE-2 promotes *B. pseudomallei* intracellular survival. BMDM were incubated in the presence or absence of NS398 (100 μM)+/−PGE-2 (1 μM) for 30 minutes then infected with Bps at MOI 1.

Because PGE-2 has been shown to suppress macrophage bactericidal mechanisms, we assessed the impact of COX-2 activation and PGE-2 production on *B. pseudomallei* intracellular survival using the selective COX-2 inhibitor, NS398. Preliminary dose-response experiments were conducted using 10 to 200 μM NS398 (data not shown). BMDM treated with >100 μM NS398 demonstrated enhanced intracellular killing of *B. pseudomallei* compared to non-treated cells by six hours post-infection (FIG. 14A). To verify the specificity of NS398 and that endogenous PGE-2 is responsible for the suppression of bacterial killing, exogenous PGE-2 was added to NS398-treated cells. Addition of PGE-2 to the cell cultures restored *B. pseudomallei* intracellular survival (FIG. 14A) confirming that PGE-2 promotes a favorable environment for *B. pseudomallei*.

We evaluated the downstream effect of PGE-2 on the macrophage NO response to *B. pseudomallei* infection. Treatment of BMDM with the COX-2 inhibitor NS398 led to an increase in nitrite, the stable end product of NO (FIG. 14B). This effect was not drug-specific because similar results were obtained using the COX inhibitor, indomethacin (data not shown). Conversely, the addition of exogenous PGE-2 to NS398-treated macrophages reduced nitrite levels in *B. pseudomallei*-infected cells (FIG. 14B). This suggests that PGE-2-mediated suppression of NO production may partially contribute to *B. pseudomallei* intracellular survival.

Example B3—Arginase 2 Enhances Bps Intracellular Survival

Figure 15:
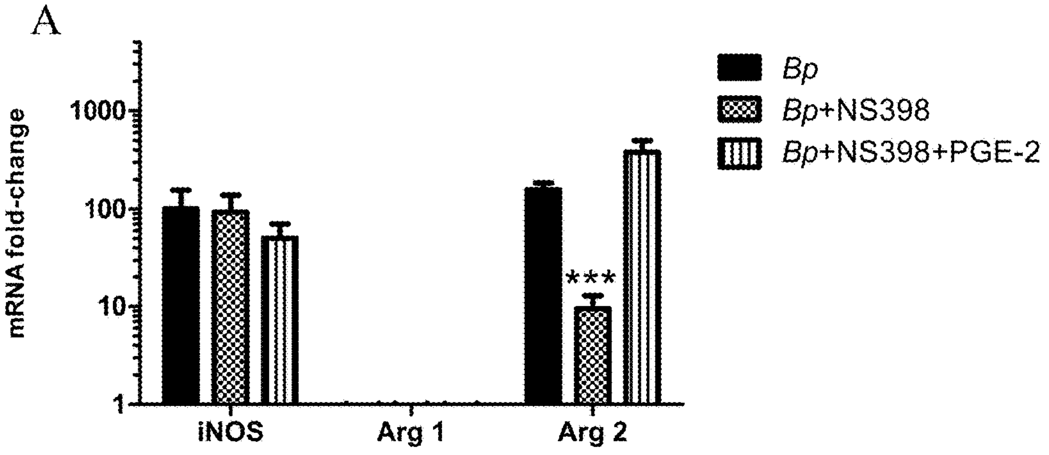
FIG. 15. Arginase 2 enhances *B. pseudomallei* survival in macrophages. BMDM were incubated in the presence or absence of NS398 (100 μM)+/−PGE-2 (1 μM) for 30 minutes, then infected with Bps at MOI 1 for 4 hours.
Figure 15:
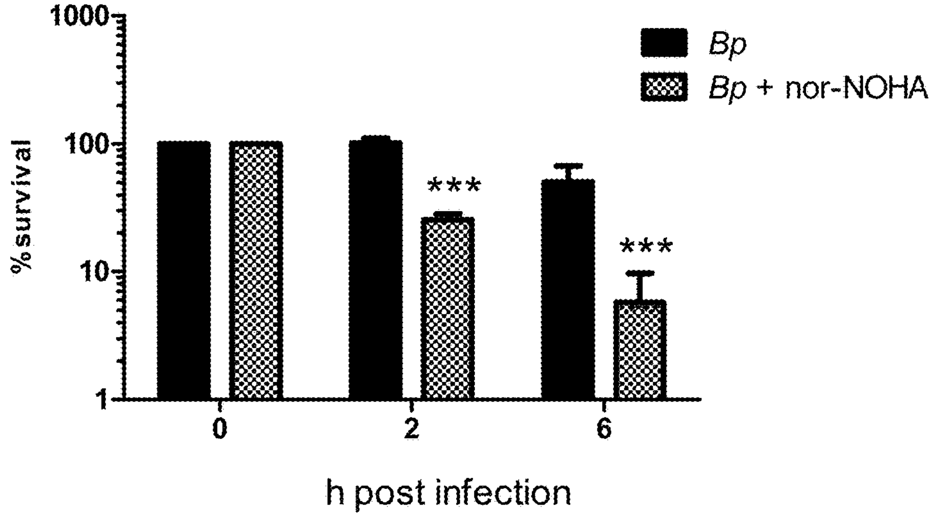
Figure 15:
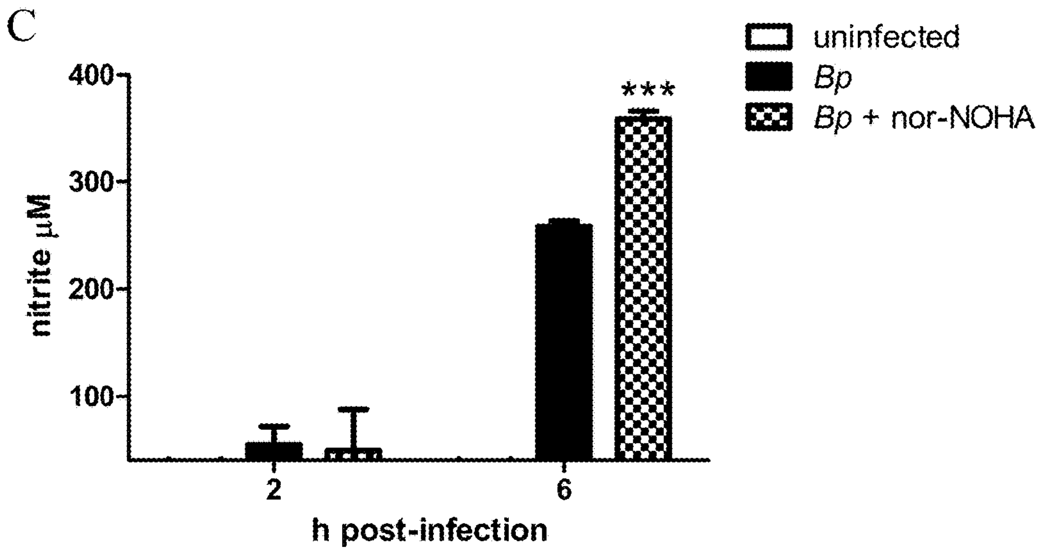

We next examined the effect of endogenous PGE-2 production on the expression of iNOS, which is required for the synthesis of NO. We did not observe any apparent change in iNOS mRNA expression in NS398- or PGE-2-treated cells compared to controls infected with *B. pseudomallei* (FIG. 15A). This suggested that PGE-2 did not directly regulate iNOS in *B. pseudomallei*-infected cells and that other mechanisms were responsible for the reduced levels of NO.

Since the enzymes arginase 1 (Arg1) and 2 (Arg2) compete with iNOS for the substrate, L-arginine, we postulated that PGE-2 induction of arginase could alter the level of NO production during *B. pseudomallei* infection. PGE-2 induction of macrophage arginase promotes tumor cell growth by suppressing NO-mediated tumor cytotoxicity. Arg1 expression was not detected after four hours of *B. pseudomallei*-infection, but the expression of Arg2 was increased (155-fold) in *B. pseudomallei*-infected BMDM (FIG. 15A). NS398-treated macrophages demonstrated a reduction in Arg2 expression while treatment with exogenous PGE-2 increased Arg2 expression by 376-fold (FIG. 15A). These data suggest that endogenous PGE-2 may interfere with NO production by enhancing Arg2 expression.

Modulation of the arginase pathway contributes to the intracellular survival of multiple pathogens, including *Salmonella* and *Mycobacterium* spp. To determine whether Arg2 directly interferes with NO production and enhances *B. pseudomallei* intracellular survival, we treated macrophages with the arginase inhibitor, nor-NOHA. A decrease in *B. pseudomallei* intracellular survival was observed in nor-NOHA-treated BMDM (FIG. 15B) and this corresponded to an increase in nitrite levels (FIG. 15C). Collectively, these results indicate that Arg2 expression promotes *B. pseudomallei* intracellular survival, in part, through suppression of macrophage NO synthesis.

Example B4—PGE-2 is Produced During Bps Pulmonary Infection

Figure 16:
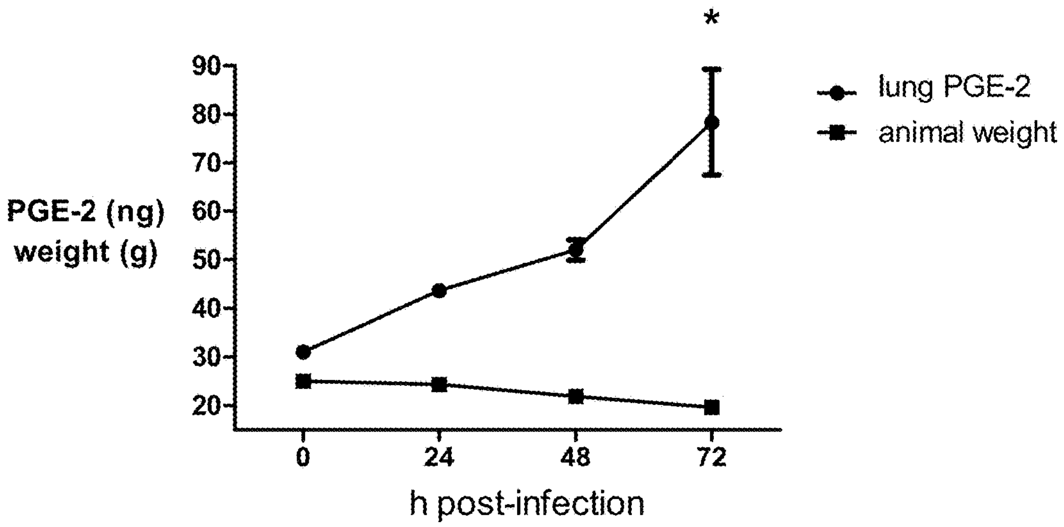
FIG. 16. Lung PGE-2 increases in a time-dependent manner after pulmonary challenge with *B. pseudomallei*. BALB/c mice were infected intranasally with $3\times10^3$ cfu of Bps and serially sacrificed between 0 (pre-challenge) and 72 hours post-infection (n=3 per timepoint). Animal weight was recorded daily and PGE-2 was measured in total lung homogenates by ELISA. Error bars represent the SEM. *$p<0.05$ compared to 0h timepoint as determined by one way ANOVA. Data is representative of two independent experiments.

Inhalational infection with *B. pseudomallei* is a natural route of exposure and represents a route of infection in a deliberate biological attack. In order to evaluate the role of PGE-2 during pneumonic melioidosis, genetically-susceptible BALB/c mice were challenged by the intranasal route with a lethal dose of *B. pseudomallei* ($3\times10^3$ cfu). Pulmonary infection with *B. pseudomallei* progressed rapidly in mice leading to greater than 20% weight loss by 72 hours post-infection (FIG. 16). An increase in lung PGE-2 was observed by 72 hours post-infection and correlated with disease progression (p=0.029 by Pearson statistical analysis) (FIG. 16). These results indicate that PGE-2 may play an important role in pneumonic melioidosis during the early stages of infection.

Figure 17:
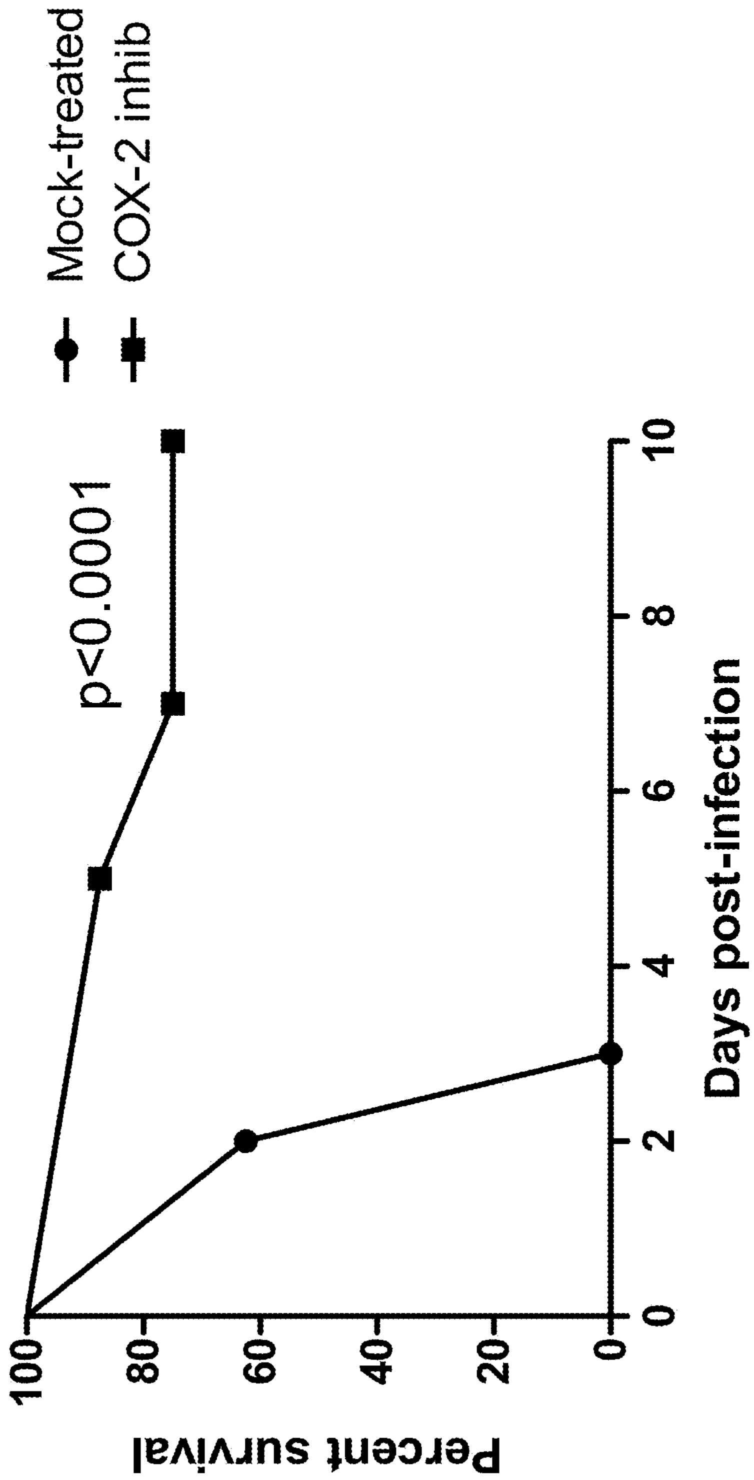
FIG. 17. COX-2 inhibition provides protection against lethal pulmonary melioidosis. BALB/c mice (n=8 per group) were infected with $3\times10^3$ cfu (4 LD50) of Bps 1026b intranasally. Three hours post-exposure, mice were administered 15 mg/kg of COX-2 inhibitor (NS398) or DMSO (Mock treatment) intraperitoneally, then again daily for two consecutive days. Survival was monitored for 10 days. Statistical significance was determined using Kaplan Meier analysis. $p<0.0001$. Data is representative of two independent bacterial challenge experiments.

Example B5—Protective Efficacy of COX-2 Inhibition Against Pneumonic Melioidosis Because PGE-2 inhibition enhanced bacterial clearance in vitro and because PGE-2 is elevated in *B. pseudomallei*-infected lungs, we evaluated the efficacy of COX-2 inhibition as a post-exposure therapeutic strategy against lethal *B. pseudomallei* pulmonary challenge. Mice were given NS398 or mock control by i.p. administration three hours after *B. pseudomallei* intranasal infection, and treatments were repeated for two consecutive days. Initiation of therapy within three hours is clinically relevant in the case of a known biological exposure to *B. pseudomallei*, such as a laboratory accident. A daily maximum dose of 15 mg/kg of NS398 was selected based upon previously documented pharmacological efficacy in mice (particularly in reducing lung PGE-2) without any associated toxicity. Mock-treated mice infected with *B. pseudomallei* rapidly displayed signs of pulmonary disease and all had to be euthanized within 72 hours (FIG. 17). Lungs of mock-treated mice all contained greater than $10^6$ cfu of *B. pseudomallei* at the time of euthanasia. In contrast, none of the NS398-treated mice showed signs of illness until day 5 post-infection. On day 5, one mouse in the NS398-treated group displayed hind leg paralysis and was humanely euthanized. This was observed again in another animal on day 7. No bacteria were recovered from the lungs of either animal. Intranasal infection of mice with *B. pseudomallei* often manifests in colonization of the brain with subsequent neurologic complication, and we believe that this, and not pulmonary disease, likely accounted for the animals' morbidity. By day 10, all of the remaining NS398-treated mice appeared to have recovered from the infection. NS398-treated mice showed no evidence of weight loss throughout the study (data not shown). No bacteria were recovered from the lungs of NS398-treated mice at the study endpoint with the exception of one animal that contained 104 cfu. All of the mice were colonized with 20-100 cfu in the spleen and liver, indicating that bacterial dissemination from the lung had occurred. These results indicate that host PGE-2 production promotes the pathogenesis of *B. pseudomallei* during pneumonic melioidosis and that inhibition of COX-2 enhances bacterial clearance from the lung and improves host survival.

Figure 18:
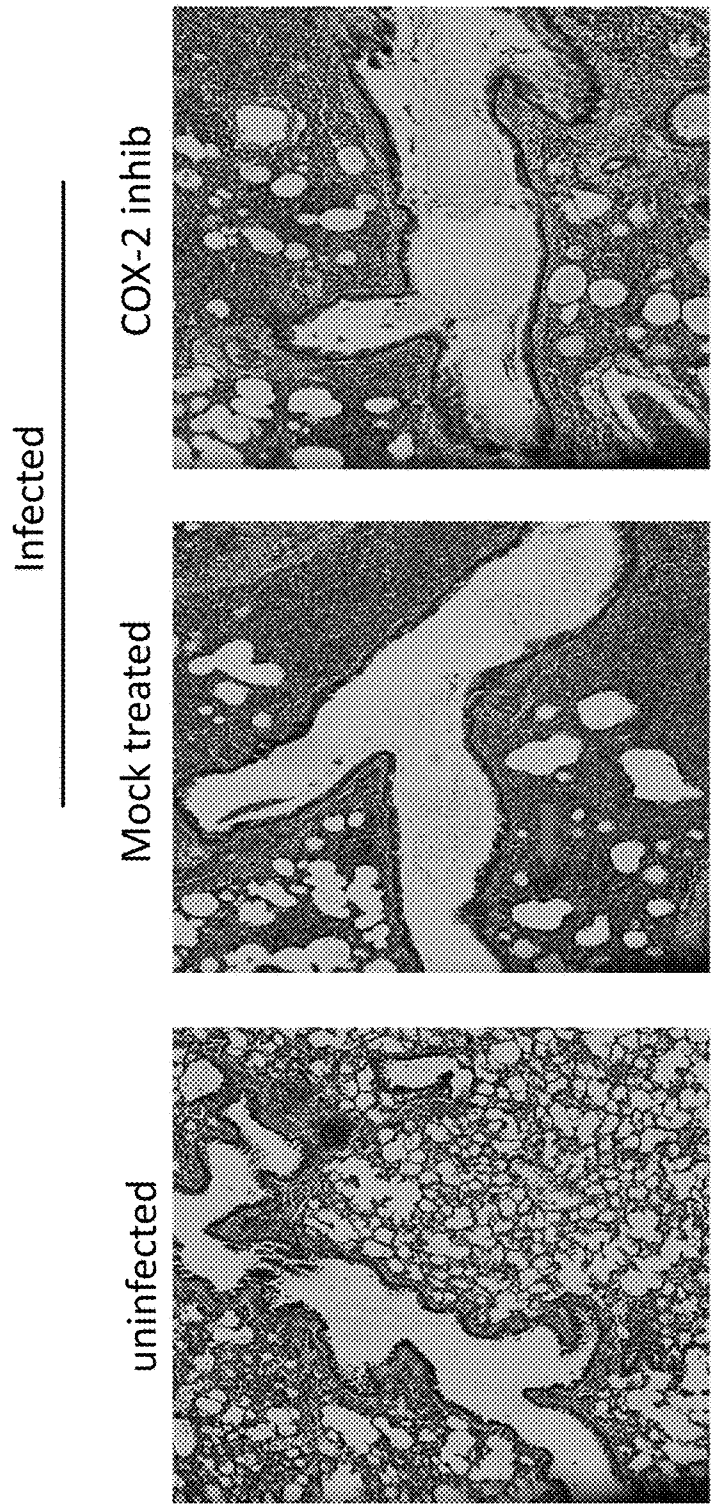
FIG. 18. Lung inflammation is reduced in COX-2 treated mice infected with *B. thailandensis*. BALB/c mice were given 15 mg/kg COX-2 inhibitor (Celecoxib) or mock control and challenged concurrently with 3 LD50 *B. thailandensis* by intranasal inoculation. Animals were sacrificed at 48 hours post-infection and lungs were stained with H&E (Hematoxylin and eosin stain). Arrow denotes abundant accumulation of inflammatory cells in mock-treated infected mice. Images obtained at 40× magnification.
Figure 19:
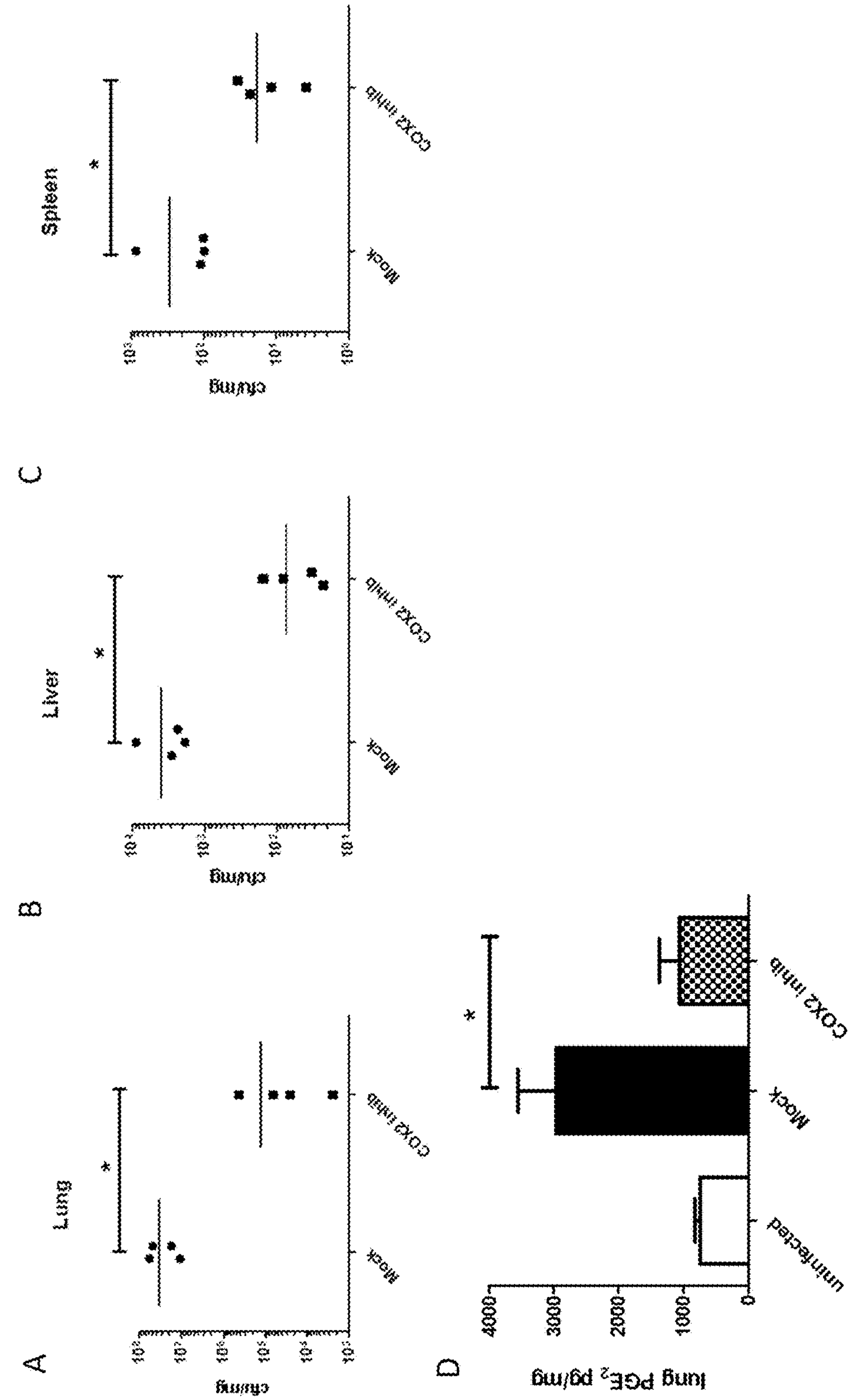
FIG. 19. COX-2 inhibition reduces lung PGE-2 and tissue bacterial burdens in *B. thailandensis*-infected mice. BALB/c mice were given 80 mg/kg Celecoxib or a mock control and infected i.n. with 3LD50 *B. thailandensis*. At 48 hours post-infection, mice were sacrificed and lung (FIG. 19A), liver (FIG. 19B), and spleen (FIG. 19C) homogenates plated to determine bacterial cfu.

Consistent with these findings, COX-2 inhibition also reduced tissue bacterial burdens and pulmonary inflammation in mice infected with *B. thailandensis* (FIGS. 18-19). In order to compare the inflammatory responses in the lungs of drug- and mock-treated mice, histological and cytokine analyses were performed on lung tissue obtained 48 hours post-challenge. Histological examination showed no evidence of pulmonary inflammation in naïve, uninfected mice, as shown in FIG. 18. In contrast, severe inflammatory cell infiltration was apparent in the peri-bronchial and perivascular regions of the lungs following Bt challenge. The inflammation was reduced in the Celecoxib-treated mice with less evidence of inflammatory cells than mock-treated mice, as shown by FIG. 18.

To explore the role of PGE-2 during acute melioidosis, mice were orally administered the COX-2 inhibitor Celecoxib or a mock control of DMSO four hours prior to bacterial challenge. Bacterial burdens in lung, liver, and spleen were determined at 48 hours post-infection. Mice that received the COX-2 inhibitor demonstrated a reduction in bacterial burdens in all tissues examined compared to mock-treated mice, as shown in FIGS. 19A, 19B, and 19C. PGE-2 reduction in the lungs of Celecoxib-treated mice was confirmed by ELISA, as shown in FIG. 19D. Together, these data indicate that induction of endogenous COX-2 and PGE-2 by Bt suppresses bacterial clearance in vivo.

Example B6—Effect of COX-2 Inhibition on Lung Arginase

Figure 20:
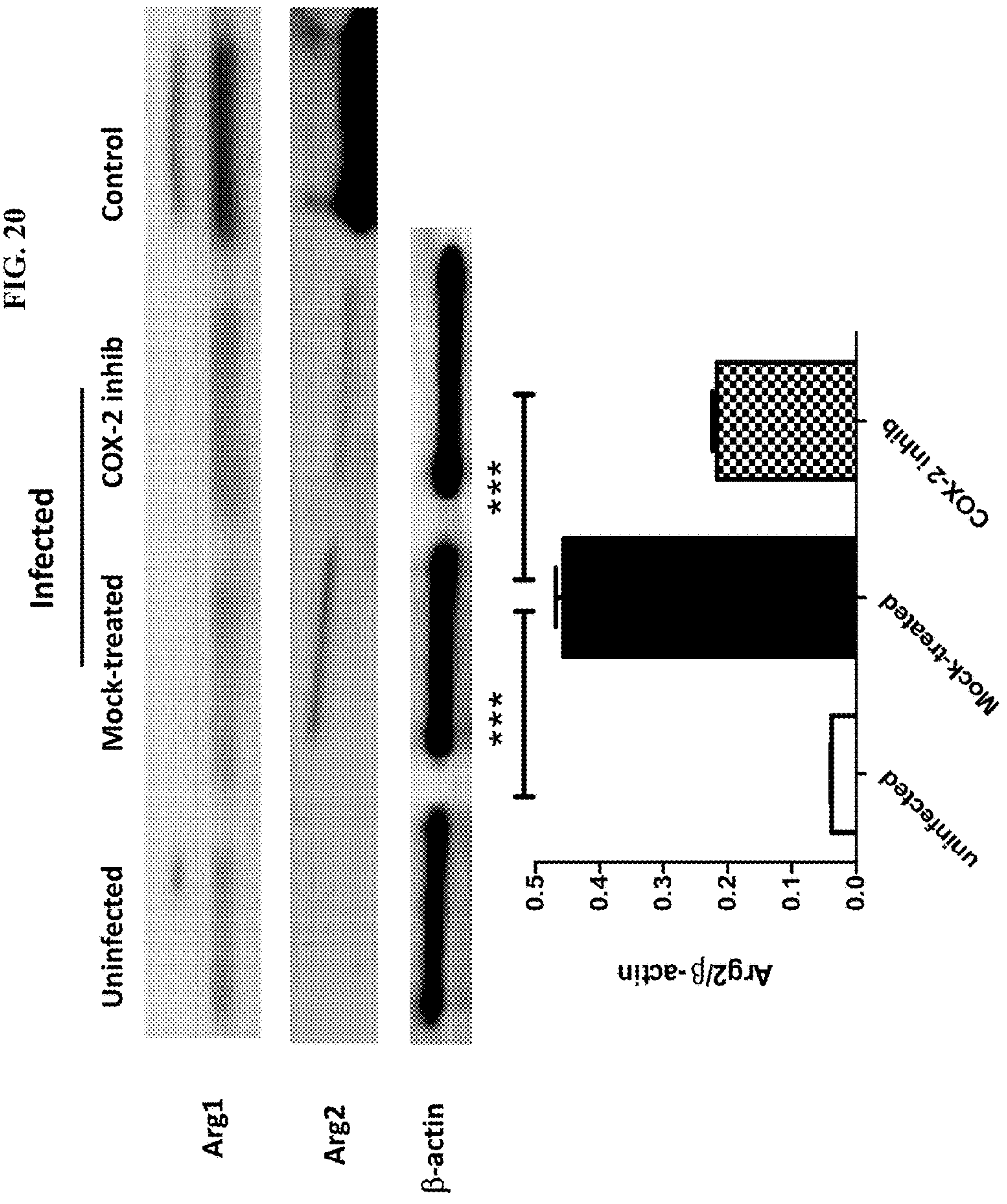
FIG. 20. Arg2 is expressed in the lungs of *B. pseudomallei*-infected mice and decreases upon COX-2 inhibition. Arg1 and Arg2 expression was examined by Western blot in lung homogenates of uninfected and Bps-infected mice (n=3 per group) treated with 15 mg/kg NS398 or mock control. Mouse liver extract and mouse Arg2-transfected 293T cell lysate were used as positive controls for Arg1 and Arg2 respectively. β-actin was used as a loading control and for normalization in densitometry analysis using the ImageJ program: <<http://rsb.info.nih.gov/ij/>>. Statistical significance was determined using one-way ANOVA with Bonferroni post test.

*B. pseudomallei* infection led to increased PGE-2 and Arg2 expression in macrophages and both PGE-2 and Arg2 enhanced *B. pseudomallei* intracellular survival. Furthermore, PGE-2 positively regulated Arg2 expression in response to *B. pseudomallei* in vitro. We therefore evaluated Arg2 expression in the lungs of mice in response to bacterial infectious disease and COX-2 inhibition. Similar to our in vitro observations, an increase in lung Arg2, but not Arg1, was observed in *B. pseudomallei*-infected animals compared to uninfected animals (FIG. 20). Upon COX-2 inhibition, a reduction in lung Arg2 was observed in *B. pseudomallei*-infected mice as evident by Western blot and densitometry analysis (FIG. 20). These results corroborate our observations in murine macrophages and advocate a supporting role for Arg2 in PGE-2-mediated immunosuppression during *B. pseudomallei* infection.

EXAMPLE SET C

Example C1—Exogenous PGE-2 Reduces IFN-γ and IL-2 Production by Stimulated CD4+ T-Cells Methods: CD4+ T cells were purified from spleens of naïve C57B1/6 mice using negative selection. T-cells were then incubated in RPMI (unstimulated) or RPMI plus immobilized Anti-CD3, Anti-cd28, and IL-2 (stimulated) or RPMI plus immobilized Anti-CD3, Anti-cd28, and IL-2 PLUS low dose (100 pg/ml) or high dose (10,000 pg/ml) PGE-2. On Day 3, Cells were spun down and resuspended in fresh media with the appropriate above conditions. On Day 6, cells were harvested, fixed, plugged, and stained for surface markers and intracellular IL-2 and IFN-gamma.

FIG. 21A shows that exogenous PGE-2 reduces IFN-gamma and IL-2 production by stimulated CD4+ T-cells. The percent of CD4+ T-cells is significantly statistically different when comparing unstimulated, low dose PGE-2, high dose PGE-2 to stimulated, as indicated by $p<0.01$, *$p<0.001$, or ****$p<0.0001$.

Example C2—Supernatant from Bp82-Infected RAW Macrophages Reduces IFN-γ and IL-2 Production by Stimulated CD4+ T-Cells Methods: RAW 267.4 macrophages were grown to confluency and infected with Bp82 at an MOI of 1:1, or stimulated with Bt LPS or left untreated. After 6 hours, cells were spun down and supernatant was collected. CD4+ T cells were purified from spleens of naïve B1/6 mice using negative selection. T-cells were then incubated in RPMI (unstimulated) or RPMI plus immobilized Anti-CD3, Anti-cd28, and IL-2 (stimulated) or RPMI plus immobilized Anti-CD3, Anti-cd28, and IL-2 PLUS 250 µl supernatants from Bp82 infected RAW cells, LPS stimulated RAW cells, or raw cells alone. On Day 3, Cells were spun down and resuspended in fresh media with the same conditions. On Day 6, cells were harvested, fixed, plugged and stained for surface markers and intracellular IL-2 and IFN-gamma.

FIG. 21B shows that the supernatant from RAW cells infected with Bp82 or stimulated with LPS are able to reduce IFN-gamma and IL-2 production by stimulated CD4+ T-cells. The percent of CD4+ T-cells is significantly statistically different when comparing to Bp82 and LPS treated cells to untreated RAW cells, as indicated by *$p<0.05$, $p<0.01$, *$p<0.001$, or ****$p<0.0001$.

Example C3—COX-2 Reduces PGE-2 and Suppresses Growth in *B. pseudomallei* in Lung and Stomach Tissue Methods: At time point zero, 4 BALB/C mice were infected with *B. pseudomallei* via aerosol challenge, at a dose of $1.48\times10^{-7}$ CFU/mL. Three hours post infection, 2 mice (n=2) were administered NS398 (a COX-2 inhibitor) i.p. at a dose of 15 mg/kg dissolved in DMSO, for a total injection volume of 50 Tµl. Two mice were mock treated with DMSO (n=2). At 24 hours after the first treatment (27 hours post-infection), each mouse was again administered 15 mg/kg NS398 or mock treated with DMSO. A third administration of treatment of the same dosage or mock treatment was given 24 hours after the second treatment (51 hours post-infection).

At time of death, stomach, lungs, liver, and spleen were taken from each mouse, homogenized, and plated on PIA agar. CFU/mg of lung and stomach are shown in FIGS. 22C and 22D, as discussed below.

The homogenized stomach and lungs were filtered and determined to be sterile. Filtrate was then stored in −20° C. for further analysis of PGE-2 concentration. PGE-2 concentration of each organ homogenate was analyzed using a PGE-2 ELISA kit (ThermoScientific). Concentrations of PGE-2 in pg/ml in the lung and stomach are shown in FIGS. 22A and 22B, as discussed below.

Concentrations of PGE-2 in pg/ml in the lung for each group of mice can be seen in FIG. 22A. FIG. 22A shows that NS398, a commercially available COX-2 inhibitor, was able to reduce PGE-2 concentration in lung tissue in treated mice, as compared to mice without NS398 treatment.

Concentrations of PGE-2 in pg/ml in the stomach for each group of mice can be seen in FIG. 22B. FIG. 22B shows that NS398, a commercially available COX-2 inhibitor, was able to reduce PGE-2 concentration in stomach tissue in treated mice, as compared to mice without NS398 treatment.

CFU/mg of lung from each group can be seen in FIG. 22C. FIG. 22C shows that treatment of mice with NS398 suppresses the growth of *B. pseudomallei* in lung tissue during aerosol challenge with the bacteria, when compared to mice that were not treated with NS398.

CFU/mg of stomach from each group can be seen in FIG. 22D. FIG. 22D shows that treatment of mice with NS398 suppresses the growth of *B. pseudomallei* in stomach tissue during aerosol challenge with the bacteria, when compared to mice that were not treated with NS398.

The headings used in the disclosure are not meant to suggest that all disclosure relating to the heading is found within the section that starts with the heading. Disclosure for any subject may be found throughout the specification.

As used in the disclosure and the claims, the term "about" applies to all numeric values, whether or not explicitly indicated. The term "about" generally refers to a range of numbers that one would consider equivalent to the recited value (i.e., having the same function or result). In some instances, the term "about" may include numbers that are rounded to the nearest significant figure.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

What is claimed is:

1. A method for treating a bacterial infectious disease in an animal comprising administering a therapeutically effective amount of one or more COX inhibitors to the animal, wherein the bacterial infectious disease is (a) a *Burkholderia* infection or melioidosis, or (b) an infection caused by *Burkholderia pseudomallei, Burkholderia mallei, Burkholderia thailandensis, Klebsiella pneumoniae*, or *Shigella flexneri.*

2. The method of claim 1, wherein the administering is applied to the animal post-exposure to the bacterial infectious disease or prior to exposure to the bacterial infectious disease.

3. The method of claim 1, wherein administering a therapeutically effective amount of one or more COX inhibitors occurs not more than about 30 minutes after exposure, not more than about 24 hours after exposure, or not more than about 48 hours after exposure.

4. The method of claim 1, wherein the method further comprises administering a therapeutically effective amount of one or more antibiotics.

5. The method of claim 1, wherein the method further comprises administering a therapeutically effective amount of one or more antibiotics applied to the animal post-exposure to the bacterial infectious disease or prior to exposure to the bacterial infectious disease.

6. The method of claim 1, wherein the method further comprises administering a therapeutically effective amount of one or more antibiotics selected from Sulfonamides, Cephalosporins, Sulfamethizole, Sulfamethoxazole, Sulfisoxazole, Trimethoprim-Sulfamethoxazole, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, and Doxycycline.

7. The method of claim 1, wherein the method does not comprise administering an antibiotic to the animal.

8. The method of claim 1, wherein the bacterial infectious disease, when untreated or when treated by one or more antibiotics only, results in one or more of (a) increasing PGE-2 production in the animal, (b) increasing Arg2 expression in the animal, (c) increasing arginase production in the animal, (d) decreasing NO production in the animal, (e) weight loss in the animal, or (f) an increase in the bacterial load of the infecting bacteria in the animal.

9. The method of claim 1, wherein the bacterial infectious disease, when untreated or when treated by one or more antibiotics only, results in increasing PGE-2 production in the animal, results in an increase in the bacterial load of the infecting bacteria in the animal, or both.

10. The method of claim 1, wherein the bacterial infectious disease is caused by a Gram-negative bacteria or a Gram-positive bacteria.

11. The method of claim 1, wherein the bacterial infectious disease is caused by a drug-resistant bacteria or a multidrug-resistant bacteria.

12. The method of claim 1, wherein (a) the bacterial infectious disease is caused by a drug-resistant bacteria or a multidrug-resistant bacteria and (b) the bacterial infectious disease results in increasing PGE-2 production in the animal.

13. The method of claim 1, wherein the bacterial infectious disease is a *Burkholderia* infection or melioidosis.

14. The method of claim 1, wherein the one or more COX inhibitors is a COX-2 inhibitor.

15. The method of claim 1, wherein the one or more COX inhibitors is Lumiracoxib, Etoricoxib, Valdicoxib, Rofi-coxib, Etodolac, Celecoxib, NS398, or Indomethacin.

16. The method of claim 1, wherein the dosage of one of the one or more COX inhibitors is at least about two-fold higher compared to a COX inhibitor dosage for long term usage.

17. The method of claim 1, wherein the bacterial load of the infecting bacteria in the animal decreases by at least about 50% in about 24 hours after starting the treatment.

18. The method of claim 1, wherein the method results in one or more of (a) decreasing PGE-2 production in the animal, (b) decreasing Arg2 expression in the animal, (c) decreasing arginase production in the animal, (d) increasing NO production in the animal, (e) a lack of weight loss in the animal, or (f) a decrease in the bacterial load of the infecting bacteria.

19. The method of claim 1, wherein the bacterial infectious disease infects, in the animal, one or more of lung, liver, esophagus, stomach, eye, nose, sinus, ear, ear canal, mouth, hand, foot, urethra, or spleen.

20. The method of claim 1, wherein the animal is not cured of the bacterial infectious disease by an antibiotic(s) only treatment.

21. The method of claim 1, wherein the animal is exposed to the bacterial infectious disease and exposure is through the skin, inhalation, injection, or contact with a mucous membrane.

22. The method of claim 1, wherein the manner of administration of one of the one or more COX inhibitors is by pill, liquid, aerosol, intranasal administration, topical administration, or injection.

23. The method of claim 1, wherein the manner of administration of the one or more COX inhibitors does not include topical administration of an eye.

24. The method of claim 4, wherein the manner of administration of one of the one or more antibiotics is by pill, liquid, aerosol, intranasal administration, topical administration, or injection.

25. The method of claim 4, wherein the manner of administration of the one or more antibiotics does not include topical administration of an eye.

26. The method of claim 1, wherein the animal displays one or more symptoms of the bacterial infectious disease.

27. The method of claim 1, wherein the animal is diagnosed with the bacterial infectious disease.

28. The method of claim 1, wherein the animal is post-exposure to the bacterial infectious disease.

29. A method for treating a bacterial infectious disease in an animal comprising administering a therapeutically effective amount of one or more COX inhibitors, and optionally administering a therapeutically effective amount of one or more antibiotics, wherein the administering steps are applied to the animal, wherein the bacterial infectious disease is (a) a *Burkholderia* infection or melioidosis, or (b) an infection caused by *Burkholderia pseudomallei, Burkholderia mallei, Burkholderia thailandensis, Klebsiella pneumoniae*, or *Shigella flexneri.*

30. A method for treating a bacterial infectious disease in an animal comprising administering a therapeutically effective amount of one or more COX inhibitors to the animal prior to exposure to the bacterial infectious disease, wherein the bacterial infectious disease is (a) a *Burkholderia* infection or melioidosis, or (b) an infection caused by *Burkholderia pseudomallei, Burkholderia mallei, Burkholderia thailandensis, Klebsiella pneumoniae*, or *Shigella flexneri.*

31. The method of claim 30, wherein the method further comprises administering a therapeutically effective amount of one or more antibiotics to the animal prior to exposure to the bacterial infectious disease.

32. A method for decreasing a bacterial load of an infecting bacteria in an animal with a bacterial infectious disease comprising administering a therapeutically effective amount of one or more COX inhibitors to the animal, wherein the bacterial infectious disease is (a) a *Burkholderia* infection or melioidosis, or (b) an infection caused by *Burkholderia pseudomallei, Burkholderia mallei, Burkholderia thailandensis, Klebsiella pneumoniae*, or *Shigella flexneri.*

33. The method of claim 32, wherein the method further comprises administering a therapeutically effective amount of one or more antibiotics to the animal.

34. A method for decreasing PGE-2 production in an animal with a bacterial infectious disease comprising administering a therapeutically effective amount of one or more COX inhibitors to the animal, wherein the bacterial infectious disease is (a) a *Burkholderia* infection or melioidosis, or (b) an infection caused by *Burkholderia pseudomallei, Burkholderia mallei, Burkholderia thailandensis, Klebsiella pneumoniae*, or *Shigella flexneri.*

35. A method for treating a bacterial infectious disease in an animal comprising administering a therapeutically effective amount of one or more COX inhibitors to the animal, wherein the bacterial infectious disease is (a) a *Burkholderia* infection, an *Enterococcus* infection, or melioidosis, or (b) an infection caused by *Burkholderia pseudomallei, Burkholderia mallei, Burkholderia thailandensis, Klebsiella pneumoniae*, or *Shigella flexneri.*

36. A method for treating a bacterial infectious disease in an animal comprising administering a therapeutically effective amount of one or more COX inhibitors to the animal, and administering a therapeutically effective amount of one or more antibiotics, wherein the administering steps are applied to the animal, wherein the bacterial infectious disease is (a) a mucosal bacterial infection, a *Burkholderia* infection, a *Mycobacterial* infection, an *Enterococcus* infection, melioidosis, or tuberculosis, or (b) an infection caused by *Burkholderia pseudomallei, Burkholderia mallei, Burkholderia thailandensis, Mycobacterium tuberculosis, Pseudomonas aeruginosa, Klebsiella pneumoniae, Salmonella*, or *Shigella flexneri.*

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: GAPDH forward primer sequence

<400> SEQUENCE: 1

acagccgcat cttcttgtgc agtg                                            24


<210> SEQ ID NO 2
<211> LENGTH: 24
<212> TYPE: DNA
<213> ORGANISM: Artificial Sequence
<220> FEATURE:
<223> OTHER INFORMATION: GAPDH reverse primer sequence

<400> SEQUENCE: 2

ggccttgact gtgccgttga attt                                            24


<210> SEQ ID NO 3
<211> LENGTH: 24
<212> TYPE: DNA
<213> ORGANISM: Artificial Sequence
<220> FEATURE:
<223> OTHER INFORMATION: Arg1 forward primer sequence

<400> SEQUENCE: 3

gggctggacc cagcattcac cccg                                            24


<210> SEQ ID NO 4
<211> LENGTH: 24
<212> TYPE: DNA
<213> ORGANISM: Artificial Sequence
<220> FEATURE:
<223> OTHER INFORMATION: Arg1 reverse primer sequence

<400> SEQUENCE: 4

tcacttaggt ggtttaaggt agtc                                            24


<210> SEQ ID NO 5
<211> LENGTH: 24
<212> TYPE: DNA
<213> ORGANISM: Artificial Sequence
<220> FEATURE:
```

-continued

```
<223> OTHER INFORMATION: Arg2 forward primer sequence

<400> SEQUENCE: 5

gaccctaaac tggctccagc caca                                       24


<210> SEQ ID NO 6
<211> LENGTH: 24
<212> TYPE: DNA
<213> ORGANISM: Artificial Sequence
<220> FEATURE:
<223> OTHER INFORMATION: Arg2 reverse primer sequence

<400> SEQUENCE: 6

ctaaattctc acacattctt catt                                       24


<210> SEQ ID NO 7
<211> LENGTH: 20
<212> TYPE: DNA
<213> ORGANISM: Artificial Sequence
<220> FEATURE:
<223> OTHER INFORMATION: iNOS forward primer sequence

<400> SEQUENCE: 7

atgaccagta taaggcaagc                                            20


<210> SEQ ID NO 8
<211> LENGTH: 21
<212> TYPE: DNA
<213> ORGANISM: Artificial Sequence
<220> FEATURE:
<223> OTHER INFORMATION: iNOS reverse primer sequence

<400> SEQUENCE: 8

gctctggatg agcctatatt g                                          21


<210> SEQ ID NO 9
<211> LENGTH: 21
<212> TYPE: DNA
<213> ORGANISM: Artificial Sequence
<220> FEATURE:
<223> OTHER INFORMATION: COX-2 forward primer sequence

<400> SEQUENCE: 9

ggagagaagg aaatggctgc a                                          21


<210> SEQ ID NO 10
<211> LENGTH: 20
<212> TYPE: DNA
<213> ORGANISM: Artificial Sequence
<220> FEATURE:
<223> OTHER INFORMATION: COX-2 reverse primer sequence

<400> SEQUENCE: 10

atctagtctg gagtgggagg                                            20
```